US008143480B2

(12) United States Patent
Axtell et al.

(10) Patent No.: US 8,143,480 B2
(45) Date of Patent: Mar. 27, 2012

(54) COMPOSITIONS AND METHODS FOR EFFICIENT GENE SILENCING IN PLANTS

(75) Inventors: Michael Axtell, State College, PA (US); David P. Bartel, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 835 days.

(21) Appl. No.: 11/975,725

(22) Filed: Oct. 19, 2007

(65) Prior Publication Data
US 2009/0172838 A1 Jul. 2, 2009

Related U.S. Application Data

(63) Continuation of application No. 11/699,313, filed on Jan. 26, 2007, now abandoned.

(60) Provisional application No. 60/762,991, filed on Jan. 27, 2006, provisional application No. 60/856,447, filed on Nov. 2, 2006.

(51) Int. Cl.
*A01H 1/00* (2006.01)
*C07H 21/02* (2006.01)
*C12N 15/00* (2006.01)

(52) U.S. Cl. ......... 800/285; 435/6.1; 435/463; 435/468; 435/419; 435/320.1; 536/23.1; 536/24.5; 800/278

(58) Field of Classification Search ............... 435/6.1, 435/463, 468, 419, 320.1; 536/23.1, 24.5; 800/278, 285
See application file for complete search history.

(56) References Cited

U.S. PATENT DOCUMENTS

| 5,750,848 | A | 5/1998 | Kruger et al. |
| 5,763,245 | A | 6/1998 | Greenplate et al. |
| 6,194,636 | B1 | 2/2001 | McElroy et al. |
| 6,207,879 | B1 | 3/2001 | McElroy et al. |
| 6,232,526 | B1 | 5/2001 | McElroy et al. |
| 6,372,965 | B1 | 4/2002 | Lightner et al. |
| 6,426,446 | B1 | 7/2002 | McElroy et al. |
| 6,426,448 | B1 | 7/2002 | Booth, Jr. et al. |
| 6,429,357 | B1 | 8/2002 | McElroy et al. |
| 6,433,252 | B1 | 8/2002 | Kriz et al. |
| 6,437,217 | B1 | 8/2002 | McElroy et al. |
| 6,583,338 | B2 | 6/2003 | McElroy et al. |
| 6,759,575 | B2 | 7/2004 | Michiels et al. |
| 6,872,872 | B1 | 3/2005 | Lightner et al. |
| 7,064,243 | B2 | 6/2006 | Liu et al. |
| 2003/0180756 | A1 | 9/2003 | Shi et al. |
| 2004/0098761 | A1 | 5/2004 | Trick et al. |
| 2005/0138689 | A1 | 6/2005 | Aukerman |
| 2005/0144669 | A1 | 6/2005 | Reinhart et al. |
| 2006/0174380 | A1 | 8/2006 | Carrington et al. |
| 2006/0200878 | A1 | 9/2006 | Lutfiyya et al. |
| 2006/0236427 | A1 | 10/2006 | Chiang et al. |
| 2007/0118918 | A1* | 5/2007 | Huang et al. .................. 800/278 |

FOREIGN PATENT DOCUMENTS

| WO | WO-95/06128 | 3/1995 |
| WO | WO-02/057471 A2 | 7/2002 |
| WO | WO-2005/007829 | 1/2005 |
| WO | WO-2008/063203 | 5/2008 |

OTHER PUBLICATIONS

Shen et al., Plant Syst. Evol., 2009, vol. 282, pp. 125-132.*
Axtell et al., Cell, 2006, vol. 127, pp. 565-577.*
Felippe et al., EMBO Reports, 2009, vol. 10, pp. 264-270.*
Adenot et al. "DRB4-dependent TAS3 trans-acting siRNAs control leaf morphology through AGO7." Curr Biol. 16:927-932 (2006).
Allen et al. "Evolution of microRNA genes by inverted duplication of target gene sequences in *Arabidopsis thaliana*." Nat. Genet. 36:1282-1290 (2004).
Allen et al., microRNA-Directed Phasing during Trans-Acting siRNA Biogenesis in Plants. Cell. 121: 207-221 (2005).
Ambros et al., "A uniform system for microRNA annotation." RNA, 9(3): 277-279 (2003).
Anterola et al., Trends in lignin modification: a comprehensive analysis of the effects of genetic manipulations/mutations on lignifications and vascular integrity. Phytochemistry. 62:221-294 (2002).
Arazi et al., "Cloning and characterization of micro-RNAs from moss." Plant J. 43:837-848 (2005).
Axtell et al. "Antiquity of microRNAs and their targets in land plants." Plant Cell. 17:1658-1673 (2005).
Bartel, D.P., "MicroRNAs: genomics, biogenesis, mechanism, and function." Cell. 116, 281-297 (2004).
Boerjan et al., Lignin Biosynthesis. Annu. Rev. Plant Biol. 54:519-546 (2003).
Bouche et al. "An antagonistic function for Arabidopsis DCL2 in development and a new function for DCL4 in generating viral siRNAs." EMBO J. 25:3347-3356 (2006).
Chen, X., "microRNA biogenesis and function in plants." FEBS Letters 579:5923-5931(2005).
Deleris et al. "Hierarchical action and inhibition of plant Dicer-Like proteins in antiviral defense." Science 313:68-71 (2006).
Elmayan and Vaucheret, "Expression of single copies of a strongly expressed 35S transgene can be silenced post-transcriptionally." Plant J. 9:787-789 (1996).
Fahlgren et al. "Regulation of Auxin Response FACTOR3 by TAS3 ta-siRNA affects developmental timing and patterning in Arabidopsis." Curr. Biol. 16:939-944 (2006).

(Continued)

*Primary Examiner* — Phuong Bui
(74) *Attorney, Agent, or Firm* — Ropes & Gray LLP

(57) ABSTRACT

This invention relates to methods for knock-down of a target gene in plants, particularly efficient and specific methods for knock-down of a target gene in plants. This invention also relates to methods for silencing endogenous plant genes or plant pathogen genes. It further relates to nucleic acid constructs (DNA, RNA) which comprise a nucleic acid sequence that corresponds to a target gene or fragment thereof flanked by two complementary sites to an smRNA, e.g., a miRNA (one complementary site is on either side of the nucleic acid sequence), resulting in, for example the configuration: complementary site—nucleic acid sequence that corresponds to a target gene—complementary site.

3 Claims, 30 Drawing Sheets

OTHER PUBLICATIONS

Garcia et al. "Specification of leaf polarity in *Arabidopsis* vis the trans-acting siRNA Pathway." Curr. Biol. 16:933-938 (2006).

Gasciolli et al., "Partially redundant functions of *Arabidopsis* Dicer-like enzymes and a role for DCL4 in producing trans-acting siRNAs." Curr Biol. 15:1494-1500 (2005).

Griffiths-Jones et al., "The microRNA Registry." Nucleic Acids Research, 32, Database Issue, D109-D111 (2004).

Griffiths-Jones et al., "miRBase: microRNA sequences, targets and gene nomenclature." Nucleic Acids Research, 34, Database Issue, D140-D144 (2006).

Hunter et al. "Trans-acting siRNA-mediated repression of ETTIN and ARF4 regulates heteroblasty in *Arabidopsis*." Development. 133:2973-2981 (2006).

Jones-Rhoades et al., "MicroRNAs and Their Regulatory Roles in Plants." Annu Rev Plant Biol., 57:19-53 (2006).

Jones-Rhoades, et al., "Computational Identification of Plant MicroRNAs and Their Targets, Including a Stress-Induced miRNA." Mol. Cell. 14(6):787-99 (2004).

Lau et al., "An abundant class of tiny RNAs with probably regulatory roles in *Caenorhabditis elegans*." Science. 294:858-862 (2001).

Lindbo et al., "Induction of a highly specific antiviral state in transgenic plants: Implications for regulation of gene expression and virus resistance." Plant Cell 5, 1749-1759. (1993).

Llave et al., "Cleavage of Scarecrow-like mRNA targets directed by a class of *Arabidopsis* miRNA." Science 297, 2053-2056 (2002).

Lu et al., "Elucidation of the small RNA component of the transcriptome." Science. 309:1567-1569 (2005).

Mallory et al., "MicroRNA control of PHABULOSA in leaf development: importance of pairing to the microRNA 5' region." EMBO J. 23:3356-3364 (2004).

Margulies et al. "Genome sequencing in microfabricated high-density picolitre reactors." Nature. 437: 376-380 (2005).

Meins et al., "RNA Silencing Systems and Their Relevance to Plant Development." Annu Rev Cell Dev Biol., 21:297-318 (2005).

Niu, Q-W et al., "Expression of artificial microRNAs in transgenic *A. thaliana* confers virus resistance," Nat. Biotechnol., online publication Oct. 26, 2006.

Parizotto et al. "In vivo investigation of the transcription, processing, endonucleolytic activity, and functional relevance of the spatial distribution of a plant miRNA." Genes Dev. 18:2237-2242 (2004).

Peragine et al. "SGS3 and SGS2/SDE1/RDR6 are required for juvenile development and the production of transacting srRNAs in *Arabidopsis*." Genes Devel. 18:2368-2379 (2002).

Rhoades et al. "Prediction of plant microRNA targets." Cell. 110: 513-520 (2002).

Ronemus et al. "MicroRNA-targeted and small interfering RNA-mediated mRNA degradation is regulated by Arhonaute, Dicer and RNA-dependent RNA polymerase in *Arabidopsis*." Plant Cell. 18:1559-1574 (2006).

Schwab et al. "Specific effects of microRNAs on the plant transcriptome." Dev Cell. 8:517-527 (2005).

Smith et al. "Transgenic plant virus resistance mediated by untranslatable sense RNAs: Expression, regulation and fate of nonessential RNAs." Plant Cell. 6:1441-1453 (1994).

Sunkar et al. "Novel and stress-regulated microRNAs and other small RNAs from *Arabidopsis*." Plant Cell. 16:2001-2019 (2004).

Tang et al. "A biochemical framework for RNA silencing in plants." Genes Dev. 17:49-63 (2003).

Vazquez et al. "Endogenous trans-acting siRNAs regulate the accumulation of Arabidopsis mRNAs." Mol Cell. 16:69-79 (2004).

Vazquez et al. "The nuclear dsRNA binding protein HYL1 is required for microRNA accumulation and plant development, but not post-transcriptional transgene silencing." Curr Biol. 14:346-351 (2004).

Williams et al. "A database analysis method identifies an endogenous trans-acting short-interfering RNA that targets the *Arabidopsis* ARF2, ARF3, and ARF4 genes." Proc. Natll. Acad. Sci. USA 102:9703-9708 (2005).

Xie et al. "Dicer-Like 4 functions in trans-acting small interfering RNA biogenesis and vegetative phase change in Arabidopsis thaliana." Proc. Natl. Acad. Sci. USA 102:12984-12989, (2005).

Xie et al. "Genetic and functional diversification of small RNA pathways in plants." PLoS Bio. 2(5):642-652 (2004).

Yoshikawa et al. "A pathway for the biogenesis of trans-acting siRNAs in *Arabidopsis*." Genes Dev. 19:2164-2175 (2005).

Zamore and Haley, "Ribo-gnome: the big world of small RNAs." Science 309:1519-1524 (2005).

* cited by examiner

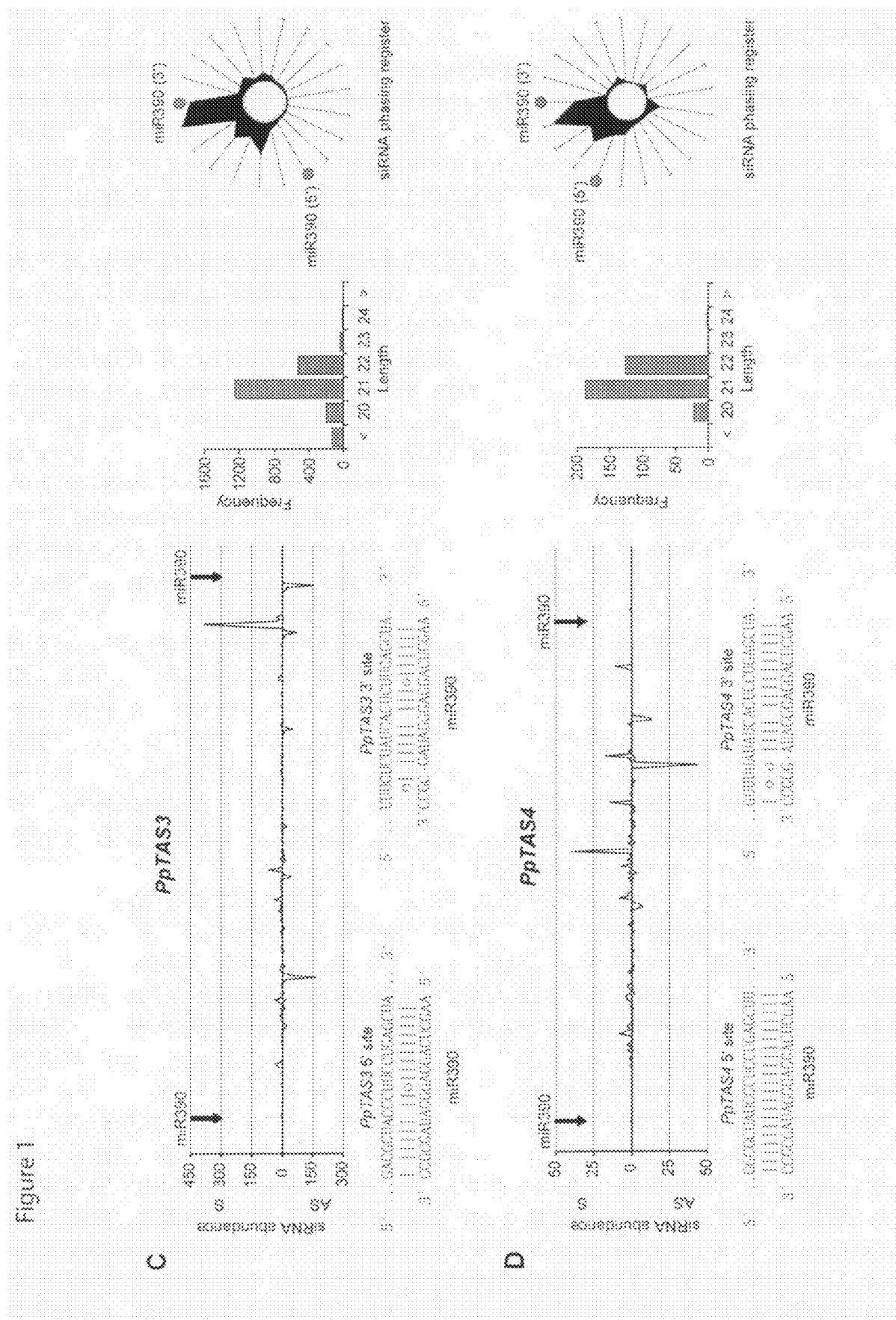

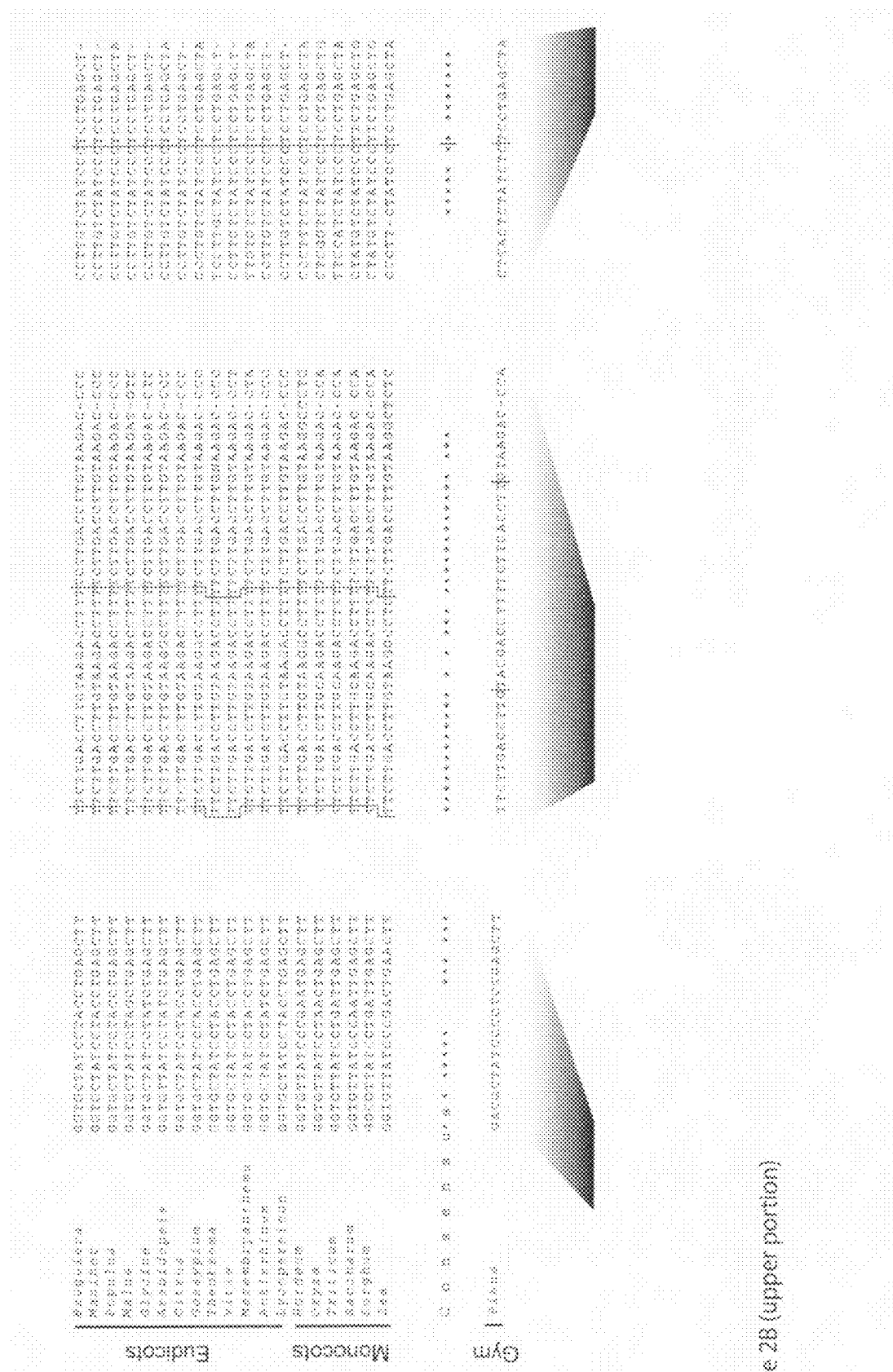
Figure 2B (upper portion)

Table 1

| miRNA / small RNA | species | Accession | complementary site | coordinates | complementary site | coordinates |
|---|---|---|---|---|---|---|
| miR390 | Citrus x paradisi | DN957942 | GGUGCUAUCCUACCUGAGCUU | 133 to 153 | UUGUCUAUCCCUCCUGAGCUG | 363 to 383 |
| miR390 | Manihot esculenta | CK652751 | GGUGCUAUCCUACCUGAGCUU | 180 to 200 | UUGUCUAUCCCUCCUGAGCUA | 407 to 427 |
| miR390 | Populus tremula x Populus tremuloides | BU827022 | GGUGCUAUCCUACCUGAGCUU | 247 to 267 | UUGUCUAUCCCUCCUGAGCUG | 463 to 483 |
| miR390 | Pinus taeda | CO161996 | GACGCUAUCCUACCCCUGAGCUU | 304 to 324 | UACUCUAUCUCCCUGAGCUA | 652 to 672 |
| miR390 | Populus trichocarpa | DT498974 | GGUGCUAUCCUACCUGAGCUU | 233 to 253 | UUGUCUAUCUCCCUGAGCUA | 448 to 468 |
| miR390 | Pinus taeda | DR112999 | GACGCUAUCCCCUGAGCUU | 248 to 268 | UACUCUAUCUCCCUGAGCUA | 596 to 616 |
| miR390 | Zea mays | AW400087 | GGUGUAUCCUGAUUGAGCUU | 315 to 335 | AGCUCUAUCCUUCCUGAGCUG | 503 to 523 |
| miR390 | Gossypium raimondii | CO077318 | GGUGCUAUCCCACCUGAGCUU | 308 to 328 | CUGUCUAUCCCUCCUGAGCUA | 565 to 585 |
| miR390 | Vitis vinifera | DT025007 | GGUGCUAUCCUACCUGAGCUU | 222 to 242 | UUGUCUAUCCCUCCUGAGCUA | 459 to 479 |
| miR390 | Euphorbia esula | DV119644 | GGUGCUAUCCUAUCUGAGCUU | 182 to 202 | UUGUCUAUCCCUCCUGAGCUU | 404 to 424 |
| miR390 | Lycopersicon esculentum | DV105041 | GGUGCUAUCCUACCUGAGCUU | 258 to 278 | UUGUCUAUCCUCCUGAGCUG | 515 to 535 |
| miR390 | Zea mays | BE519095 | GGUGUAUCCCGACUGAGAACUU | 144 to 164 | CCUUCUAUCCUCCUGAGCUA | 409 to 429 |
| miR390 | Vitis vinifera | DT019758 | GGUGCUAUCCUACCUGAGCUU | 218 to 238 | UUGUCUAUCCUCCUGAGCUA | 455 to 475 |
| miR390 | Gossypium raimondii | CO077320 | GGUGCUAUCCCACCUGAGCUU | 345 to 365 | CUGUCUAUCCUCCUGAGCUA | 602 to 622 |
| miR390 | Theobroma cacao | CA795323 | GGUGCUAUCCUACCUGAGCUU | 129 to 149 | CUUGCUAUCCUCCUGAGCUG | 383 to 403 |
| miR390 | Populus euphratica | AJ775737 | GGUGCUAUCCUACCUGAGCUU | 115 to 135 | GGUGCUAUCCUCCUGAGCUG | 327 to 347 |
| miR390 | Hordeum vulgare | BF264964 | GGUGUAUCCCGAAUGAGCUU | 306 to 326 | CUUUCUAUCCUCCUGAGCUA | 493 to 513 |
| miR390 | Manihot esculenta | CK643507 | GGUGCUAUCCUACCUGAGCUU | 141 to 161 | UUGUCUAUCCUCCUGAGCUA | 368 to 388 |
| miR390 | Malus x domestica | CO752478 | GGUGCUAUCCUACCUGAGCUU | 46 to 66 | UUGUCUAUCCUCCUGAGCUG | 296 to 316 |
| miR390 | Glycine max | BE330988 | GGUGCUAUCCUAUCGAGCUU | 178 to 198 | UUGUCUAUCCUCCUGAGCUG | 435 to 455 |
| miR390 | Sorghum bicolor | CD464142 | GGCGUAUCCUGAUUGAGCUU | 309 to 329 | AUGUCUAUCCUUCUGAGCUG | 521 to 541 |
| miR390 | Populus trichocarpa | DT498651 | GGUGCUAUCCUACCUGAGCUU | 241 to 261 | UUGUCUAUCCCUCCUGAGCUA | 459 to 479 |
| miR390 | Vitis vinifera | DT039941 | GGUGCUAUCCUACCUGAGCUU | 223 to 243 | UUGUCUAUCCCUCCUGAGCUA | 460 to 480 |
| miR390 | Citrus x paradisi x Poncirus trifoliata | CX663477 | GGUGCUAUCCUACCUGAGCUU | 256 to 276 | UUGUCUAUCCCUCCUGAGCUG | 487 to 507 |
| miR390 | Bruguiera gymnorhiza | BP947370 | GGUGUUAUCCUACCUGAUUGAGCUU | 293 to 313 | UUGUCUAUCCCUUCCUGAGCUG | 535 to 555 |
| miR390 | Sorghum bicolor | CD463999 | GGUGUUAUCCUACCUGAUUGAGCUU | 42 to 62 | AUGUCUAUCCUUCCUGAGCUG | 254 to 274 |
| miR390 | Triticum aestivum | CN010916 | GGUGUUAUCCUGAUUGAGCUU | 352 to 372 | CCAUCUAUCCCUCCUGAGCUA | 570 to 590 |
| miR390 | Malus x domestica | CN490861 | GGUGUUAUCCUAGCUGAUUGAGCUU | 142 to 162 | UUGUCUAUCCCUCCUGAGCUG | 394 to 414 |
| miR390 | Oryza sativa | AU100890 | GGUGUUAUCCUAACUGAUUGAGCUU | 303 to 323 | CGGUCUAUCCCUCCUGAGCUG | 535 to 555 |
| miR390 | Zea mays | DN214953 | GGUGUUAUCCUGAUUGAGCUU | 293 to 313 | AGCUCUAUCCUUCCUGAGCUU | 481 to 501 |
| miR390 | Populus tremula | CK114877 | GGUGCUAUCCUACCUGAGCUU | 264 to 284 | UUGUCUAUCCCUCCUGAGCUG | 476 to 496 |
| miR390 | Antirrhinum majus | AJ788438 | GGUGCUAUCCUAUCUGAGCUU | 242 to 262 | UUGUCUAUCCCUCCUGAGCUA | 502 to 522 |
| miR390 | Sorghum bicolor | AW677985 | GGCGUUAUCCUGAUUGAGCUU | 275 to 295 | AUGUCUAUCCCUUCUGAGCUG | 487 to 507 |

Figure 10A

Table 1

| miRNA / small RNA | species | Accession | complementary site | coordinates | complementary site | coordinates |
|---|---|---|---|---|---|---|
| miR390 | Populus trichocarpa x Populus deltoides | CN549499 | GGUGCUAUCCUACCUGAGCUU | 78 to 98 | UUAUCUAUCCCUCCUGAGCUA | 297 to 317 |
| miR390 | Mesembryanthemum crystallinum | BF479835 | GGUGCUAUCCUACCUGAGCUU | 166 to 186 | GUGCUAUCCCUCCUGAGCUA | 401 to 421 |
| miR390 | Zea mays | DN204953 | GGCGUUAUCCUAAUUGAGCUU | 356 to 376 | AUGUCUAUCCCUUCCUGAGCUG | 564 to 584 |
| miR390 | Populus trichocarpa | DT499672 | GGUGCUAUCCUACCUGAGCUU | 249 to 269 | UUAUCUAUCCCUCCUGAGCUA | 468 to 488 |
| miR390 | Populus trichocarpa | DT495406 | GGUGCUAUCCUACCUGAGCUU | 240 to 260 | UUGUCUAUCCCUCCUGAGCUA | 458 to 478 |
| miR390 | Antirrhinum majus | AJ797948 | GGUGCUAUCCUACCUGAGCUU | 260 to 280 | UUGCUAUCCCUCCUGAGCUA | 520 to 540 |
| miR390 | Zea mays | CB886528 | GGCGUUAUCCUAAUUGAGCUU | 260 to 280 | AUGUCUAUCCCUUCCUGAGCUG | 467 to 487 |
| miR390 | Populus deltoides | CX169705 | GGUGCUAUCCUACCUGAGCUU | 241 to 261 | UUGUCUAUCCCUCCUGAGCUA | 457 to 477 |
| miR390 | Triticum aestivum | BE442731 | GGUGUUAUCCUGAUUGAGCUU | 48 to 68 | CCAUCUAUCCCUCCGGAGCUA | 274 to 294 |
| miR390 | Citrus clementina | CX300562 | GGUGCUAUCCUACCUGAGCUU | 223 to 243 | UUGUCUAUCCCUCCUGAGCUG | 457 to 477 |
| miR390 | Glycine soja | BM558120 | GGUGCUAUCCUAUCUGAGCUU | 158 to 178 | UUGUCUAUCCCUCCUGAGCUG | 400 to 420 |
| miR390 | Manihot esculenta | CK652803 | GGUGCUAUCCUACCUGAGCUU | 179 to 199 | UUGUCUAUCCCUCCUGAGCUA | 406 to 426 |
| miR390 | Populus trichocarpa x Populus deltoides | CN523026 | GGUGCUAUCCUACCUGAGCUU | 198 to 218 | UUNNUAUCCCUCCUGAGCUAU | 413 to 434 |
| miR390 | Populus deltoides | CX174500 | GGUGCUAUCCUAUCCUGAGCUU | 220 to 240 | UUAUCUAUCCCUCCUGAGCUG | 439 to 459 |
| miR390 | Sorghum bicolor | AW677937 | GGCGUUAUCCUGAUUGAGCUU | 297 to 317 | AUGUCUAUCCCUCCUGAGCUG | 509 to 529 |
| miR390 | Saccharum officinarum | CA145655 | GGUGUUAUCCCAAUUGAGCUU | 198 to 218 | AUGUCUAUCCCUUCCUGAGCUG | 410 to 430 |
| miR390 | Zea mays | DV526105 | GGUGUUAUCCUGAUUGAGCUU | 312 to 332 | AGCUCUAUCCCUUCCUGAGCUG | 516 to 536 |
| miR390 | Populus trichocarpa | DT493496 | GGUGCUAUCCUACCUGAGCUU | 259 to 279 | UUAUCUAUCCCUCCUGAGCUA | 478 to 498 |
| miR390 | Zea mays | DT643611 | GGCGUUAUCCUAAUUGAGCUU | 699 to 719 | AUGUCUAUCCCUUCCUGAACUG | 906 to 926 |
| miR390 | Zea mays | CF012706 | GGUGUUAUCCGACUAAACUU | 364 to 384 | CCUUCUAUCCCUCCUGAGCUA | 629 to 649 |
| miR390 | Triticum aestivum | CK156495 | GGUGUUAUCCUGAUUGAGCUU | 242 to 262 | CCAUCUAUCCCUCCUGAGCUA | 460 to 480 |
| miR390 | Populus trichocarpa | DT495816 | GGUGCUAUCCUACCUGAGCUU | 261 to 281 | UUAUCUAUCCCUCCUGAGCUA | 480 to 500 |
| miR390 | Populus deltoides | CX177001 | GGUGCUAUCCUACCUGAGCUU | 226 to 246 | UUGUCUAUCCCUCCUGAGCUA | 442 to 462 |
| miR390 | Saccharum officinarum | CA148474 | GGUGUUAUCCUGAUCGAGCUU | 394 to 414 | AUGUCUAUCCCUUCCUGAGCUA | 606 to 626 |
| miR161.1 | Arabidopsis thaliana | At3g17185.1 | GGUGUUAUCCUAUCUGAGCUU | 217 to 237 | UUGUCUAUCCCUCCUGAGCUA | 460 to 481 |
| miR161.1 | Arabidopsis thaliana | At1g63130.1 | UCCAAAUGUAGUCACUUUCAG | 1093 to 1113 | | |
| miR161.1 | Arabidopsis thaliana | At1g63150.1 | CCCCAAUGUUGUUACUUUCAA | 978 to 998 | | |
| miR161.1 | Arabidopsis thaliana | At1g06580.1 | CCCGGAUGUAAUCACUUUCAG | 865 to 885 | | |
| miR161.1 | Arabidopsis thaliana | At1g62860.1 | CCCUGAUGUUGUUACUUUCAG | 441 to 461 | | |
| miR161.1 | Arabidopsis thaliana | At1g62910.1 | UCCAAAUGUAGUCACUUUCAG | 978 to 998 | | |
| miR161.1 | Arabidopsis thaliana | At1g62930.1 | UCCAAAUGUAGUCACUUUCAG | 966 to 986 | | |
| miR161.1 | Arabidopsis thaliana | At1g63080.1 | UCCAAAUGUAGUCACUUUCAA | 921 to 941 | | |
| miR161.1 | Arabidopsis thaliana | At1g63230.1 | UCCGGAUGUAGUCACUUUUAG | 1129 to 1149 | | |

Figure 10B

Table 1

| miRNA / small RNA | species | Accession | complementary site | coordinates | complementary site | coordinates |
|---|---|---|---|---|---|---|
| miR161.1 | Arabidopsis thaliana | At1g63400.1 | UCCAAAUGUAGUCACUUUCAA | 981 to 1001 | | |
| miR161.1 | Arabidopsis thaliana | At1g64580.1 | CCCUGAUGUUGUCACUUUCAC | 738 to 758 | | |
| miR161.1 | Arabidopsis thaliana | At5g16640.1 | CCCUGAUGUAUUUACUUUCAA | 814 to 834 | | |
| miR161.1 | Arabidopsis thaliana | At5g41170.1 | ACCUGAUGUAAUCACUUUCAA | 871 to 891 | | |
| miR161.1 | Arabidopsis thaliana | At1g62670.1 | CCCUGAUGUAUUCACUUUCAG | 969 to 989 | | |
| miR400 | Arabidopsis thaliana | At1g63130.1 | GUGACUUACAAUACUCUCAUA | 1313 to 1333 | | |
| miR400 | Arabidopsis thaliana | At1g06580.1 | GUGACUUAUAAAUACUCUCAUA | 1085 to 1105 | | |
| miR400 | Arabidopsis thaliana | At1g62590.1 | GUUACAUAUAUACUCUCAUA | 1251 to 1271 | | |
| miR400 | Arabidopsis thaliana | At1g62930.1 | GUGACUUACAAUACUCUUAUA | 1186 to 1206 | | |
| miR400 | Arabidopsis thaliana | At1g63330.1 | GAUACAUAUAUACUCUCAUA | 973 to 993 | | |
| miR400 | Arabidopsis thaliana | At1g63400.1 | GUGACUUACAAUACUCUUAUU | 1201 to 1221 | GUACUUACAACACUCUCAUA | 2254 to 2274 |
| miR400 | Arabidopsis thaliana | At1g64580.1 | GUGACAUAUAACACUCUCAUU | 958 to 978 | GUUACUUACAACACUCUCAUA | 2569 to 2589 |
| miR400 | Arabidopsis thaliana | At5g16640.1 | GUAACUUAUAGUAUUCUCAUU | 1034 to 1054 | | |
| miR400 | Arabidopsis thaliana | At5g41170.1 | GUGGCUUAUACUUCACUCAUA | 1091 to 1111 | | |
| miR400 | Arabidopsis thaliana | At1g62670.1 | GUGACUUAUAAAUACGCUUAUA | 1189 to 1209 | | |
| miR168 | Arabidopsis thaliana | At1g48410.1 | UUCCCGAGCUGCAUCAAGCUA | 494 to 513 | | |
| miR393 | Arabidopsis thaliana | At3g62980.1 | GAGACAAUGCGAUCCCUUUGGA | 1710 to 1731 | | |
| miR393 | Arabidopsis thaliana | At4g03190.1 | GAGACCAAUGCGAUCCCUUUGGA | 1586 to 1607 | | |
| miR393 | Arabidopsis thaliana | At3g26810.1 | GAAACAAUGCGAUCCCUUUGGA | 1998 to 2019 | | |
| miR393 | Arabidopsis thaliana | At3g23690.1 | GGUCAGAGCGAUCCCUUUGGCA | 406 to 427 | | |
| miR393 | Arabidopsis thaliana | At1g12820.1 | GAAACAAUGCGAUCCCUUUGGA | 1883 to 1904 | | |
| miR393 | Acorus americanus | CK747866 | AAACAAUGCGAUCCCUUUGGA | 381 to 401 | | |
| miR393 | Ananas comosus | DT335840 | AAACAAUGCGAUCCCUUUGGA | 606 to 626 | | |
| miR393 | Ananas comosus | DT339674 | AAACAAUGCGAUCCCUUUGGA | 249 to 269 | | |
| miR393 | Ananas comosus | DT762218 | AAACAAUGCGAUCCCUUUGGA | 595 to 615 | | |
| miR393 | Aquilegia formosa x Aquilegia pubescens | | | | | |
| miR393 | Brassica rapa subsp. pekinensis | CV434082 | AAACAAUGCGAUCCCUUUGGA | 103 to 123 | | |
| miR393 | Citrus sinensis | CX672154 | AAUCUAUGAGAUCACUUUGGA | 485 to 505 | | |
| miR393 | Coffea arabica | CF588752 | AAACAAUGCGAUCCCUUUGGA | 284 to 304 | | |
| miR393 | Coffea canephora | DV693639 | AAACAAUGCGAUCCCUUUGGA | 594 to 614 | | |
| miR393 | Coffea canephora | DV687246 | AAACAAUGCGAUCCCUUUGGA | 594 to 614 | | |
| miR393 | Coffea canephora | DV693700 | AAACCAAUGCUAUCCCUUUGGA | 138 to 158 | | |
| miR393 | Coffea canephora | DV685434 | AAACAAUGCGAUCCCUUUGGA | 595 to 615 | | |
| miR393 | Coffea canephora | DV686002 | AAACAAUGCGAUCCCUUUGGA | 594 to 614 | | |

Figure 10C

Table 1

| miRNA / small RNA | species | Accession | complementary site | coordinates | complementary site | coordinates |
|---|---|---|---|---|---|---|
| miR393 | Eucalyptus tereticornis | CD668988 | AAACAAUGCGAUCCCUUUGGA | 37 to 57 | | |
| miR393 | Glycine max | BM093129 | AAACAAUGCGAUCCCUUUGGA | 268 to 288 | | |
| miR393 | Glycine max | CA800682 | AAACGAUGCGAUCCCUUUGGA | 331 to 351 | | |
| miR393 | Glycine max | EH257549 | AAACAAUGCGAUCCCUUUGGA | 459 to 479 | | |
| miR393 | Glycine max | BQ454217 | AAACAAUGCGAUCCCUUUGGA | 21 to 41 | | |
| miR393 | Glycine max | BQ611746 | AAACAAUGCGAUCCCUUUGGA | 178 to 198 | | |
| miR393 | Glycine max | BM092058 | AAACAAUGCGAUCCCUUUGGA | 164 to 184 | | |
| miR393 | Glycine max | CA820515 | AAACAAUGCGAUCCCUUUGGA | 438 to 458 | | |
| miR393 | Glycine max | BM178724 | AAACAAUGCGAUCCCUUUGGA | 265 to 285 | | |
| miR393 | Glycine max | BE059679 | AAACAAUGCGAUCCCUUUGGA | 61 to 81 | | |
| miR393 | Glycine max | BM886237 | AAACAAUGCGAUCCCUUUGGA | 529 to 549 | | |
| miR393 | Glycine max | BI973107 | AAACAAUGCGAUCCCUUUGGA | 473 to 493 | | |
| miR393 | Glycine max | EH257731 | AAACAAUGCGAUCCCUUUGGA | 459 to 479 | | |
| miR393 | Glycine max | BM886444 | AAACAAUGCGAUCCCUUUGGA | 173 to 193 | | |
| miR393 | Glycine max | BM093083 | AAACAAUGCGAUCCCUUUGGA | 289 to 309 | | |
| miR393 | Glycine max | BE802766 | AAACAAUGCGAUCCCUUUGGA | 242 to 262 | | |
| miR393 | Glycine max | BM891965 | AAACAAUGCGAUCCCUUUGGA | 386 to 406 | | |
| miR393 | Glycine max | AW620839 | AAACAAUGCGAUCCCUUUGGA | 229 to 249 | | |
| miR393 | Glycine max | BG406518 | AAACAAUGCGAUCCCUUUGGA | 31 to 51 | | |
| miR393 | Glycine max | AW568773 | AAACAAUGCGAUCCCUUUGGA | 433 to 453 | | |
| miR393 | Glycine max | BM524586 | AAACAAUGCGAUCCCUUUGGA | 229 to 249 | | |
| miR393 | Glycine soja | BQ405981 | AAACAAUGCGAUCCCUUUGGA | 9 to 29 | | |
| miR393 | Gossypium arboreum | DW230813 | AAACAAUGCGAUCCCUUUGGA | 709 to 729 | | |
| miR393 | Gossypium hirsutum | DW512794 | AAACAAUGCGAUCCCUUUGGA | 172 to 192 | | |
| miR393 | Gossypium hirsutum | DW500463 | AAACAAUGCGAUCCCUUUGGA | 117 to 137 | | |
| miR393 | Helianthus argophyllus | EE620504 | AGUCAAUGCGAUCCUGUGGA | 526 to 546 | | |
| miR393 | Helianthus argophyllus | EE624548 | AGUCAAUGCGAUCCUGUGGA | 266 to 286 | | |
| miR393 | Helianthus petiolaris | DY937522 | AAUCAAUGAGGUCUCUUGGA | 437 to 457 | | |
| miR393 | Lactuca sativa | BQ873627 | AAUCAAUGAGGUCUCUUGGA | 117 to 137 | | |
| miR393 | Lactuca sativa | BQ852712 | AAUCAAUGCGAUCCCUUUGGA | 540 to 560 | | |
| miR393 | Lotus japonicus | AW428676 | GCACGAGGCGAUCCCUUUGGA | 8 to 28 | | |
| miR393 | Malus x domestica | EB153856 | AAGCAAUGCGAUCCUUUGGA | 517 to 537 | | |
| miR393 | Malus x domestica | CV997902 | AAACAAUGCGAUCCUUUGGA | 152 to 172 | | |
| miR393 | Malus x domestica | CN581823 | AAGCAAUGCGAUCCUUUGGA | 146 to 166 | | |
| miR393 | Malus x domestica | EG999284 | AAGCAAUGCGAUCCUUUGGA | 242 to 262 | | |
| miR393 | Malus x domestica | EB147846 | AAGCAAUGCGAUCCUUUGGA | 403 to 423 | | |

Figure 10D

Table 1

| miRNA / small RNA | species | Accession | complementary site | coordinates | complementary site | coordinates |
|---|---|---|---|---|---|---|
| miR393 | Malus x domestica | CV083662 | AAACAAUGCGAUCCCUUUGGA | 204 to 224 | | |
| miR393 | Malus x domestica | EB153867 | AAGCAAUGCGAUCCCUUUGGA | 517 to 537 | | |
| miR393 | Malus x domestica | CN581521 | AAGCAAUGCGAUCCCUUUGGA | 230 to 250 | | |
| miR393 | Malus x domestica | DR996394 | AAGCAAUGCGAUCCCUUUGGA | 318 to 338 | | |
| miR393 | Malus x domestica | EB117521 | AAACAAUGCGAUCCCUUUGGA | 243 to 263 | | |
| miR393 | Malus x domestica | CN927448 | AAACACUGCGAUCCCUUUGGA | 36 to 56 | | |
| miR393 | Malus x domestica | CV085049 | AAACAAUGCGAUCCCUUUGGA | 204 to 224 | | |
| miR393 | Malus x domestica | EG999285 | AAGCAAUGCGAUCCCUUUGGA | 973 to 993 | | |
| miR393 | Malus x domestica | CO902182 | AAGCAAUGCGAUCCCUUUGGA | 334 to 354 | | |
| miR393 | Malus x domestica | CN901275 | AAACAAUGCGAUCCCUUUGGA | 449 to 469 | | |
| miR393 | Malus x domestica | CO752032 | AAGCAAUGCGAUCCCUUUGGA | 334 to 354 | | |
| miR393 | Malus x domestica | CO416006 | AAACAAUGCGAUCCCUUUGGA | 137 to 157 | | |
| miR393 | Manihot esculenta | DV458227 | AAACAAUGCGAUCCCUUUGGA | 634 to 654 | | |
| miR393 | Medicago truncatula | CX518536 | AAACAAUGCGAUCCCUUUGGA | 412 to 432 | | |
| miR393 | Medicago truncatula | CX520118 | AAGCAAUGCGAUCCCUUUGGA | 375 to 395 | | |
| miR393 | Medicago truncatula | BF648862 | AAACAAUGCGAUCCCUUUGGA | 267 to 287 | | |
| miR393 | Medicago truncatula | DY616088 | AAACAAUGCGAUCCCUUUGGA | 264 to 284 | | |
| miR393 | Medicago truncatula | BF520525 | AAACAAUGCGAUCCCUUUGGA | 386 to 406 | | |
| miR393 | Medicago truncatula | BE204998 | AAACAAUGCGAUCCCUUUGGA | 545 to 565 | | |
| miR393 | Medicago truncatula | BE940827 | AAACAAUGCGAUCCCUUUGGA | 311 to 331 | | |
| miR393 | Picea glauca | CO486443 | AAUCAAUGCGAUCCCUUUGGA | 110 to 130 | | |
| miR393 | Pinus taeda | CO363508 | AAUCAAUGCGAUCCCUUUGGA | 310 to 330 | | |
| miR393 | Pinus taeda | DR089830 | AAUCAAUGCGAUCCCUUUGGA | 61 to 81 | | |
| miR393 | Pinus taeda | DR080283 | AAUCAAUGCGAUCCCUUUGGA | 411 to 431 | | |
| miR393 | Pinus taeda | CO365914 | AAUCAAUGCGAUCCCUUUGGA | 214 to 234 | | |
| miR393 | Pinus taeda | CF478027 | AAACAAUGCGAUCCCUUUGGA | 516 to 536 | | |
| miR393 | Poncirus trifoliata | CX545813 | GAUCAGAGCGAUCCCUUUGAA | 103 to 123 | | |
| miR393 | Populus tremula x Populus tremuloides | BU811329 | AAACAAUGCGAUCCCUUUGGA | 205 to 225 | | |
| miR393 | Populus tremula x Populus tremuloides | BU883972 | AAACAAUGCGAUCCUUUGGA | 299 to 319 | | |
| miR393 | Populus tremula x Populus tremuloides | BI122191 | AAACAAUGCGAUCCCUUUGGA | 150 to 170 | | |
| miR393 | Populus tremuloides | CA924028 | AAACAAUGCGAUCCCUUUGGA | 155 to 175 | | |
| miR393 | Populus trichocarpa | BU874400 | AAACAAUGCGAUCCCUUUGGA | 99 to 119 | | |

Figure 10E

Table 1

| miRNA / small RNA | species | Accession | complementary site | coordinates | complementary site | coordinates |
|---|---|---|---|---|---|---|
| miR393 | Populus trichocarpa x Populus deltoides | CA821121 | AAACAAUGCGAUCCCUUUGGA | 15 to 35 | | |
| miR393 | Populus trichocarpa x Populus deltoides | CN523580 | AAACAAUGCGAUCCCUUUGGA | 305 to 325 | | |
| miR393 | Populus x canadensis | CX186425 | AAACAAUGCGAUCCCUUUGGA | 460 to 480 | | |
| miR393 | Prunus persica | BU048651 | AAUCUAUGAGAUCACUUUGGA | 435 to 455 | | |
| miR393 | Ricinus communis | EG663988 | AAACAAUGCGAUCCCUUUGGA | 448 to 468 | | |
| miR393 | Saruma henryi | DT585400 | AAACAAUGCGAUCCCUUUGGA | 534 to 554 | | |
| miR393 | Zingiber officinale | DY353073 | AAACAAUGCGAUCCCUUUGGA | 410 to 430 | | |
| miR393 | Zingiber officinale | DY353197 | AAACAAUGCGAUCCCUUUGGA | 622 to 642 | | |
| TAS2 3'D6(-) | Arabidopsis thaliana | At1g63130.1 | CAGAUGGUGGAAAUGGGAUAU | 650 to 670 | | |
| TAS2 3'D6(-) | Arabidopsis thaliana | At1g63150.1 | CAAAUGGUCGAAAUGGGAUAU | 535 to 555 | | |
| TAS2 3'D6(-) | Arabidopsis thaliana | At1g62590.1 | CAAAUGGUGGAAAUGGGGUAU | 588 to 608 | | |
| TAS2 3'D6(-) | Arabidopsis thaliana | At1g62910.1 | CAAAUGGUCGAAAUGGGAUAU | 535 to 555 | | |
| TAS2 3'D6(-) | Arabidopsis thaliana | At1g63080.1 | CAGAUGGUGGAAAUGGGAUAU | 478 to 498 | | |
| TAS2 3'D6(-) | Arabidopsis thaliana | At1g63330.1 | CAAAUGGUGGAAAUGGGGUAU | 310 to 330 | | |
| TAS2 3'D6(-) | Arabidopsis thaliana | At1g63400.1 | CAAAUGGUGGAAAUGGGGUAU | 538 to 558 | | |
| TAS2 3'D6(-) | Arabidopsis thaliana | At5g16640.1 | CAAAUGGUGGAAUGGGAUAU | 581 to 601 | | |
| TAS1b 3'D4(-) | Arabidopsis thaliana | At1g63230.1 | GUUGAUCGUAUGGUAGAAGAA | 587 to 607 | | |
| TAS3 5' D7(+) / TAS3 5' D8(+) | Arabidopsis thaliana | At5g60450.1 | AAGGUCUUGCAAGGUCAAGAA | 1874 to 1894 | AGGGUCUUGCAAGGUCAAGAA | 2084 to 2104 |
| TAS3 5' D7(+) / TAS3 5' D8(+) | Arabidopsis thaliana | At2g33860.1 | AGGGUCUUGCAAGGUCAAGAA | 1467 to 1487 | AAGGUCUUGCAAGGUCAAGAA | 1587 to 1607 |

COMPOSITIONS AND METHODS FOR EFFICIENT GENE SILENCING IN PLANTS

CROSS-REFERENCE TO RELATED APPLICATION

This application is a continuation application of U.S. application Ser. No. 11/699,313, filed Jan. 26, 2007, which claims the benefit of the filing date of U.S. Provisional Applications Ser. Nos. 60/762,991, filed Jan. 27, 2006, and 60/856,447, filed Nov. 2, 2006. The entire teachings of the referenced applications are incorporated herein by reference.

GOVERNMENT SUPPORT STATEMENT

The present invention was made with U.S. Government support under contract number R24 GM069512, awarded by the National Institutes of Health. The U.S. Government has certain rights in the invention.

BACKGROUND OF THE INVENTION

During RNA silencing, RNAs of about 21 to 24 nucleotides in length are generated, which are incorporated into a protein complex where they serve as guide RNAs to direct the down-regulation of gene expression at the transcriptional or post-transcriptional level. These small silencing RNAs are called "siRNAs" or "microRNAs", depending upon their biogenesis: endogenous siRNAs derive from long double-stranded RNA and miRNAs derive from local hairpin structures within longer transcripts. RNA silencing occurs in plants, and a better understanding of this process would be useful. In addition, new compositions (e.g., nucleic acid constructs) and methods of achieving RNA-based silencing would be useful, and plants in which expression of one or more genes of interest is modulated, e.g., inhibited, would be of great use.

SUMMARY OF THE INVENTION

This invention relates to compositions and methods for knock-down of a target gene in plants. This invention also relates to methods for silencing endogenous plant genes. It further relates to nucleic acid constructs (DNA, RNA) which comprise a target gene flanked by two complementary sites to a small RNA such as a microRNA (one complementary site is on either side of the target gene, resulting in, for example the configuration: complementary site—target gene—complementary site). In the method, a transgene in which sequence corresponding to the target gene is flanked by two complementary sites (also referred to as flanking regions, or portions thereof) to a small RNA (smRNA), e.g., a microRNA (miRNA) (or smRNAs or miRNAs) expressed in the plant is introduced into the plant, using methods known to those of skill in the art. In certain embodiments the transgene is contained in a nucleic acid construct, which is introduced into the plant or precursor of the plant (e.g., a plant, plant cell, or plant tissue from which the plant is derived), using methods known in the art. At least a portion of the transgene is transcribed to generate an mRNA that in certain embodiments includes (i) a portion that corresponds to the target gene and (ii) at least one complementary site to an smRNA flanking each side of the portion that corresponds to the target gene. The mRNA is cleaved, e.g., within the complementary sites, and converted to a dsRNA corresponding to the target gene. The dsRNA is then cleaved to generate siRNA that mediate silencing of the target gene. As shown in the Examples, the presence of the complementary sites unexpectedly enhances the amount of siRNA produced relative to the level in the absence of the sites, and may in at least some cases be required for siRNA production.

In the construct, smRNAs, to which the flanking regions are complementary can be any smRNAs expressed in the plant in which a target gene is to be knocked down or silenced. In certain embodiments of the invention the complementary sites are complementary to a miRNA expressed in the plant. The two complementary sites need not be completely complementary to the smRNA (e.g., miRNA) expressed in a plant. One or both complementary sites need be only sufficiently complementary to the smRNA (e.g., miRNA) expressed in the plant to have the desired effect in plant cells (e.g. a higher propensity to generate siRNAs than would be evident if only one complementary site were present, such as substantially the same propensity to generate siRNA observed when two completely complementary sites are used). A nucleic acid construct of the present invention can further comprise sequences necessary and/or advantageous for expression of the construct in plant cells (e.g. promoter, enhancer, terminator). The plants in which a target gene can be knocked down or silenced can be any plant, e.g., a plant in which TRANS-ACTING siRNA (TAS) loci have a second miRNA complementary site, such as, but not limited to, flowering plants, e.g., *Arabidopsis*, citrus, maize, soybean, rice, cotton, and other crop plants. In certain embodiments of the invention the plant is an angiosperm, gymnosperms, monocot, dicot, lichen, moss, algae, etc.

In one embodiment, the miRNA is miR390 (found in moss, *A. thaliana*, and a variety of other plants). In this embodiment, the target gene (i.e., sequence corresponding to the target gene) is flanked by two complementary sites to miRNA390 or two sites sufficiently complementary to miR390 that they have substantially the same effect in cells as perfectly complementary sites. (e.g., result in a high propensity of these TAS loci to generate siRNAs).

The invention further relates to compositions and methods for modulating, e.g., inhibiting, expression of a gene of interest in plant cells or plants. The gene of interest may be a target gene of siRNA generated in the plant or plant cell according to an inventive method. Alternately or additionally, the gene of interest may be one whose expression is affected (e.g., inhibited or enhanced) by a target gene of siRNA generated in the plant or plant cell according to an inventive method. The gene of interest may be any gene whose modulation is desired, e.g., whose modulation confers a desirable characteristic or trait of interest on the plant or progeny or product(s) of the plant (e.g., seeds or any material harvested from the plant or utilized by humans or animals for any purpose for which plants are utilized), or whose modulation reduces or lessens an undesirable characteristic or trait.

The invention further relates to plants, plant cells, plant cell lines, seeds, plant tissues (e.g., callus) comprising a nucleic acid construct of the invention. The invention further relates to methods of making such plants.

The invention further relates to methods of generating siRNA in plants, e.g., methods of generating phased siRNA. In one embodiment, siRNA are generated as described herein and harvested from the plant. The invention relates to a method of generating siRNA in a plant wherein two cleavage events occur to a single-stranded RNA precursor, which is subsequently converted to dsRNA, wherein the region of the dsRNA located between the sites at which cleavage occurs are processed by cellular enzyme(s) to generate siRNA.

The invention also provides nucleic acid constructs, e.g., expression vectors, that contain two complementary sites to a small RNA (smRNA), e.g., a microRNA (miRNA) or short interfering RNA (siRNA), wherein the construct does not contain a target gene or nucleic acid sequence derived from a plant or plant pathogen between the complementary sites. The construct may contain one or more restriction sites (e.g., a multiple cloning site) to allow for cloning of a target gene or nucleic acid sequence of interest between the two complementary sites. The construct may contain a coding or non-coding spacer region between the sites. The construct may further comprise regulatory elements, e.g., expression control elements (e.g., promoter, enhancer), terminator appropriately positioned to facilitate expression of an RNA comprising a first and second complementary site flanking a target gene or nucleic acid sequence of interest in a plant. The construct may comprise a selectable or detectable marker.

The invention provides a kit containing any one or more of the inventive constructs, e.g., expression vectors, optionally comprising a nucleic acid sequence targeted to a gene of interest. Optionally the kit contains one or more reagents useful for introducing the construct into a plant, a control construct, instructions for use, etc. In one embodiment the complementary sites are miR390 complementary sites.

This invention offers a variety of advantages compared to existing methods for gene silencing in plants. For example, by exploiting an endogenous pathway for siRNA biogenesis, certain embodiments of the invention provide efficient gene knock-down without the need for unusually high expression of the transgene. In addition, the use of genes and mechanisms occurring naturally in the plant to effect gene silencing, optionally without the introduction of foreign DNA from unrelated species, may reduce regulatory and consumer concerns regarding genetically engineered plants and their products. In certain embodiments, the method is distinct from a variety of other methods known in the art for effecting gene silencing in plants, e.g., the method does not depend on the use of nucleic acid constructs or other synthetic constructs that contain inverted duplications or dual promoters that would give rise to perfect or largely double-stranded RNA. In certain embodiments the construct does not comprise an inverted repeat structure or give rise to such a structure following transcription. In certain embodiments the construct is not transcribed to form a stable hairpin structure upon transcription in a plant cell.

All patents, patent applications, and other publications mentioned herein are incorporated by reference in their entirety. Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001, are standard references of use in certain aspects of the present invention. In the event of a conflict or inconsistency between any of the incorporated references and the instant specification, the specification shall control. In the event of a conflict between two references, the later published one shall control. Standard art-accepted meanings and abbreviations for terms are used herein unless otherwise indicated. Any nucleic acid sequence presented herein may be in DNA or RNA form and may be double- or single-stranded, as appropriate, though only a single strand may be provided herein (one of skill in the art will recognize that the double-stranded form comprises a complementary strand). It will be appreciated that a sequence presented in RNA form will contain "U" residues while the same sequence in DNA form would contain "T" at the positions occupied by "U" in the RNA form of the sequence. It will also be appreciated that a nucleic acid may comprise DNA, RNA, both DNA and RNA, and may contain naturally occurring nucleosides (which term includes ribonucleosides), and/or one or modified nucleosides (wherein the base, sugar, or both may be modified), modified backbones, etc., as recognized in the art. The term "nucleic acid sequence" as used herein refers to the nucleic acid material itself as well as to the information consisting of the specific order of A, G, C, T (or U) residues of the material. "Double stranded nucleic acid" refers to a nucleic acid molecule (e.g., dsRNA), at least a part of which is in Watson-Crick base pairing forming a duplex. As such, the term is to be understood to encompass a nucleic acid molecule that is either fully or only partially double stranded. Exemplary double stranded RNAs include, but are not limited to molecules comprising at least two distinct strands that are either partially or fully duplexed by intermolecular hybridization. Thus both strands will have "ends". Additionally, the term is intended to include a single nucleic acid molecule that by intramolecular hybridization can form a double stranded region (for example, a hairpin).

The compositions and methods of the present invention may be applied, in various embodiments, to organisms that have RNA-dependent RNA polymerase (RDR) homolog(s) such as plants, fungi, and certain invertebrate animals such as nematodes.

BRIEF DESCRIPTION OF THE DRAWINGS

FIGS. 8A-8C show that multiple miRNA and tasiRNA complementary sites correlate with siRNA production from Arabidopsis PPR genes. The normalized number of sequenced small RNAs having their 5' residues at each position along the indicated cDNA is plotted for both the sense (S) and antisense (A/S) strands. Black indicates siRNAs that have only one match to the Arabidopsis genome, while red indicates siRNAs with more than one match to the Arabidopsis genome. The positions corresponding to miR161.1, miR400, TAS 1b 3'D4(-), and TAS2 3'D6(-) complementary sites are indicated by arrows, and alignments of the complementary sites with the small RNAs are shown below. The length distribution of these siRNAs are plotted on the right. Phasing of the siRNAs in 21-nt increments is plotted as in FIG. 1. The numbers and percentages of siRNAs in the most populated register (Max register) are indicated for both the unique (black) and ambiguous (red) siRNAs on the right. The phases predicted by processing of a dsRNA whose terminus is defined by miR161.1, miR400, TAS 1b 3'D4(-) or TAS2 3'D6(-)-mediated cleavage of the mRNA are indicated by a gray circle, and the numbers and percentages of siRNAs that are in register with a cleavage site or in an immediately adjacent register (In phase) are indicated on the right. FIG. 8A discloses SEQ ID NOs: 95, 2, 107, 3, 212, 4, 108, 3, 335, 5, 96, 2, 211, 4, 213, 2, 93, 2, 93, 2, 106 and 3, respectively in order of appearance; FIG. 8B discloses SEQ ID NOs: 210, 4, 99, 2, 218, 5, 100, 2, 212, 4, 110, 3, 212, 4, 111, 3, 99, 2, 102, 2, 279, 3, 112, 3, 336 and 3, respectively, in order of appearance; and FIG. 8C discloses SEQ ID NOs: 217, 4, 113, 3, 103, 2, 104, 2, 114, 3, 105, 2, 115 and 3, respectively, in order of appearance.

FIGS. 10A-10F show Table 1, listing certain miRNAs and siRNAs suitable for use in the present invention (SEQ ID NOs: 35-282, respectively, in order of appearance).

DETAILED DESCRIPTION OF CERTAIN EMBODIMENTS OF THE INVENTION

Figure 1:
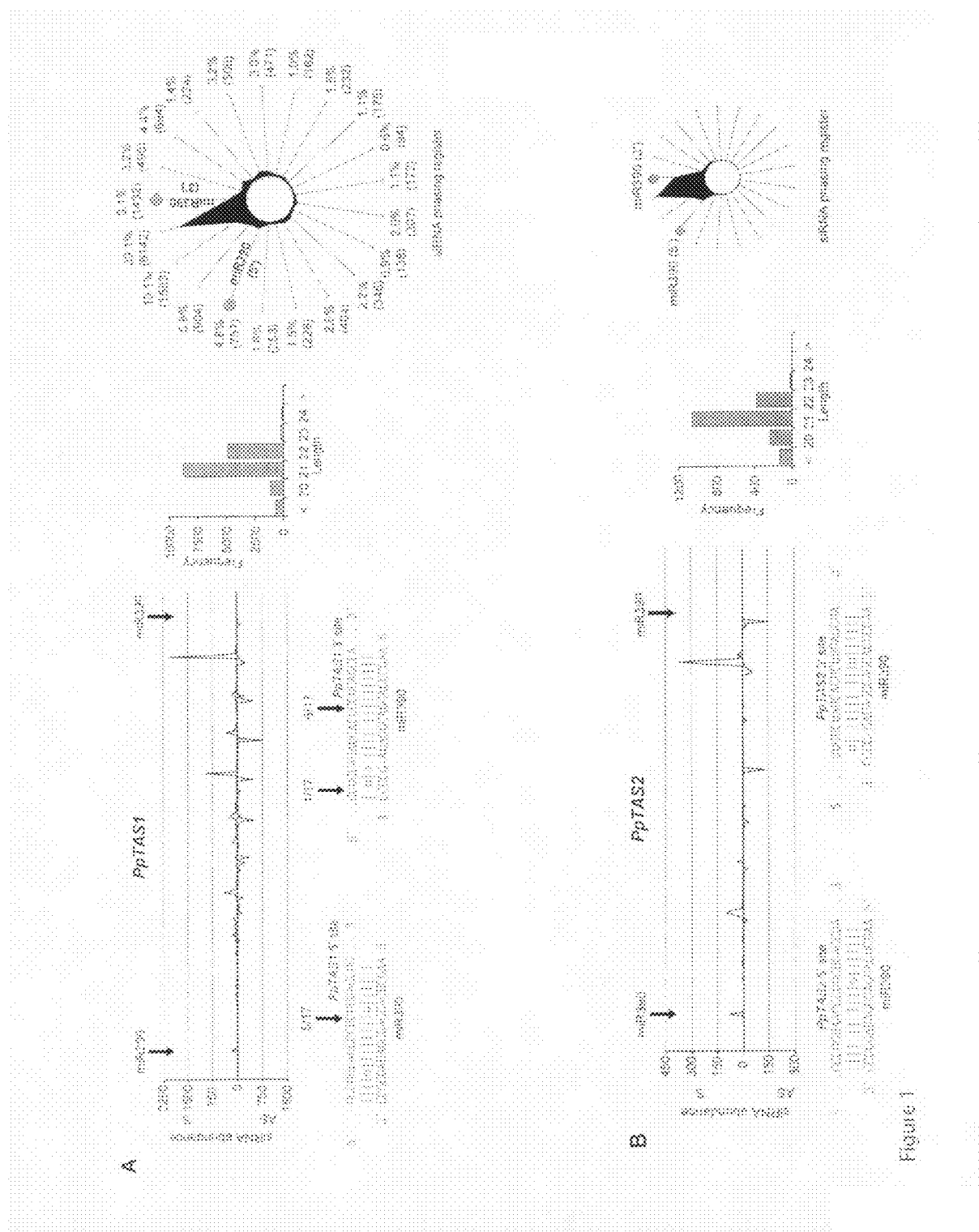
FIG. 1 shows phased *P. patens* siRNAs mapped between miR390 complementary sites. High-resolution graphs are also available (FIG. 7). (A) PpTAS1. The number of sequenced small RNAs (SEQ ID NOs: 283-284, respectively, in order of appearance) with 5' residues at each position along the PpTAS1 locus is plotted for the sense (S) and antisense (AS) strands. The positions corresponding to the miR390 complementary sites (SEQ ID NO: 1) are indicated by arrows, and pairing between the complementary sites and miR390 is shown below. The position of 5' ends mapped by RACE are indicated at the complementary sites by arrows, along with the fraction of sequenced clones mapping to the position. The length distribution and phasing of the small RNAs is plotted on the right. Each spoke of the radial graph represents one of the 21 possible phasing registers, with the total number of small RNAs mapping to that register plotted as distance from the center. The registers proceed clockwise from 5' to 3'. The percentages and total number of sequenced siRNAs from each register are noted. The phasing registers of siRNAs from the antisense strand were corrected to account for the 2-nt, 3' overhangs characteristic of Dicer-like cleavage. The specific registers predicted by 21-nt processing from the 5' and 3' cleavage sites are indicated with gray circles. Thus, phasing of the small RNA populations consistent with cleavage at one or the other site is indicated by abundant siRNAs that are in registers proximal to those predicted by the cleavage sites. For PpTAS1, 11,314 (72%) of the siRNAs were in phase with one of the complementary sites, in that they were in the same register or in immediately adjacent registers as one of these sites. (B) PpTAS2, as in (A) (discloses SEQ ID NOs: 285-286, respectively, in order of appearance and miR390 as SEQ ID NO: 1). The most populated register contained 709 siRNAs (39.1%); 1,648(91%) of the siRNAs fell in the same or adjacent registers as a complementary site. (C) PpTAS3, as in (A) (discloses SEQ ID NOs: 287-288, respectively, in order of appearance and miR390 as SEQ ID NO: 1). The most populated register contained 524 siRNAs (24.3%); 1,097(51%) of the siRNAs fell in the same or adjacent registers as a complementary site. (D) PpTAS4, as in (A) (discloses SEQ ID NOs: 289-290, respectively, in order of appearance and miR390 as SEQ ID NO: 1). The most populated register contained 80 siRNAs (23.3%); 221(64%) of the siRNAs fell in the same or adjacent registers as a complementary site.

Small RNAs (smRNAs) function to modulate, e.g., inhibit, gene expression, and are present in diverse eukaryotic organisms, including plants. As known to those of skill in the art, smRNAs may be defined as low-molecular weight RNAs associated with gene silencing, which may be further described as short (~21 nt) or long (~24-26 nt). Small RNAs include siRNAs and miRNAs, which function in RNA silencing, also sometimes referred to as RNA interference (RNAi). RNA silencing encompasses a broad range of phenomena in which large, double-stranded RNA, fold-back structures, or stem-loop precursors are processed to ~21-26 nucleotide (nt) small RNAs (e.g., siRNAs or miRNAs, which are described further below) that then guide the cleavage of cognate RNAs, block productive translation thereof, or induce methylation of specific target DNAs (Meins, F., et al., Annu Rev. Cell Dev. Biol., 21:297-318, 2005). Additional information relevant to RNA silencing in plants, and small RNAs that mediate RNA silencing, is found in the description below and the references listed herein.

An important step in most modes of RNA silencing is pairing of a smRNA (or a strand thereof) with a portion of a target RNA, e.g., an mRNA transcript. The term "target RNA" or "target sequence" is used herein, e.g., to refer to an RNA whose expression is to be modulated (e.g., inhibited by an RNA silencing mechanism). In certain embodiments of the invention the target RNA is incorporated into a protein complex called the RNA-induced silencing complex (RISC) and cleaved in a sequence-specific manner as directed by an siRNA strand or miRNA that binds to a portion of the target. The cleavage products are then further degraded.

In certain embodiments of the invention the term "target gene" is used to refer to a gene that encodes a target RNA, i.e., a gene from which a target RNA is transcribed. As used herein a "target gene" need not be a full-length gene and need not encode a full length RNA but may instead encode a portion thereof, e.g., a portion of an open reading frame, 5' or 3' untranslated region, exon(s), intron(s), flanking region, etc. The gene may encode an mRNA, tRNA, smRNA, etc. in various embodiments of the invention. The target gene and target transcript are said to be "targeted" by a smRNA that mediates inhibition thereof, e.g., mediates cleavage of the transcript.

The portion of the target RNA with which an siRNA strand (antisense strand) or miRNA pairs may be referred to herein as "complementary site" or a "recognition site" for the smRNA. One of ordinary skill in the art will appreciate that complementarity between an siRNA strand or miRNA and the site with which it pairs need not be, and frequently is not, perfect. In certain embodiments of the invention the degree of complementarity, e.g., percent complementarity, need only be sufficient to provide for stable binding of a smRNA to the complementary site. In certain embodiments of the invention the degree of complementarity need only be sufficient such that the smRNA pairs to the complementary site and mediates cleavage of the target mRNA. For example, in certain embodiments of the invention the degree of complementarity is at least 70%, at least 80%, or at least 90%. In certain embodiments of the invention the number of mismatched or unpaired nucleotides in the siRNA strand or miRNA, following binding to the complementary site, is between 0 and 5, e.g., 1, 2, 3, 4, or 5.

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy of a nucleic acid molecule with its complementary sequence is sufficient to allow the relevant function of the nucleic acid to proceed, in some embodiments, to form a duplex structure under physiological conditions in a plant cell, to mediate ribonuclease activity, etc. For example, the degree of complementarity between the sense and antisense strands of an miRNA precursor can be the same or different from the degree of complementarity between the miRNA-containing strand of an miRNA precursor and the target nucleic acid sequence. Determination of binding free energies for nucleic acid molecules is well known in the art. See e.g., Freier et al., 1986; Turner et al., 1987.

In certain embodiments, the phrase "percent complementarity" refers to the percentage of residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence. It will be appreciated that the nucleic acids may have different lengths and/or that there may be bulges when the two nucleic acids are optimally aligned for maximum complementarity over a given portion of either sequence. Percent complementarity can, in various embodiments of the invention, disregard such bulges in the computation or consider the percentage complementarity to be the number of paired (hydrogen bonded) residues divided by the total number of residues over a given length, which may be the length of the shorter or the longer nucleic acid in different embodiments.

miRNAs are non-protein coding RNAs, generally ranging between about 19 and about 26 nucleotides in length (frequently about 20-24 nucleotides in plants), that guide cleavage in trans of target transcripts. miRNAs negatively regulate the expression of genes involved in a variety of developmental and regulatory pathways. miRNA biogenesis, mechanism, and function are extensively have been extensively reviewed (see, e.g., Bartel, 2004; Chen, X., *FEBS Lett.* 579:5923-5931, 2005; Jones-Rhoades M W, Bartel D P, Bartel B., *Annu Rev Plant Biol.*, 57:19-53, 2006). As noted above, in plants certain miRNAs have been found to guide in-phase processing of dsRNA to form siRNA (see Vasquez, et al., 2004 and Allen et al., 2005). "In phase" refers to the fact that a dsRNA precursor is cleaved at approximately regular intervals, e.g., 21-22 nt, relative to a starting point, which may be the point on the dsRNA where miRNA-mediated (or in some cases siRNA-mediated) cleavage occurs in certain embodiments of the invention, e.g., as described in Allen, 2005, or in U.S. Patent Publication No. 20060174380.

Many miRNA genes (MIR genes) and sequences of the precursor miRNA (pre-miRNA) and mature miRNA and miRNA* that they encode are known in the art. Some of these have been described and made publicly in a searchable online database entitled miRBase (accessible at microrna.sanger-.ac.uk/sequences). See Griffiths-Jones S., et al., *Nucleic Acids Research*, 34, Database Issue, D140-D144, 2006; Griffiths-Jones S., *Nucleic Acids Research*, 32, Database Issue, D109-D111, 2004 for additional information about this database. The following publication provides guidelines on miRNA annotation: "A uniform system for microRNA annotation." Ambros V, et al., RNA, 9(3), 277-279, 2003. Criteria that can be used to identify MIR genes and their encoded products have been developed and applied to computationally identify these molecules in plants (Jones-Rhoades, et al., *Mol. Cell.*, 14(6):787-99, 2004). Additional computation-based approaches are also available. Identifying miRNA may comprise cloning and sequencing small RNA species, identifying sequences that are conserved among multiple species (many miRNA families are conserved across multiple plant species), identifying sequences capable of forming fold-back structures, etc. Additional experimental validation can also be performed, e.g., by knocking out (e.g., deleting all or part of) the candidate MIR gene so as to render it nonfunctional. See the Exemplification for additional information describing how one of skill in the art could identify and/or confirm additional plant miRNAs in a plant species of interest.

A number of plant MIR genes, primary transcripts from these genes (termed pri-miRNAs), precursor RNAs processed from these primary transcripts (termed pre-mRNAs), and mature miRNAs are described in U.S. Patent Application Publications 20050120415, 20050144669, 20060174380, 20060236427, and 20060200878, all of which are incorporated by reference herein. Transcription of MIR genes is probably mediated by RNA polymerase II and gives rise to a primary transcript (pri-miRNA), which undergoes further processing to a shorter precursor mRNA (pre-mRNA). The pre-mRNA can fold to form a self-complementary fold-back structure, (sometimes referred to as a hairpin or "stem-loop" structure) that contains one or more double-stranded (duplex) regions. Typically these duplex regions are imperfect, containing one or more, typically several, mismatches or bulges. In plants, pre-mRNAs are further processed (i.e., cleaved) by DICER-like enzymes to form mature miRNA species. In the cytoplasm, mature miRNAs are incorporated into the RNA-induced silencing complex (RISC), where they pair with and guide cleavage of mRNAs to which they correspond (i.e., that contain a complementary site for the miRNA). In plants, miRNAs often pair with near, though imperfect complementarity to their target mRNA, although lesser degrees of complementarity are sufficient in some cases and are of use in certain embodiments of this invention. As miRNAs are typically about 17-24 nt, and up to 5 mismatches (e.g., 1, 2, 3, 4, or 5 mismatches) are tolerated during naturally occurring miRNA-directed modulation of gene expression, a percent complementarity of at least about 70% between a target RNA and an miRNA should be sufficient for the purposes described herein. Similarly, a percent complementarity of at least about 70% between (i) a complementary site flanking a sequence corresponding to a target gene and (ii) an miRNA should be sufficient for the purposes described herein.

It will be appreciated that microRNAs can be described in terms of RNA (e.g., RNA sequence of a mature miRNA, pre-miRNA, or pri-miRNA), or in terms of DNA (e.g., DNA sequence corresponding to that of a mature miRNA, pre-miRNA, or pri-miRNA), DNA sequence comprising a MIR gene or portion thereof.

Many miRNAs are expressed in a cell-, tissue-, or developmental stage-specific manner. Mutations in miRNA genes result in a variety of developmental and other defects that may affect one or more plant structures in which the miRNA is normally expressed. This specificity of expression is of use in the present invention as described below.

In addition to miRNAs, plants produce diverse sets of endogenous siRNAs. These are typically short (~21-23 nt) smRNAs Like miRNAs, they are incorporated into RISC and guide cleavage of a target transcript to which they correspond (i.e., that contains a complementary site for one strand of the siRNA, typically referred to as the "antisense strand"). In plants, siRNAs are typically generated by cleavage of longer dsRNA molecules mediated by a DICER-like enzyme. One of skill in the art can readily identify numerous plant siRNAs by referring to publicly available databases and the scientific literature, including references herein.

There are multiple ways in which siRNAs can be generated in plants. For instance, during viral infection double-stranded RNA (dsRNA) can be formed, which can be processed into siRNAs that silence the viral mRNAs. If the virus contains sequences that correspond to plant genes, the plant genes can also be silenced during infection in a process known as "virus-induced gene silencing." Alternatively, the dsRNA can be introduced without viral infection by use of long inverted repeats or convergent transcription. Again, the introduced dsRNA is processed into siRNAs, and if these siRNAs correspond to plant genes elsewhere in the genome, they can silence those genes. Another form of gene silencing is called "co-suppression." Here, the messages from the ectopic expression of a transgene are recognized as aberrant and converted into dsRNA by cellular enzymes; the dsRNA, in turn, is processed into siRNAs that silence the transgene as well as endogenous genes with homology to the transgene.

Another class of siRNAs derives from specialized endogenous loci in plants called the TRANS-ACTING siRNA (TAS) genes. The TAS genes are transcribed into an RNA that has an unusual propensity to give rise to siRNAs. One or more of these siRNAs typically corresponds to a protein-coding gene that is otherwise unrelated to the TAS gene, and this trans-acting siRNA (ta-siRNA) directs the cleavage of the mRNA of this protein-coding gene, thereby silencing its expression. The ta-siRNAs are processed in phase, as if they are derived from the sequential cleavage of a dsRNA by a Dicer protein, starting at a defined point and proceeding at ~21-bp intervals. It was recently found that a miRNA directs the cleavage of the TAS transcript and that DICER-LIKE 4 (DCL4) is needed for ta-siRNA accumulation. Thus current models for TAS biogenesis include the following steps: the TAS locus (also referred to as a tasiRNA locus or TAS gene) is transcribed; the TAS transcript is cleaved by miRNA-directed cleavage; and the cleaved product is used as a template for dsRNA synthesis by an RNA-dependent RNA polymerase (RDR6), which is then cleaved by DCL4 into the ta-siRNAs. In these models, the miRNA-directed cleavage is important because it sets the register for the subsequent phased cleavage of the dsRNA by DCL4; if the DCL4 cleavage were in the wrong phase, then the appropriate siRNAs would not be made. However, the miRNA-directed cleavage has not been regarded as sufficient to explain the unusually high propensity of these TAS transcripts to give rise to siRNAs because many other targets of plant miRNAs do not have similarly high propensity to give rise to siRNAs.

As noted above, it has been found that a miRNA directs the cleavage of TAS transcripts and that DICER-LIKE 4 (DCL4) is needed for ta-siRNA accumulation. It has also been found that TAS loci have miRNA complementary sites at which miRNA directed cleavage appears to define one end of the dsRNA intermediate. As described herein, the inventors discovered that some TAS loci have a second miRNA complementary site, the presence/function of which contributes to the phenomenon described: the high propensity of these TAS loci to generate siRNAs. This discovery also provides the basis for new methods for silencing genes in plants, e.g., silencing endogenous plant genes or silencing genes of pathogens (bacterial, viral, fungal, worm, insect in various embodiments of the invention) that may be present (and/or whose mRNA may be present) in one or more cells of a plant. For example, in moss, miR390 directs cleavage of the TAS3a transcript at two sites, ~230 nucleotides apart from each other. Nearly all the ta-siRNAs from TAS3a are derived from this ~230-nt fragment, not from the cleavage fragments more 5' or more 3' of the two sites. A similar phenomenon is observed in *Arabidopsis*, and phylogenetic analysis indicates that the same is true in other flowering plants, including citrus, maize, soybean, rice, cotton, and other crop plants. Without wishing to be bound by any theory, the inventors propose that the dual sites explain why certain TAS loci are such a prolific source of siRNAs when compared to other miRNA targets: they have two sites for miRNA-directed cleavage rather than just one, and the siRNAs are derived from the segment flanked by the two sites. This insight is reflected in the current invention. For efficient and specific knock-down of a target gene in plants, in certain embodiments of the invention, a transgene is introduced in which sequence corresponding to the target gene is flanked by two complementary sites to a miRNA (or miRNAs) expressed in the plant. In another embodiment, a transgene is introduced in which sequence corresponding to the target gene is flanked by two complementary sites to a siRNA (or siRNAs) expressed in the plant.

Thus, the present invention relates to and provides the following, in various embodiments: A method for knock-down (i.e., partial or complete inhibition, reduction, etc., of expression) of a target gene in a plant, comprising introducing into cells of the plant a transgene in which sequence corresponding to the target gene is flanked by two complementary sites to a miRNA or miRNAs expressed in the plant, under conditions appropriate for expression of the nucleic acid construct in cells of the plant. The invention further provides a method for silencing an endogenous plant gene or gene of a plant pathogen, comprising introducing into cells of the plant, or a precursor of the plant, a transgene in which sequence corresponding to the target gene is flanked by two complementary sites to a miRNA or miRNAs expressed in the plant, under conditions appropriate for expression of the nucleic acid construct in cells of the plant. The invention provides either of the above methods, wherein the miRNA is miR390. In any embodiment, the plant can be any plant in which TAS loci have a second miRNA or siRNA complementary site, such as, but not limited to, flowering plants, including *Arabidopsis*, citrus, maize, soybean, rice, cotton, and other crop plants. The invention also relates to and provides the foregoing methods, wherein sequence corresponding to the target gene is flanked by two complementary sites to an siRNA or other small RNA.

The invention further relates to and provides a nucleic acid construct comprising a target gene or nucleic acid sequence that corresponds to a target gene flanked by two complementary sites to a miRNA or siRNA, wherein one complementary site is on each side of the target gene or nucleic acid sequence that corresponds to the target gene. A nucleic acid sequence that "corresponds to a target gene" comprises at least a portion, or "fragment" of the sequence of a target gene or is sufficiently similar in sequence to at least a portion of a target gene such that at least some smRNAs, e.g., at least some siRNAs, derived by cleaving the nucleic acid sequence (in its double-stranded form) would mediate RNA silencing of the gene, e.g., would direct cleavage of a target RNA transcribed from the target gene. For example, the nucleic acid sequence may be substantially identical to a portion of a target gene. Typically the portion of the gene is at least 15 nt in length and may range up to the full length of an RNA transcribed from the gene (optionally such length is the length of the RNA following removal of any introns contained in the primary RNA transcript). In various embodiments of the invention the length of the nucleic acid sequence is between 50 nt and 100 nt, or between 50 nt and 3 kB in length, e.g., between 100 nt and 2 kB, e.g., between 200 nt and 1 kB, e.g., between 200 and 500 nt, between 200 and 400 nt, etc. In various embodiments of the invention the nucleic acid sequence is at least 70%, at least 80%, at least 90%, at least 95%, at least 97%, at least 98%, at least 99%, or 100% identical to the gene or target transcript to which it corresponds over any of the aforementioned lengths, or over a shorter length such as between 15 and 30 nt (e.g., 15, 16, 17, 18, 19, 20, 21, 22, 23, 24, 25, 26, 27, 28, 29, or 30 nt), or between 30 and 50 nt. Thus a nucleic acid sequence is said to correspond to a target gene if between 15 and 30 nt, between 30 and 50 nt, between 50 nt and 100 nt, or between 50 nt and 3 kB in length, e.g., between 100 nt and 2 kB, e.g., between 200 nt and 1 kB, e.g., between 200 and 500 nt, between 200 and 400 nt, etc., of the nucleic acid sequence is at least 70%, at least 80%, at least 90%, at least 95%, at least 97%, at least 98%, at least 99%, or 100% identical to the gene or target transcript transcribed from the gene. In specific embodiments, the nucleic acid sequence differs in sequence from the target gene by up to 1, 5, 10, 20, or 50 nucleotides. Thus a nucleic acid construct of the invention can comprise a target gene or fragment thereof, wherein the fragment is between 15 and 30 nt (e.g., 15, 16, 17, 18, 19, 20, 21, 22, 23, 24, 25, 26, 27, 28, 29, or 30 nt), between 30 and 50 nt, between 50 nt and 100 nt, or between 50 nt and 3 kB in length, e.g., between 100 nt and 2 kB, e.g., between 200 nt and 1 kB, e.g., between 200 and 500 nt, between 200 and 400 nt, in length. The present invention contemplates introducing a second smRNA complementary site, as described herein, into any nucleic acid construct used heretofore in the art for effecting gene silencing by making use of the endogenous mechanism associated with production of phased siRNAs, e.g., any construct described in U.S. Patent Application Publication No. 20060174380, wherein the second complementary site would be located appropriately to enhance production of phased siRNAs. A construct of use for effecting gene silencing by a mechanism involving production of phased siRNAs, wherein the construct contains a first site complementary to a first smRNA and a sequence that corresponds to the target gene, can be modified by inserting a second site complementary to a second smRNA, as follows: If the first site is located 5' to the sequence that corresponds to the target gene, then the second site is located 3' to the sequence that corresponds to the target gene. If the second site is located 5' to the sequence that corresponds to the target gene, then the first site is located 3' to the sequence that corresponds to the target gene.

The nucleic acid sequence may comprise portions that do not correspond to the target gene in addition to one or more portions that do correspond to the target gene. Such portions may be located anywhere within the nucleic acid sequence, e.g., they may be located in the 5' direction or the 3' direction with respect to the portion of the nucleic acid sequence that corresponds to the target gene, or such portions may be located both 5' and 3' from the portion of the nucleic acid sequence that corresponds to the target gene. Thus it will be appreciated that the smRNA complementary sites need not be immediately adjacent to (i.e., contiguous with) a portion of the nucleic acid sequence that corresponds to the target gene but may instead be separated from such portion(s) by an intervening spacer region. Thus "flanked by" as used herein, does not require that the smRNA complementary sites are contiguous with a portion of the nucleic acid sequence that corresponds to a target gene. All that is necessary is that there is a smRNA complementary site on each side of a portion of the nucleic acid sequence corresponding to the target gene. Either or both smRNA complementary sites may, in various embodiments of the invention, be located contiguously with a portion of the nucleic acid sequence that corresponds to the target gene. In certain embodiments either or both smRNA complementary sites may, in various embodiments of the invention, be separated from a portion of the nucleic acid sequence that corresponds to the target gene by between 1 nt and 2 kB, e.g., between 1 nt and 1 kB, between 1 nt and 500 nt, between 1 nt and 250 nt, between 1 nt and 100 nt, etc. In certain embodiments either or both smRNA complementary sites are separated from a portion of the nucleic acid sequence that corresponds to the target gene by between 10 and 20 nt, between 10 and 50 nt, or between 10 and 100 nt. Thus the spacer between either smRNA complementary site and the closest nucleotide that corresponds to a portion of a target gene may, in various embodiments of the invention, be between 1 nt and 2 kB, e.g., between 1 nt and 1 kB, between 1 nt and 500 nt, between 1 nt and 250 nt, between 1 nt and 100 nt, between 10 and 20 nt, between 10 and 50 nt, or between 10 and 100 nt in length. The size of the spacer on either side can be selected from any of these ranges.

The nucleic acid sequence may contain multiple discrete portions that correspond to the target gene, separated by portions that do not correspond to the target gene. Such portions optionally correspond to a second, third, or fourth target gene. It will be appreciated that the portions that correspond to the target gene may have different lengths, different degrees of sequence identity to the target gene, and may correspond to regions located anywhere within the target gene.

In certain embodiments the nucleic acid sequence comprises multiple copies of a sequence that efficiently effects siRNA-directed cleavage of a target transcript. The sequence may, for example, be one that has been demonstrated in vitro or within living cells or organisms, to function efficiently as an siRNA or portion thereof. Such multiple copies may be located contiguously or interspersed with other sequences that either do or do not correspond to the target gene. The nucleic acid sequence may contain, for example, between 2 and 100, between 5 and 50, between 10 and 20 copies of such a sequence. The nucleic acid sequence may contain multiple copies, e.g., between 2 and 100, between 5 and 50, between 10 and 20 copies of any smRNA sequence known in the art, e.g., an smRNA (e.g., siRNA) sequence known in the art to efficiently direct cleavage of a target transcript. Cleavage of the nucleic acid sequence (in its double-stranded form) by a DICER-like enzyme (e.g., DCL4) may result, in various embodiments of the invention, in production of between 1 and 200 smRNAs (e.g., siRNAs) capable of directing cleavage of a target transcript. In certain embodiments of the invention between 1 and 50, between 2 and 20, or between 5 and 10 such smRNAs are produced.

One of skill in the art will be able to perform sequence comparisons to determine percent identity. In such comparisons, typically one sequence acts as a reference sequence to which test sequences are compared. When using a sequence comparison algorithm, test and reference sequences may be input into a computer, subsequence coordinates are designated if necessary, and sequence algorithm program parameters are designated or default parameters are used. The sequence comparison algorithm then calculates the percent sequence identity for the test sequence(s) relative to the reference sequence, based on the designated program parameters.

Optimal alignment of sequences for comparison can be conducted, for example, by the local homology algorithm described in Smith & Waterman, 1981, by the homology alignment algorithm described in Needleman & Wunsch, 1970, by the search for similarity method described in Pearson & Lipman, 1988, by computerized implementations of these algorithms (GAP, BESTFIT, FASTA, and TFASTA in the GCG® WISCONSIN PACKAGE®, available from Accelrys, Inc., San Diego, Calif., United States of America), or by visual inspection. See generally, Ausubel et al., supra.

One example of an algorithm that is suitable for determining percent sequence identity and sequence similarity is the BLAST algorithm, which is described in Karlin and Altschul (Karlin and Altschul, Proc. Natl. Acad. Sci. USA 87:22264-2268, 1990; see also Altschul, et al., J. Mol. Biol. 215:403-410, 1990) and modified as in Karlin and Altschul, Proc. Natl. Acad. Sci. USA 90:5873-5877, 1993 is incorporated into the NBLAST and XBLAST programs. Additional algorithms are available to generate alignments and provide percent identity between a sequence of interest and sequences in any of a variety of public databases. Software for performing BLAST analyses is publicly available through the National Center for Biotechnology Information via the World Wide Web. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. In one embodiment, the BLASTN program (for nucleotide sequences) uses as default a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix.

In one embodiment, the percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions may be to be rounded to the nearest whole number. In one embodiment, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs are used. A PAM250 or BLOSUM62 matrix may be used. See the National Center for Biotechnology Information (NCBI) Web site for these programs. In a specific embodiment, percent identity of a sequence of interest and a second sequence is calculated using BLAST2 with default parameters. It will be appreciated that similar methods may be used to determine percent complementarity.

The term "substantially identical", in the context of two nucleotide sequences, refers to two or more sequences or subsequences that have in some embodiments at least about 70% nucleotide identity, in some embodiments at least about 75% nucleotide identity, in some embodiments at least about 80% nucleotide identity, in some embodiments at least about 85% nucleotide identity, in some embodiments at least about 90% nucleotide identity, in some embodiments at least about 95% nucleotide identity, in some embodiments at least about 97% nucleotide identity, and in some embodiments at least about 99% nucleotide identity, when compared and aligned for maximum correspondence, as measured using one of the above-mentioned sequence comparison algorithms or by visual inspection.

In specific embodiments of the nucleic acid construct, and of the invention more generally, the target gene is a plant gene. The plant gene can be, for example, a gene of a flowering plant, such as *Arabidopsis*, citrus, maize, soybean, rice, cotton, or other crop plant. In other embodiments the target gene is a viral gene, e.g., a gene of a plant virus such as a viral plant pathogen. In other embodiments the target gene is a gene of any intracellular plant pathogen or non-pathogenic organism that infests a plant but may not necessarily be pathogenic.

Expression or activity of the gene of interest can be modulated (e.g., its expression can be increased or decreased) using the present invention. Thus the gene of interest may, but need not be, a direct target of siRNA produced according to the inventive methods. The gene of interest may be one whose expression is positively or negatively regulated by an expression product of a target gene, or one that encodes an expression product (mRNA, protein) whose modification, transport, processing, or activity, is positively or negatively regulated by, or otherwise interacts with, an expression product of a target gene, or that encodes an expression product that physically interacts with an expression product of a target gene. The term "modulate" refers to an increase, decrease, or other alteration of any, or all, chemical and biological activities or properties of a biochemical entity. For example, the term "modulate" can refer to causing a change in the expression level of a gene or a level of a non protein-coding RNA molecule (e.g., a tRNA, smRNA, rRNA) or an RNA molecule that encodes one or more proteins or protein subunits; or to causing a change in an activity of one or more proteins or protein subunits that is upregulated or downregulated, such that expression, level, or activity is greater than or less than that observed in the absence of such modulation. In certain embodiments the term "modulate" can mean "inhibit" or "suppress", but its use is not limited to this definition. "Modulating activity of a gene" encompasses modulating the activity of a gene product (RNA, polypeptide) encoded thereby.

As used herein, the terms "inhibit", "suppress", "down regulate", "knock down", "silence", and grammatical variants thereof are used interchangeably and, in certain embodiments of the invention, refer to an activity whereby gene expression or a level of an RNA encoding one or more gene products is reduced below that observed in the absence of a nucleic acid of the present invention. In some embodiments, inhibition results in a decrease in the steady state expression level of a target RNA. In some embodiments, inhibition results in an expression level of a target gene that is below that level observed in the absence of a nucleic acid of the invention. In some embodiments, inhibition of gene expression with a nucleic acid of the presently invention is greater in the presence of the molecule than in its absence. In some embodiments, inhibition of gene expression is associated with an enhanced rate of degradation of an RNA encoded by the target gene. In various embodiments a method of the invention inhibits expression of an RNA in a plant cell or plant by at least 30%, 40%, 50%, 60%, 70%, 80%, 90%, 95%, or 98% as compared with a suitable control. A suitable control is, e.g., the same or a similar plant cell or plant in the same or similar environment wherein the control cell or plant does not contain a nucleic acid of the invention that inhibits expression of the gene in a process triggered by dual smRNA-mediated cleavage events. In various embodiments a method of the invention results in knockout of expression, where in some embodiments "knockout" refers to inhibition such that the RNA is undetectable using an art-accepted detection method such as reverse-transcription PCR or, in some embodiments, if detectable, its level is reduced by at least 98%, or at least 99%.

The invention provides a method of inhibiting expression of a target gene in a plant comprising steps of: (a) expressing a single-stranded RNA in the plant, wherein the single-stranded RNA comprises a nucleic acid sequence that corresponds to a target gene and wherein the single-stranded nucleic acid or a template for transcription thereof was introduced into the plant or an ancestor of the plant, such as a plant or plant cell from which the plant was generated, by the hand of man; and (b) maintaining the plant under conditions in which (i) the single-stranded RNA is cleaved at locations flanking the nucleic acid sequence; (ii) the resulting RNA is transcribed to double-stranded RNA (dsRNA); and (iii) the double-stranded RNA is cleaved to form shorter dsRNA that inhibit expression of the target gene, thereby inhibiting expression of the target gene in the plant. The invention provides a method of producing siRNA comprising expressing an RNA comprising a nucleic acid sequence that corresponds to a target gene, wherein the nucleic acid sequence is flanked by two complementary sites to a smRNA, in a plant or plant cell. The siRNA produced according to the method may direct cleavage of a target transcript. The invention further provides a method of inducing cleavage of a target transcript in a cell comprising expressing a dsRNA that comprises recognition sites for an smRNA flanking a nucleic acid sequence that corresponds to the target transcript in the cell. The invention further provides a method of inducing cleavage of at least a portion of a dsRNA at intervals of approximately 20-26 nt, e.g., approximately 20, 21, 22, 23, 24, 25, or 26 nt, in a cell comprising expressing a dsRNA that comprises recognition sites for an smRNA flanking a portion of the dsRNA in the cell. In certain embodiments the cleavage produces siRNAs. In certain embodiments the dsRNA is produced by expressing a single-stranded RNA that is converted to dsRNA by an RNA-dependent RNA polymerase, e.g., RDR6.

The invention encompasses any method in which a dsRNA is cleaved at smRNA recognition sites on both sides of a portion of the dsRNA, and wherein the resulting portion between the sites of cleavage is subsequently cleaved to form siRNA or, in certain embodiments of the invention other smRNA. The siRNA may then inhibit expression of a target gene. The invention encompasses any method in which a dsRNA is bound by an smRNA at recognition sites on both sides of a portion of the dsRNA, and wherein the resulting portion between the recognition sites of cleavage is subsequently cleaved to form siRNA. The siRNA may then inhibit expression of a target gene. The invention encompasses any method of producing the dsRNA, e.g., by introducing into a cell (or plant) a construct encoding a ssRNA that is then converted into double-stranded form by an endogenous RNA-dependent RNA polymerase.

While it is expected that the methods of the invention will be of particular use in living plant cells (either isolated, e.g., maintained in culture, or within organisms), the invention encompasses embodiments in which the methods are practiced in vitro, i.e., outside of a living cell. The methods may be practiced using a cell lysate or purified or partially purified components (such as RDR6, DCL4, RISC proteins, etc.) and, optionally, an appropriate energy source.

It will be appreciated that in the practice of certain methods of the invention, dsRNA is produced from ssRNA in vitro or within a living cell by an RNA-dependent RNA polymerase (RDR). In certain embodiments of the invention the RDR is RDR6. The RDR6 may be endogenous to a plant in which dsRNA is produced. The RDR6 may be an ortholog of *Arabidopsis* RDR6. It will also be appreciated that in the practice of certain methods of the invention, dsRNA is cleaved in vitro or within a living cell by a DICER-like enzyme (DCL). In certain embodiments of the invention the DCL is DCL4. The DCL4 may be endogenous to a plant in which dsRNA is cleaved. The DCL4 may be an ortholog of *Arabidopsis* DCL4. "*Arabidopsis*" as used herein may refer to *A. thaliana*, e.g., commonly used laboratory strains, thereof or other *Arabidopsis* species in various embodiments of the invention. Reference sequences are found in GenBank for a variety of RDR6 and DCL4 sequences from various organisms, and other public databases contain, e.g., *A. thaliana* and other plant sequences. Information and accession numbers for certain genes and their encoded products (mRNA, proteins) of interest herein may be found in Genbank under the Gene ID. *A. thaliana* DCL4 has locus designation AT5G20320 according to conventional nomenclature and has Gene ID 832154 (mRNA and protein accession numbers NM_122039; NP_197532). *A. thaliana* RDR6 has locus designation AT3G49500 according to conventional nomenclature and has Gene ID 824112 (mRNA and protein accession numbers NM_114810; NP_190519). It will be appreciated that useful sequences may vary from these exemplary sequences, e.g., within different members of a population. The invention encompasses such variants, e.g., strain variants, polymorphic variants within a strain, etc. It will also be appreciated that sequences sufficiently identical to one of these sequences may also be used provided they retain sufficient functionality. For example, substantially identical sequences could be used.

The invention provides nucleic acid constructs that are of use in the methods and are of use to make transgenic plants, plant cells, plant cell lines, etc. The invention provides a nucleic acid construct comprising a nucleic acid sequence corresponding to a target gene, wherein the nucleic acid sequence is flanked by two complementary sites to a smRNA, wherein a first complementary site is located upstream from (in the 5' direction from) the nucleic acid sequence corresponding to the target gene, and the second complementary site is located downstream from (in the 3' direction from) the nucleic acid sequence corresponding to the target gene. Nucleic acids produced by transcription of all or a portion of the construct (whether produced in vitro or in living cells, e.g., within plants) are an aspect of this invention.

The invention provides a nucleic acid construct comprising: (a) nucleic acid that can be transcribed to form a single-stranded RNA (ssRNA) flanked by recognition sites for an smRNA or smRNAs. The ssRNA may further be transcribed to form a dsRNA. The recognition sites may be identical or different and may be recognized by the same or different smRNAs, which may be miRNA or siRNA, or both, in any combination. The invention provides transgenic plants and plant cells having the nucleic acid construct integrated into the genome of at least some of their cells, transgenic seeds having the construct integrated into their genome. The seeds may be obtained from the transgenic plant.

In certain embodiments of the invention expression of the smRNA does not occur throughout the plant. In certain embodiments of the invention expression of the smRNA does not occur under all environmental conditions. For example, synthesis of the smRNA may occur under conditions of stress, upon infection by a pathogen, etc. Presence of two or more complementary sites for miRNAs that are expressed in a restricted manner in an RNA that is to be cleaved to form siRNA will result in inhibition of target gene expression only in those portions of the plant, or those developmental stages, in which the miRNA is expressed. Thus a nucleic acid construct or transgenic plant of the present invention can comprise a nucleic acid sequence corresponding to a target gene, wherein the nucleic acid sequence is flanked by two complementary sites to a smRNA, wherein the smRNA complementary sites are complementary to a smRNA that is expressed in a cell-, tissue-, or developmental stage-specific (e.g., temporal) manner. In certain embodiments of the invention the smRNA is a miRNA. The present invention thus provides a method of modulating, e.g., inhibiting, expression of a gene of interest in a cell-, tissue-, or developmental stage-specific or environmental condition-specific manner. The diversity of specific modulation achievable using the present invention matches the diversity of expression patterns of endogenous smRNA and the diversity of conditions under which endogenous smRNA is naturally expressed. Certain cell or tissue types and developmental stages of interest are described in further detail below. One of skill in the art will be able to identify a smRNA expressed in one or more cell, tissues, or developmental stages or conditions of interest. Where such smRNA is not already known in the publicly available databases or literature, one of skill in the art could use experimental and/or computational methods to identify such an smRNA.

The invention also contemplates engineering plants that ectopically (optionally inducibly or repressibly) express a smRNA in a desired cell type, tissue, or developmental stage or under particular environmental or other conditions, to achieve cell-, tissue-, or developmental stage-specific modulation of gene expression. In some embodiments, promoters for expressing the smRNA are chosen that direct tissue-, cell-type-, or stage-specific expression of the smRNAs. Optionally inducible or repressible promoters are used so that expression of the smRNA (and thus production of siRNAs that direct cleavage of a target transcript) can be controlled by modulating environmental conditions, etc. In some embodiments, the promoter is responsive to infection of a plant by a pathogen or pest, such that production of siRNAs targeted to a pest or pathogen gene occurs upon infection.

In some embodiments, the stable expression of the smRNA in the plant (either naturally or as a result of engineered expression using an appropriate promoter) occurs in a location or tissue selected from the group consisting of epidermis, root, vascular tissue, xylem, meristem, cambium, cortex, pith, leaf, flower, seed, and combinations thereof. In certain embodiments the expression occurs in one or more organs of the plant (e.g., ovary), or portions of a flower.

Figure 6:
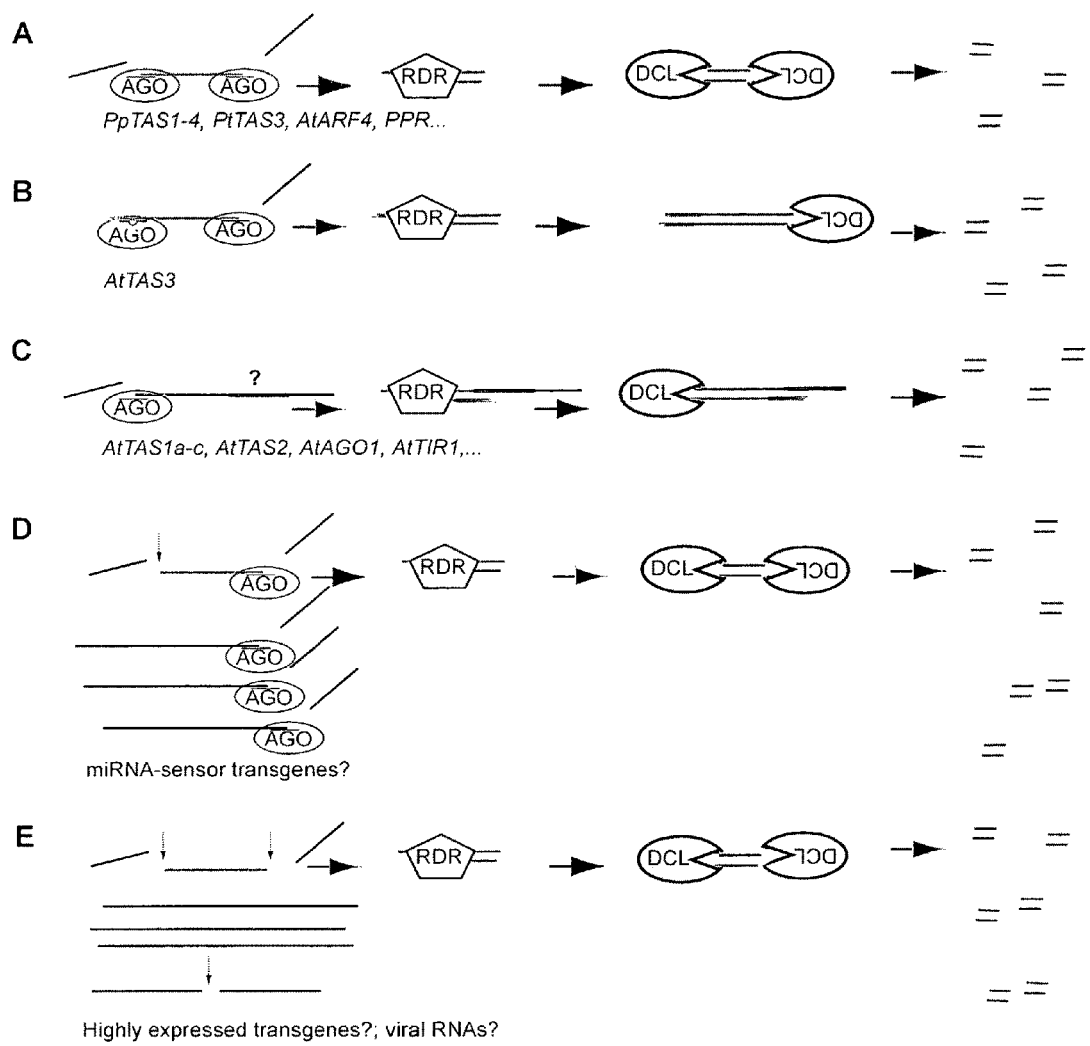
FIG. 6 shows different embodiments of the two-hit model for siRNA biogenesis in plants, as well as schematic examples of the technology. (A) The internal product of dual miRNA- or siRNA-directed cleavage is recognized as a substrate for RdRp activity, which produces a dsRNA with two well-defined ends, as for PpTAS1-4, PtTAS3, AtARF4, and many PPR genes. Subsequent processing by a DCL enzyme produces populations of siRNAs in phase with one or the other end. Replacement of a portion of the RNA shown in red on the left side of the figure (horizontal line extending between the two elements labeled "AGO1") with RNA corresponding to a gene of interest (while retaining dual miRNA- or siRNA-complementary sites flanking the RNA corresponding to the gene of interest) will result in production of siRNAs capable of silencing that gene in a process triggered by dual miRNA or siRNA binding and subsequent dual miRNA- or siRNA-mediated cleavage events. RNA species resulting from subsequent processing steps are shown in red as horizontal lines extending from the element labeled "RDR", as horizontal lines extending between the two elements labeled "DCL", and as short double lines that represent siRNAs (right side of figure) that silence the gene of interest. (B) The segment of an RNA flanked by miRNA complementary sites, only one of which is competent for AGO1-catalyzed cleavage, defines an RdRp substrate, as in AtTAS3. Subsequent DCL processing of this dsRNA proceeds chiefly from the terminus defined by the miRNA-mediated cleavage. Replacement of a portion of the RNA shown in red on the left side of the figure (horizontal line extending between the two elements labeled "AGO1") with RNA corresponding to a gene of interest (while retaining dual miRNA- or siRNA-complementary sites) will result in production of siRNAs capable of silencing that gene in a process triggered by dual miRNA or siRNA binding events and subsequent miRNA- or siRNA-mediated cleavage within the region complementary to one of the miRNAs or siRNAs. RNA species resulting from subsequent processing steps are shown in red as horizontal lines extending from the element labeled "RDR", as horizontal lines extending from the element labeled "DCL", and as short double lines that represent siRNAs (right side of figure) that silence the gene of interest. (C) The segment of RNA defined on the 5' by miRNA-directed cleavage and on the 3' by an unknown element (question mark) that helps recruit RdRp activity gives rise to dsRNA, as in AtTAS1a-c, AtTAS2, and a limited number of other miRNA targets (FIG. 9). Subsequent DCL processing of the dsRNA proceeds chiefly from the terminus defined by the miRNA-mediated cleavage. (D) The segment of a very abundant RNA defined on the 5' by a very rare, random cleavage event and on the 3' by miRNA-directed cleavage becomes recognized as an RdRp substrate, as might be triggering silencing of miRNA-sensor transgenes in plants. (E) The segment of a very abundant RNA defined by two rare, random cleavage events becomes recognized as a substrate for RdRp activity, as might be triggering transgene and virus silencing.

FIGS. 6A and 6B schematically illustrate the endogenous silencing pathway involving dual miRNA- or siRNA-mediated binding described herein and may be referred to explain how certain methods of the invention harness this pathway to inhibit expression of a gene of interest. The RNA shown in red on the left side of FIGS. 6A and 6B (horizontal line extending between the two elements labeled "AGO") includes dual smRNA complementary sites. In certain embodiments of the inventive method of knocking down gene expression, replacement of a portion of this RNA located between the dual complementary sites with RNA corresponding to a gene of interest results in production of siRNAs capable of silencing the gene of interest by a process involving, e.g., triggered by, dual smRNA (e.g., miRNA or siRNA) binding and subsequent dual smRNA- (e.g., miRNA- or siRNA-) mediated cleavage events. RNA species resulting from subsequent processing steps are shown in red as horizontal lines extending from the element labeled "RDR", as horizontal lines extending between the two elements labeled "DCL", and as short double lines that represent siRNAs (right side of figure). These siRNAs mediate silencing of the gene of interest. In the embodiment shown in FIG. 6A, both smRNA complementary sites are competent to direct cleavage. In the embodiment shown in FIG. 6B, only one of the smRNA complementary sites is competent to direct cleavage. Without wishing to be bound by any theory, in at least some plant species the smRNA, e.g., miRNA, may be bound by an AGO1 protein, which may catalyze cleavage of the RNA. Notably, in both of these examples, the process of gene silencing is in some embodiments initiated by a miRNA, miR390, which is naturally expressed within many crop plants.

Thus the presence in a plant cell of a nucleic acid of the invention (e.g., a DNA construct) that is transcribed to yield an RNA such as that shown at the left in FIG. 6A or 6B, wherein the red area contains dual smRNA complementary sites and a portion that corresponds to a gene of interest (target gene), will result in production of siRNAs capable of silencing that gene. The RNA on the left in FIG. 6A or 6B that includes complementary sites to a smRNA, is a target RNA for the smRNA, which binds to the complementary sites and mediates cleavage within at least one of the complementary sites. The siRNAs shown on the right, which are generated from the portion of the RNA that corresponds to a gene of interest (after conversion to double-stranded form), will then mediate cleavage of a distinct target RNA transcribed from the gene of interest (target gene).

It will thus be appreciated that the terms "target RNA", "target sequence", "target", and "target gene" are used in various ways herein and in the art. For example, the terms "target", "target RNA", or "target sequence" can refer to a nucleic acid with which an smRNA interacts (i.e., to which it binds) in a sequence-specific manner leading, in some instances, to cleavage of the resulting duplex structure. Such terms can refer to only that portion of a nucleic acid with which the smRNA interacts to form a duplex structure or can refer to a longer nucleic acid that comprises such a portion (i.e., the longer nucleic acid is considered a target of the smRNA although the smRNA directly interacts with only a portion of the smRNA to which it is complementary). For example, "target", "target sequence", or "target RNA" can refer to an miRNA complementary site or to an ssRNA comprising an miRNA complementary site. As described above, in certain embodiments of the present invention a miRNA binds to and mediates cleavage of an ssRNA target containing such complementary sites, which is subsequently converted to dsRNA. The dsRNA is then cleaved to generate siRNAs, which interact with, and mediate cleavage, of their own target(s). "Target", "target sequence" or "target RNA" thus can also refer to an RNA whose cleavage is mediated by siRNA produced by cleavage of a dsRNA generated from a ssRNA precursor as described herein. Such terms as "target" and "target gene" can refer to a gene of interest whose inhibition is desired, which inhibition is mediated by siRNA generated in accordance with the inventive methods. Such terms can also refer herein to the "sequence corresponding to a target gene", i.e., the sequence that is flanked by complementary sites to a smRNA in the nucleic acid constructs of the invention. The various senses in which the afore-mentioned terms are used herein will be evident from the context to one of skill in the art.

smRNA Complementary Sites

Any complementary site for a smRNA may be used in various embodiments of the present invention. The site may be complementary to an miRNA or siRNA. The site may be perfectly (100%) complementary or may have imperfect complementarity as described herein and known in the art. The complementary site may be one that is naturally found in a TAS locus or tasiRNA precursor RNA, flanking the portion of the RNA that is cleaved to produce tasiRNAs. The complementary site may be any smRNA complementary site that is found on one side of a nucleic acid sequence that is cleaved to produce siRNA, wherein a second smRNA complementary site is found on the other side of the nucleic acid sequence. In various embodiments of the invention the complementary site is recognized by a smRNA selected from the group consisting of:

miR390:
(SEQ ID NO: 1)
AAGCUCAGGAGGGAUAGCGCC;

miR161.1:
(SEQ ID NO: 2)
UUGAAAGUGACUACAUCGGGG;

miR400:
(SEQ ID NO: 3)
UAUGAGAGUAUUAUAAGUCAC;

TAS2 3'D6(-):
(SEQ ID NO: 4)
AUAUCCCAUUUCUACCAUCUG;

TAS1b 3'D4(-):
(SEQ ID NO: 5)
UUCUUCUACCAUCCUAUCAAU;

TAS3 5'D7(+):
(SEQ ID NO: 6)
UUCUUGACCUUGUAAGACCCC;

TAS3 5'D8(+):
(SEQ ID NO: 7)
UUCUUGACCUUGUAAGGCCUU;

miR168:
(SEQ ID NO: 8)
UCGCUUGGUGCAGGUCGGGAA;
and miR393:
(SEQ ID NO: 9)
UCCAAAGGGAUCGCAUUGAUC.

In one embodiment, the miRNA is UUCGCUUGCAGAGAGAAAUCAC (SEQ ID NO: 10). Note that these sequences may have been identified in one or more plants, e.g., *Arabidopsis*, most land plants, moss, etc. It will be appreciated that in some cases the sequences are conserved across multiple species while in other cases there could be minor variations. Such variations are encompassed within the present invention. See also Table 1, listing certain miRNAs and siRNAs suitable for use in the present invention. It will be appreciated that homologous siRNAs or miRNAs from other plant species than those listed could be used. Optionally, recognition of the complementary site by the cognate miRNA or siRNA leads to cleavage. One of skill in the art could determine whether binding and/or cleavage of a smRNA to a candidate complementary site occurs in vivo (in living cells or organisms) or in vitro, e.g., under conditions approximating physiological intercellular conditions.

A number of complementary sites of use in the present invention are listed in Table 1. These complementary sites were found flanking regions that are cleaved to form siRNA in plants and thus in some cases represent dual complementary sites (in some cases a third site was found). Accession numbers of the gene that contains the complementary sites, and the coordinates of the complementary sites, are also provided. The accession numbers are either Genbank accession numbers or, in the case of *A. thaliana*, use the art-accepted nomenclature for *A. thaliana* genes. One of skill in the art will recognize that the complementary sites for any particular siRNA or miRNA can be determined by one of skill in the art and may be varied without detrimentally affecting the ability of the siRNA or miRNA to direct cleavage. Table 1 represents a variety of different degrees of complementarity between the miRNA or siRNA and its complementary site. Artificially created complementary sites are also of use. These could resemble naturally occurring complementary sites (e.g., they may be at least 70%, 80%, 90%, 95%, identical to a naturally occurring site. In some embodiments, an artificial smRNA is used (see, e.g., Niu, Q-W., et al., "Expression of artificial microRNAs in transgenic *A. thaliana* confers virus resistance", *Nat. Biotechnol.*, online publication Oct. 26, 2006). An appropriate complementary site for the artificial smRNA is employed.

The length of the complementary site could vary. The length of a complementary site may be defined as equal to the length of the smRNA that binds to it, but it will be appreciated that a complementary site could differ in length from that of the smRNA, e.g., it may be shorter than the length of the smRNA. Typically the complementary site is sufficiently long such that the smRNA can bind to the site with reasonable specificity and, optionally, direct cleavage within a duplex structure formed upon binding. Such cleavage may occur at a position within the duplex typical of cleavage directed by smRNAs, e.g., in certain embodiments at position 10 or 111 of the smRNA). For example, a complementary site could be between 15 and 24 nucleotides in length, or any intervening number, wherein there are 1, 2, 3, 4, or 5 mismatches when the smRNA is paired with the complementary site in the case of a 15 nucleotide site and up to 6, 7, or 8 mismatches in the case of a 24 nucleotide complementary site. Similar considerations would apply for other smRNA complementary sites. It will be appreciated that there may be "bulges" in the duplex formed when an smRNA pairs with its complementary site. In such instances a bulge could be considered equivalent to a single mismatch or, in various embodiments of the invention a bulge of X nucleotides could be considered equivalent to X mismatches. It will also be appreciated that the specificity of binding of the smRNA to the complementary site need not be completely specific, e.g., the smRNA may bind to different sites having either a lesser or greater degree of complementarity.

The first and second complementary sites are between 15 and 30 nt, between 18 and 24 nt, between 20 and 22, or exactly 21 nt in length in various embodiments of the invention, or any intervening range or specific value within the foregoing ranges in certain embodiments of the invention. In certain non-limiting embodiments of the invention the number of mismatched or unpaired nucleotides in the siRNA strand or miRNA, following binding to the complementary site, is between 0 and 5, e.g., 1, 2, 3, 4, or 5. In certain non-limiting embodiments of the invention the number of mismatched or unpaired nucleotides (including those in both strands) in a duplex structure formed between the smRNA and its complementary site, is between 0 and 10, e.g., 1, 2, 3, 4, 5, 6, 7, 8, 9, or 10. The mismatches or bulges may occur at any position within the duplex structure, in various embodiments of the invention. In certain embodiments the mismatches or bulges are located at positions known in the art not to typically inhibit or prevent smRNA-directed cleavage. In other embodiments the mismatches or bulges are located at such positions. One or more mismatches or bulges may occur, for example, at any position with respect to the 5' end of a smRNA depicted in the figures herein or contemplated when an smRNA described herein pairs with a site complementary to it. The mismatch may be any mismatch known in the art. Certain mismatches are described in the Exemplification. In certain embodiments a mismatch is said to occur when a nucleotide within an at least partly double-stranded structure is not paired in a conventional G-C, A-T, or A-U base pair. In certain embodiments a mismatch is said to occur when a nucleotide in an at least partly double-stranded structure is not paired in a Watson-Crick base pair. It will be appreciated that the afore-mentioned mismatches may exclude "bulges", wherein a nucleotide bulges outward from an otherwise duplex region by being located between two nucleotides that are base paired with adjacent nucleotides on the opposite strand of the duplex.

The portion of the smRNA that is complementary to the complementary site could vary. For example, in certain embodiments the complementary site is at least 70%, at least 80%, or at least 90% complementary to the first 16 nucleotides of the smRNA. In certain embodiments the complementary site is at least 70%, at least 80%, or at least 90% complementary to the first 17, 18, or 19 nucleotides of the smRNA. In certain embodiments the complementary site is a subsequence of a complementary site listed in Table 1, wherein said subsequence is at least 16, 17, 18, 19, 20, or 21 nucleotides in length. In some embodiments the subsequence is the last 16, 17, 18, 19, 20, or 21 nucleotides of the listed sequence. In some embodiments the subsequence is at least 70%, at least 80%, at least 90%, or 100% complementary to the first 16, 17, 18, 19, 20, or 21 nucleotides of an smRNA.

A smRNA complementary site may be in the form of DNA or RNA. For example, when the smRNA complementary site is present in a DNA vector, it will typically be in the form of DNA, whereas when it is present in a single or double-stranded RNA, it will be in the form of RNA.

Nucleic Acid Constructs

The invention provides a variety of nucleic acid constructs. The term "construct" as used herein denotes the fact that the nucleic acid material is recombinant, i.e., it contains portions of nucleic acid material that are not found joined to one another in nature in the same configuration as in the construct, and/or that the nucleic acid has been produced by the hand of man. A nucleic acid is considered to be recombinant and/or produced by the hand of man notwithstanding the fact that it may have undergone one or more rounds of replication (e.g., DNA or RNA replication), amplification, transcription, reverse transcription) either in vitro or in a living cell or organism subsequent to its initial construction.

The construct may be an isolated nucleic acid. Any portion of the construct, e.g., an smRNA complementary site, or a fragment of a target gene, may be isolated. As used herein, the term "isolated" refers in certain embodiments to a molecule substantially free of other nucleic acids, proteins, lipids, carbohydrates, and/or other materials with which it is normally associated, such association being either in cellular material or in a synthesis medium. Thus, the term "isolated nucleic acid" refers to a ribonucleic acid molecule or a deoxyribonucleic acid molecule (for example, a genomic DNA, cDNA, miRNA, siRNA, etc.) of natural or synthetic origin or some combination thereof, which (1) is not associated with the cell in which the "isolated nucleic acid" is found in nature, or (2) is operatively linked to a polynucleotide to which it is not linked in nature, (3) has been modified or generated by the hand of man; or (4) does not occur in nature. Similarly, the term "isolated polypeptide" refers to a polypeptide, in some embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature. The term "isolated", when used in the context of an "isolated cell", refers to a cell that has been removed from its natural environment, for example, as a part of an organ, tissue, or organism or has been generated in culture. Any of the cells of the present invention can be "isolated". Where nucleic acid sequences are disclosed herein, the complement of these sequences are also intended to be specifically disclosed.

A first isolated nucleic acid may be inserted into or joined to second nucleic acid, or multiple (e.g., third, fourth, fifth, etc.) nucleic acids, to form the construct, e.g., using standard recombinant nucleic acid technology (See, e.g., Ausubel, supra, and Sambrook, supra). The second, third, fourth, fifth, etc., nucleic acid may be one(s) that are not found joined to the first nucleic acid in nature. Any two or more nucleic acids that are joined to form the construct may come from different species or be separated from one another, e.g., by at least 1, 2, 5, or 10 kB, in the genome of a single species and/or present in opposite orientation. The construct may be linear or circular and may be single or double-stranded in various embodiments of the invention. The construct may be present in vitro or within a cell or organism, where it may be integrated into the genome.

Any of a wide variety of constructs that can be introduced into and stably expressed in plants are of use in the present invention. One of skill in the art will be familiar with such constructs and methods of their manufacture and manipulation. The construct can be, e.g., an *Agrobacterium*-based construct, a viral construct or one that contains viral elements (e.g., from a DNA or RNA plant virus), etc. The construct may comprise a sequence having the configuration: 5'-complementary site—target gene or target gene fragment—complementary site-3'. The construct may comprise a sequence having the configuration: 5'-complementary site-nucleic acid sequence-complementary site-3'. This portion of the construct may be operably linked to a promoter, such that it is transcribed, e.g., in a 5'→3' direction.

The construct can be an expression vector comprising suitable regulatory elements (e.g., expression control elements such as a promoter element) to direct expression of a nucleic acid sequence in a plant. The expression vector may be used to introduce a nucleic acid sequence flanked by smRNA complementary sites into a cell and direct expression of the nucleic acid sequence therein (optionally after integration into the genome). The expression vector may be used to introduce a smRNA into a cell and direct expression of the smRNA therein, optionally after integration into the genome). The expression vector may contain multiple "expression cassettes", each comprising a promoter and an operatively linked nucleic acid sequence to be expressed in a plant or plant cell. In certain embodiments a single promoter drives transcription of multiple transcripts. The construct can contain 1, 2, 3, or more nucleic acid sequences that correspond to a single target gene or to different target genes. The construct can comprise a nucleic acid sequence that corresponds to a target gene and is flanked by complementary sites to a smRNA and may also comprise sequence that encodes the smRNA or a precursor thereof. Many suitable plant expression vectors are known in the art and can be modified for purposes of the present invention.

The construct can comprise a suitable promoter for expression of an operatively linked nucleic acid sequence in a plant or plant cell. The promoter can be constitutive or non-constitutive, e.g., inducible, repressible, cell-, tissue-, or stage-specific. Non-constitutive promoters suitable for use with the nucleic acid constructs of the invention include spatially specific promoters, temporally specific promoters, and inducible or repressible promoters. Where transcription of the construct is to occur in a plant cell, spatially specific promoters can include organelle-, cell-, tissue-, or organ-specific promoters functional in a plant (e.g., a plastid-specific, a root-specific, a pollen-specific, or a seed-specific promoter for directing transcription in plastids, roots, pollen, or seeds, respectively). Inducible promoters may be induced by chemicals (e.g., exogenous or synthetic chemicals as well as endogenous pheromones and other signaling molecules, pathogen-specific molecules) or by environmental conditions such as, but not limited to, biotic or abiotic stress (e.g., water deficit or drought, heat, cold, high or low nutrient or salt levels, high or low light levels, crowding, or pest or pathogen infection). See, e.g., Padidam, Curr Opin Plant Biol., 6(2):169-77, 2003, for discussion of chemically regulated gene expression in plants. Promoters may be generally constitutively expressed but at differing degrees or "strengths" of expression, e.g., promoters commonly regarded as "strong promoters" or as "weak promoters". Promoters of use in the present invention are RNA polymerase I, II, or III promoters active in plants in various embodiments of the invention. In many embodiments an RNA polymerase II promoter is used.

Temporal or developmental stage-specific promoters can include promoters that tend to promote expression during certain developmental stages in an animal or plant's growth or reproductive cycle, or during different times of day or night, or at different seasons in a year. Plant developmental stages are known in the art. A useful resource for descriptions of such stages is the Plant Ontology Consortium™ which provides, inter alia, plant structure development stages, including flower development stages, fruit development stages, inflorescence development stages, leaf development stages, root development stages, seed development stages (See the Plant Ontology Consortium website). The Plant Structure Developmental Stage Ontology describes developmental stages of organs and organ systems of a 'generic' flowering plant. Series of developmental stages are defined based on temporal landmarks delineated by morphological and anatomical changes, as described in published literature for several species, namely (but not limited to) *Arabidopsis*, maize and rice. Information regarding these stages for flowers and floral organs may be obtained from the following references and the afore-mentioned web site: Anther and pollen development stages may be based on the descriptions for *Arabidopsis* (Sanders, P M, Bui, AQ., Weterings, K, McIntire, KN, Hsu, Y-C, Lee, PY, Truong, MT, Beals, TP, and Goldberg RB. (1999) Anther developmental defects in *Arabidopsis thaliana* male-sterile mutants. Sex. Plant. Reprod. 11, 1-27. Regan, SM, Moffatt BA. (1990) Cytochemical analysis of pollen development in wild-type *Arabidopsis* and a male-sterile mutant. Plant Cell 2: 877-889), and for maize (Bedinger P and Russell SD (1994) Gametogenesis in maize. In The Maize Handbook, M. Freeling and V. Walbot, eds (New York: Springer-Verlag), pp. 48-60. The main four stages of leaf development may be based on description by Poethig (Poethig S. (1997) Leaf morphogenesis. Plant Cell, 9: 1077-1087), and on description of leaf development stages in rice (Itoh J, Nonomura K, Ikeda K, Yamaki S, Inukai Y, Yamagishi H, Kitano H, Nagato Y. (2005) Rice Plant Development: from Zygote to Spikelet. Plant Cell Physiol, 46:23-47.). "Leaf development stages" (1 leaf initiation stage, 2 leaf expansion stage, 3 leaf fully expanded, and 4 leaf senescence stage) are pertinent for simple leaf and compound leaf, encompassing eudicots and monocots. Five generic stages of root development may be defined (1 root primordium formation, 2 root meristem formation, 3 establishment of tissue systems, 4 root elongation, 5 root hair formation) e.g., based on descriptions for cereal root development (Hochholdinger F, Park W J, Sauer M, Woll K. (2004) From weeds to crops: genetic analysis of root development in cereals. Trends Plant Sci., 9: 42-48), and for *Arabidopsis* lateral root development (Casimiro I, Beeckman T, Graham N, Bhalerao R, Zhang H, Casero P, Sandberg G, Bennett M J. (2003) Dissecting *Arabidopsis* lateral root development. Trends Plant Sci, 8:165-171.). Stages of embryo development may be defined based on classic studies of model plant species (*Arabidopsis* and *Capsella*), reviewed by West and Harada (West MAL, Harada JJ. (1993) Embryogenesis in Higher Plants: An Overview. Plant Cell, 5: 1361-1369), and in cereal crops, maize (Abbe, E C, Stein, OL. (1954) The growth of the shoot apex in maize: embryogeny. American J Bot, 41: 285-293; Sheridan W F, Clark JK. (1987) Maize embryogeny: a promising experimental system. Trends Genet, 3: 3-6) and rice (Itoh et al, 2005) in particular. Endosperm development stages may be defined based on descriptions of free-nuclear endosperm development in *Arabidopsis* and cereals (Olsen OA, Linnestad C, Nichols S E. (1999) Developmental biology of the cereal endosperm. Trends Plant Sci, 4: 253-257; Olsen OA. (2004) Nuclear endosperm development in cereals and *Arabidopsis thaliana*. Plant Cell, 16: S214-227.), also taking into consideration endosperm patterning in both persistent and transient endosperms (Costa LM, Gutierrez-Marcos JF, Dickinson HG. (2004) More than a yolk: the short life and complex times of the plant endosperm. Trends Plant Sci, 9: 507-514).

It will be appreciated that nomenclature used in the art for various stages may vary for different plants.

Typically a promoter is selected to provide functionality in a cell or plant to be transformed with a nucleic acid construct comprising the promoter, e.g., a nucleic acid construct of the invention. The promoter could be an endogenous plant promoter, a plant virus promoter, etc. Non-limiting specific examples include an opaline synthase promoter isolated from T-DNA of *Agrobacterium*, and a cauliflower mosaic virus 35S promoter, among others, as well as enhanced promoter elements or chimeric promoter elements, e.g., an enhanced cauliflower mosaic virus (CaMV) 35S promoter linked to an enhancer element (an intron from heat shock protein 70 of *Zea mays*). Many expression-specific promoters functional in plants and useful in the method of the invention are known in the art. For example, U.S. Pat. Nos. 5,837,848; 6,437,217 and 6,426,446 disclose root specific promoters; U.S. Pat. No. 6,433,252 discloses a maize L3 oleosin promoter; U.S. Patent Application Publication 20040216189 discloses a promoter for a plant nuclear gene encoding a plastid-localized aldolase; U.S. Pat. No. 6,084,089 discloses cold-inducible promoters; U.S. Pat. No. 6,140,078 discloses salt inducible promoters; U.S. Pat. No. 6,294,714 discloses light-inducible promoters; U.S. Pat. No. 6,252,138 discloses pathogen-inducible promoters; and U.S. Patent Application Publication 2004/0123347 al. discloses water deficit-inducible promoters. The promoter element can include nucleic acid sequences that are not naturally occurring promoters or promoter elements or homologues thereof but that can regulate expression of a gene. Exemplary constitutive promoters are derived from the CaMV 35S, rice actin, and maize ubiquitin genes, each described in U.S. Patent Application Publication 20060236427. Exemplary inducible promoters for this purpose include the chemically inducible PR-1a promoter and a wound-inducible promoter, also described in the afore-mentioned publication. Selected promoters can direct expression in specific cell types (such as leaf epidermal cells, mesophyll cells, root cortex cells) or in specific tissues or organs (roots, leaves or flowers, for example). Exemplary tissue-specific promoters include well-characterized root-, pith-, and leaf-specific promoters, each described in the afore-mentioned publication.

In some embodiments, the nucleic acid construct includes both a promoter element and a functional terminator element. The construct may include a functional polyadenylation signal and polyadenylation site, e.g., to facilitate RNA transcribed from the construct (optionally after integration into the genome) to be polyadenylated and processed for transport into the cytoplasm. A variety of other elements known in the art may be included in the construct. For example, the construct may comprise a detectable or selectable marker, typically operatively associated with a promoter. In some embodiments the marker encodes a detectable or selectable polypeptide, e.g., one that confers resistance to a chemical agent, one that confers a visible phenotypic characteristic on the transformed cell or plant, a colored or fluorescent protein, etc.

A variety of transcriptional terminators are available for use in the constructs. These are responsible for the termination of transcription beyond the transgene and its correct polyadenylation. Appropriate transcriptional terminators are those that are known to function in plants and include the CaMV .sup.35S terminator, the tml terminator, the nopaline synthase terminator, and the pea rbcS E9 terminator. RNA polymerase III terminators often comprise a run of 5 or more consecutive thymidine residues. In some embodiments, an RNA polymerase III terminator comprises the sequence TTTTTTT. These can be used in both monocotyledons and dicotyledons. Numerous sequences have been found to enhance the expression of an operatively linked nucleic acid sequence, and these sequences can be used in conjunction with the nucleic acids of the invention to increase expression in transgenic plants. Various intron sequences have been shown to enhance expression, particularly in monocotyledonous cells. For example, the introns of the maize AdhI gene, e.g., Intron 1, or the intron from the maize bronze1 ge may be used to enhance expression. Intron sequences have been routinely incorporated into plant transformation vectors, often within the non-translated leader. A number of non-translated leader sequences derived from viruses are also known to enhance expression, e.g., leader sequences from Tobacco Mosaic Virus (TMV, the "W-sequence"), Maize Chlorotic Mottle Virus (MCMV), and Alfalfa Mosaic Virus (AMV).

Suitable methods for plant transformation for use with the current invention are believed to include virtually any method by which nucleic acids, e.g., DNA, can be introduced into a cell, such as by direct delivery of nucleic such as by PEG-mediated transformation of protoplasts (Omirulleh et al., 1993), by desiccation/inhibition-mediated DNA uptake (Potrykus et al., 1985), by electroporation (U.S. Pat. No. 5,384,253), by agitation with silicon carbide fibers (U.S. Pat. Nos. 5,302,523; 5,464,765), by *Agrobacterium*-mediated transformation (U.S. Pat. Nos. 5,591,616 and 5,563,055) and by acceleration of nucleic acid coated particles (U.S. Pat. Nos. 5,550,318; 5,538,877; and 5,538,880), floral dipping, etc. See U.S. Patent Publication No. 20030028927 for references to the scientific literature describing examples of these techniques applied to various plant species and components, e.g., promoter elements, useful in nucleic acid constructs to be introduced into plants. Through the application of techniques such as these, virtually any plant species may be stably transformed, in various embodiments of the invention, and these cells developed into transgenic plants.

Where one wishes to introduce nucleic acids by means of electroporation, certain cell wall-degrading enzymes, such as pectin-degrading enzymes, may be employed to render the target recipient cells more susceptible to transformation by electroporation than untreated cells. Alternatively, recipient cells are made more susceptible to transformation by mechanical wounding. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize, wheat, tomato, soybean, and tobacco.

One also may employ protoplasts for electroporation transformation of plants. For example, the generation of transgenic soybean plants by electroporation of cotyledon-derived protoplasts is described in Intl. Patent Appl. Publ. No. WO 9217598. Other examples of species for which protoplast transformation has been described include barley, sorghum, maize, wheat, and tomato.

Microprojectile bombardment is a useful method for delivering transforming nucleic acid constructs to plant cells in accordance with the invention (U.S. Pat. Nos. 5,550,318; 5,538,880; 5,610,042; and PCT Application WO 94/09699). In this method, particles may be coated with nucleic acids and delivered into cells by a propelling force. Exemplary particles include those comprised of tungsten, platinum, or gold. Other embodiments utilize various organic polymers. It is contemplated that in some instances precipitation onto metal particles would not be necessary for nucleic delivery to a recipient cell using microprojectile bombardment. However, it is contemplated that particles may contain nucleic acid in addition to, or instead of, being coated with it. For the bombardment, cells in suspension may be concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering nucleic acids into plant cells by acceleration is the Biolistics Particle Delivery System, which can be used to propel particles coated with nucleic acids or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples of species for which have been transformed by microprojectile bombardment include monocot species such as maize (PCT Application WO 95/06128), barley, wheat (U.S. Pat. No. 5,563,055), rice, oat, rye, sugarcane, and sorghum, as well as a number of dicots including tobacco, soybean (U.S. Pat. No. 5,322,783), sunflower, peanut, cotton, tomato, and legumes in general (U.S. Pat. No. 5,563,055).

*Agrobacterium*-mediated transfer is a widely applicable system for introducing genes into plant cells because, for example, the DNA can be introduced into whole plant tissues, thereby bypassing the need for regeneration of an intact plant from a protoplast. The use of *Agrobacterium*-mediated plant integrating vectors to introduce DNA into plant cells is well known in the art. As a genus, *Agrobacteria* can transfer DNA to a large and diverse set of plant types including numerous dicot and monocot angiosperm species and gymnosperms (See, See, for example, U.S. Pat. No. 5,563,055 and Gelvin, S. B., "*Agrobacterium*-Mediated Plant Transformation: the Biology behind the "Gene-Jockeying" Tool", Microbiology and Molecular Biology Reviews, 67(1): 16-37 (2003) and references therein, all of which are incorporated herein by reference). The molecular basis of genetic transformation of plant cells is transfer from the bacterium and integration into the plant nuclear genome of a region of a large tumor-inducing (Ti) or rhizogenic (R1) plasmid that resides within various Agrobacterial species. This region is referred to as the T-region when present in the plasmid and as T-DNA when excised from the plasmid. Generally, a single-stranded T-DNA molecule is transferred to the plant cell in naturally occurring Agrobacterial infection and is ultimately incorporated (in double-stranded form) into the genome. Systems based on Ti plasmids are widely used for introduction of foreign genetic material into plants and for production of transgenic plants. It will be appreciated that these plasmids have been extensively modified and elements therefrom have been utilized in the construction of improved plasmid systems. All such systems are envisioned as being of use in the present invention.

*Agrobacterium*-mediated transformation is efficient in dicotyledonous plants and is used in various embodiments of the invention for transformation of dicots, including *Arabidopsis*, tobacco, tomato, and potato. *Agrobacterium*-mediated transformation has been routinely used with dicotyledonous plants for a number of years and has more recently become applicable to monocotyledonous plants. Advances in *Agrobacterium*-mediated transformation techniques have now made the technique applicable to nearly all monocotyledonous plants. For example, *Agrobacterium*-mediated transformation techniques been applied to rice (U.S. Pat. No. 5,591,616) wheat, barley, maize, and a number of other monocots. See, e.g., procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. No. 5,591,616 (maize); U.S. Pat. No. 5,981,840 (maize); U.S. Pat. No. 5,463,174 (brassicas). Similar methods have been reported for, among others, peanut (Cheng et al. (1996) Plant Cell Rep., 15: 653); asparagus (Bytebier et al. (1987) Proc. Natl. Acad. Sci. U.S.A., 84:5345); barley (Wan and Lemaux (1994) Plant Physiol., 104:37); rice (Toriyama et al. (1988) Bio/Technology, 6:10; Zhang et al. (1988) Plant Cell Rep., 7:379; wheat (Vasil et al. (1992) Bio/Technology, 10:667; Becker et al. (1994) Plant J., 5:299), and alfalfa (Masoud et al. (1996) Transgen. Res., 5:313). *Agrobacterium* transformation vectors are typically capable of replication in *E. coli* as well as *Agrobacterium*, allowing for convenient manipulations as described. *Agrobacterium* containing both armed and disarmed Ti genes can be used for the transformations. In one embodiment of the invention, the transgenic plant cell of the invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, U.S. Pat. No. 5,159,135; De Framond (1983) Biotechnology, 1:262-269; and Hoekema et al., (1983) Nature, 303:179. In such a binary system, the smaller plasmid, containing the T-DNA border or borders, can be conveniently constructed and manipulated in a suitable alternative host, such as *E. coli*, and then transferred into *Agrobacterium*. In one embodiment, the pGreen vector system is used (Hellens, et al., Plant Mol. Biol., 42(6):819-32, 2000).

Transformation of plant protoplasts can be achieved using methods based on calcium phosphate precipitation, polyethylene glycol treatment, electroporation, and combinations of these treatments. Following transformation, a plant is regenerated from the protoplast. Illustrative methods for the regeneration of a number of different plants from protoplasts are known in the art. Examples include rice, barley, maize, sorghum, etc.

Additional methods of introducing nucleic acids into intact cells or tissues can be utilized. For example, regeneration of cereals from immature embryos or explants can be effected as described.

Viral vectors are of use to transform plants and plant cells. Plant viral vector technology has advanced significantly in recent years. See, e.g., Gleba, Y., et al., *Curr Opin Plant Biol.*, 7(2):182-8, 2004. Any of a wide variety of viral vectors can be used. The viral vector could be derived from a DNA or RNA plant virus or a viroid. The virus could be single or double stranded. Viral vectors may be based on viruses such as members of the Bromoviridae (e.g., bromoviruses, alfamoviruses, ilarviruses) and Tobamoviridae (e.g., tobacco mosaic virus). Other useful viruses include cauliflower mosaic virus, geminiviruses, etc. The vector could be an RNA transcript comprising a viral promoter element. The vector may comprise one or more viral promoter elements functional in a plant, e.g., a coat protein or movement protein promoter. Viral vectors can be introduced into plants in a variety of different ways including a number of the above-described methods. Abrasion, dipping, magnification, etc., can be used. In one embodiment the viral vector is contained in an *Agrobacterium*.

Multiple constructs can be introduced into a plant cell or plant (optionally into different portions of the plant). Thus the transgenic plant cells or transgenic plants of the invention can be obtained by use of any appropriate transient or stable, integrative or non-intergrative transformation method described herein or known in the art. The nucleic acid constructs can be transcribed in any plant cell or tissue or in a whole plant of any developmental stage.

Marker genes may be used to provide an efficient system for identification of those cells that are stably transformed by receiving and integrating a transgenic nucleic acid construct into their genomes. Useful marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant nucleic acid. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047. Screenable markers or reporters, such as markers that provide an ability to visually identify transformants can also be employed. Non-limiting examples of useful screenable markers include, for example, a gene expressing a protein that produces a detectable color by acting on a chromogenic substrate (e.g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

The plant may be generated using marker-independent transformation such that a selectable marker used in the course of introducing the construct into cells has been lost or otherwise eliminated. In certain embodiments the plant does not contain any nucleic acid sequences introduced by the hand of man that are not naturally found in the plant. Marker-independent, also called "marker-free" transformation methods include (i) co-transformation with a selectable marker and a construct of interest, selection for transformants, followed by identification or selection of transformants that have segregated or otherwise lost the marker; (ii) excision of the marker using a site-specific recombination system such as the Cre/Lox or flp/frt system; (iii) use of the MAT vector system, etc. See, e.g., Ballester, A., et al. Plant Cell Rep. 2006, Khan, R. S., et al., Plant Cell Rep., 25(9):914-9, 2006; Zuo, J., et al., *Curr Opin Biotechnol.*, 13(2):173-80, 2002; de Vetten, et al., *Nat. Biotechnol.*, 21(4):439-42, 2003.

The invention provides transgenic seeds comprising a construct of the invention. Seeds of transgenic, fertile plants can be harvested. If desired, these seeds may be used to grow progeny generations, including hybrid generations, of transgenic plants of this invention that include the construct in their genome. Transgenic plants of the invention can therefore be prepared by direct transformation of a plant with a nucleic acid construct or by crossing a first plant having the construct with a second plant lacking the construct. For example, the construct can be introduced into a plant line that can be transformed to produce a transgenic plant, which can be crossed with a second plant line to introgress the recombinant DNA into the resulting progeny. A transgenic plant of the invention with one construct (such as one that effects altered expression of a target gene) can be crossed with a plant line having one or more genes or transgenes that confers one or more additional trait(s) (e.g., herbicide resistance, pest or disease resistance, environmental stress resistance, modified nutrient content, and yield improvement) to produce progeny plants having the construct that confers the desired modulation of expression of a gene of interest and the additional trait(s).

Standard methods of plant breeding are of use in the present invention. For example, crossing can include the following steps (a) plant seeds of the first parent plant (e.g., non-transgenic or a transgenic) and a second parent plant that is transgenic according to the invention; (b) grow the seeds of the first and second parent plants into plants that bear flowers; (c) pollinate a flower from the first parent with pollen from the second parent; and (d) harvest seeds produced on the parent plant bearing the fertilized flower. In certain embodiments a selected construct can be moved from one line into an entirely different line without the need for further recombinant manipulation. One can thus produce inbred plants which are true breeding for one or more constructs. Different inbred plants can be crossed, e.g., to produce hybrids with different combinations of DNA constructs. In one embodiment a first construct directs expression of a transgene and a second construct directs expression of a nucleic acid sequence that corresponds to the transgene flanked by smRNA complementary sites, wherein the smRNA is one that is expressed in a cell-, tissue-, developmental stage-specific manner. Genetic markers can be used to assist in the introgression of one or more constructs of the invention from one genetic background into another.

The invention also provides a transgenic plant grown from the transgenic seed of the invention. This invention provides transgenic plants grown directly from transgenic seed containing a construct of the invention as well as progeny generations of plants, including inbred or hybrid plant lines. In certain embodiments such lines are created by crossing a transgenic plant grown directly from transgenic seed to a second plant not grown from the same transgenic seed.

The invention provides transgenic plant cell lines, e.g., clonal cell lines derived from a single plant cell, that contain or express a nucleic acid of the invention. The plant cell line could be derived from any of a variety of plant cell types, e.g., leaf, root, stem, etc.

The invention further provides transgenic root lines, that contain or express a nucleic acid of the invention. Such lines may be obtained as described, e.g., in U.S. Patent Publication No. 20060085871.

One of skill in the art will be able to derive whole plants from plant cell or cells containing a nucleic acid construct of the present invention using well established techniques as appropriate for the plant species of interest. The plant cell or cells is/are maintained under suitable conditions to give rise to a plant. Expression of the target gene is inhibited in at least some cells of the plants so obtained, e.g., those cells in which a smRNA that binds to the smRNA complementary sites is expressed.

Transgenic plants, plant cells, and plant cell lines of the present invention can, in various embodiments, be any monocot or dicot plant or plant cell, such as, but not limited to, plants of commercial, agricultural, or ornamental interest, such as crop plants (e.g., crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Dicots of interest include, but are not limited to, canola, cotton, potato, quinoa, amaranth, buckwheat, safflower, soybean, sugarbeet, and sunflower, more preferably soybean, canola, and cotton. Monocots of interest include, but are not limited to, wheat, oat, barley, maize, rye, triticale, rice, ornamental and forage grasses, sorghum, millet, and sugarcane, more preferably maize, wheat, and rice. Also envisioned are mosses, algae, and also plants frequently used for research purposes, e.g., *A. thaliana, N. benthamiana*, etc.

Genes of Interest, Target Sequences, and Nucleic Acid Sequences

Genes of interest in the present invention can be, in various embodiments of the invention, a coding or non-coding sequence from any of a variety of species (including, but not limited to, non-eukaryotes such as bacteria, and viruses; fungi, invertebrates such as arthropods, annelids, nematodes, and molluscs; and vertebrates such as amphibians, fish, birds, and mammals; plants, including monocots and dicots, such as crop plants, ornamental plants, and non-domesticated or wild plants. A gene of interest may be a translatable (coding) sequence, such as genes encoding transcription factors, genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A gene of interest can be a gene native to the plant in which a nucleic acid construct of the invention is to be transcribed, or can be a non-native gene (e.g., a pathogen gene or a gene of a non-pathogen that inhabits the plant). The gene of interest could be a transgene.

A gene of interest can be a marker gene, for example, a selectable marker gene encoding antibiotic, antifungal, or herbicide resistance, or a marker gene encoding an easily detectable trait (e.g., phytoene synthase or other genes imparting a particular pigment to the plant), or a gene encoding a detectable molecule, such as a fluorescent protein, luciferase, or a unique polypeptide or nucleic acid "tag" detectable by protein or nucleic acid detection methods, respectively). The gene of interest. A gene of interest could be a gene encoding a functional RNA such as a miRNA, siRNA, RNA components of ribosomes or ribozymes, small nucleolar RNAs, or other non-coding RNAs A target gene could be any gene of interest, though as mentioned above the invention also contemplates modulating expression or activity of genes of interest that are not direct targets of inhibition (e.g., that do not encode sequences that are direct targets of cleavage mediated by siRNA produced in accordance with the inventive methods). A target sequence could be any sequence transcribed from a target gene. The nucleic acid sequence in a construct of the invention could correspond to any portion of a target sequence, as described above.

The invention contemplates inhibiting expression of a gene which is exogenous to the host plant but endogenous to a plant pest or pathogen or non-pathogen present in or on the plant (e.g., viruses, bacteria, fungi, and invertebrates such as insects, nematodes, and molluscs). Thus, one aspect of the invention provides nucleic acid constructs and transgenic plants containing them, wherein the target gene is selected to provide resistance to a plant pest or pathogen, for example, resistance to a nematode such as soybean cyst nematode or root knot nematode or to a pest insect. Pest invertebrates include, but are not limited to, pest nematodes (e.g., cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., and foliar nematodes *Aphelenchus* spp. or *Aphelenchoides* spp.), pest molluscs (slugs and snails), and pest insects (e.g., corn rootworms, Lygus spp., aphids, corn borers, cutworms, armyworms, leafhoppers, Japanese beetles, grasshoppers, and other pest coelepterans, dipterans, and lepidopterans). Plant pathogens of interest include fungi (e.g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillits* spp., *Gibberella* spp., *Pyricularia* spp., *Alternaria* spp., and *Phytophthora* spp.), bacteria (e.g., the bacteria that cause leaf spotting, fireblight, crown gall, and bacterial wilt), mollicutes (e.g., the mycoplasmas that cause yellows disease and spiroplasmas such as *Spiroplasma kinkelii*, which causes corn stunt), and viruses (e.g., the viruses that cause mosaics, vein banding, flecking, spotting, or abnormal growth). See also G. N. Agrios, "Plant Pathology" (Fourth Edition), Academic Press, San Diego, 1997, 635 pp., which is incorporated by reference herein, for descriptions of fungi, bacteria, mollicutes (including mycoplasmas and spiroplasmas), viruses, nematodes, parasitic higher plants, and flagellate protozoans, all of which are plant pests or pathogens of interest. See also the continually updated compilation of plant pests and pathogens and the diseases caused by such on the American Phytopathological. Society's "Common Names of Plant Diseases", compiled by the Committee on Standardization of Common Names for Plant Diseases of The American Phytopathological Society, 1978-2005, available online at the website of The American Phytopathological Society, which is incorporated by reference herein.

Non-limiting examples of fungal plant pathogens of particular interest include *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Pythium aphanidermatum* and other *Pythium* spp., *Rhizoctonia solani*, *Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglitinans* (*G. subglutinans*), *Diplodia maydis, Sporisorium holci-sorghi, Colletotrichum graminicola, Setosphaeria turcica, Aureobasidium zeae, Phytophthora infestans, Phytophthora sojae, Sclerotinia sclerotiorum*, and the numerous fungal species provided in Tables 4 and 5 of U.S. Pat. No. 6,194,636. Non-limiting examples of bacterial pathogens include *Pseudomonas avenae, Pseudomonas andropogonis, Erwinia stewartii, Pseudomonas syringae* pv. *syringae*, and the numerous bacterial species listed in Table 3 of U.S. Pat. No. 6,194,636. Non-limiting examples of viral plant pathogens include maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), and the numerous viruses listed in Table 2 of U.S. Pat. No. 6,194,636.

Non-limiting examples of invertebrate pests include pests capable of infesting the root systems of crop plants, e.g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape *colaspis* (*Colaspis brunnea*), seedcorn beetle (*Stenolophus lecontei*), and slender seedcorn beetle (*Clivinia impressifrons*), as well as the parasitic nematodes listed U.S. Pat. Nos. 6,194,636 and 7,064,243.

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in United States Patent Application Publication 200400098761. Target genes from pathogens can include genes for viral translation initiation factors, viral replicases, miRNAs, miRNA precursor molecules, fungal tubulin, fungal vacuolar ATPase, fungal chitin synthase, enzymes involved in fungal cell wall biosynthesis, cutinases, melanin biosynthetic enzymes, polygalacturonases, pectinases, pectin lyases, cellulases, proteases, and other genes involved in invasion and replication of the pathogen in the infected plant. Examples of genes that may be modulated, e.g., inhibited, in the practice of the invention include essential genes, genes involved in processes such as development, metabolism, or neurotransmission (in the case, e.g., of insects, nematodes, and other organisms having a nervous system), and genes whose products are targets of existing herbicides, fungicides, insecticides, or other pest control agents.

Specific, non-limiting examples of suitable target genes also include amino acid catabolic genes (such as, but not limited to, the maize LKR/SDH gene encoding lysine-ketoglutarate reductase (LKR) and saccharopine dehydrogenase (SDH), and its homologues), maize zein genes, genes involved in fatty acid synthesis (e.g., plant microsomal fatty acid desaturases and plant acyl-ACP thioesterases, such as, but not limited to, those disclosed in U.S. Pat. Nos. 6,426,448, 6,372,965, and 6,872,872), genes involved in multi-step biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes can include genes encoding undesirable proteins (e.g., allergens or toxins) or the enzymes for the biosynthesis of undesirable compounds (e.g., undesirable flavor or odor components). Thus, one embodiment of the invention is a transgenic plant or tissue of such a plant that is improved by the suppression of allergenic proteins or toxins, e.g., a peanut, soybean, or wheat kernel with decreased allergenicity. Target genes can include genes involved in fruit ripening, such as polygalacturonase. Target genes can include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575).

In some embodiments, genes associated with lignin biosynthesis are targeted for modulation. Lignin is a major component of wood, and the regulation of its biosynthesis has can have a major impact on paper and pulping processes. Several genes have been identified that are involved in the biosynthesis of lignin including, but not limited to sinapyl alcohol dehydrogenase (SAD), cinnamyl alcohol dehydrogenase (CAD), 4-coumarate:CoA ligase (4CL), cinnamoyl CoA O-methyltransferase (CCOAOMT; also referred to as CCOMT), caffeate O-methyltransferase (COMT), ferulate-5-hydroxylase (F5H), cinnamate-4-hydroxylase (C4H), p-coumarate-3-hydroxylase (C3H), and phenylalanine ammonia lyase (PAL). Reviewed in Anterola & Lewis, 2002; Boerjan et al., 2003. Reduction in the activities of one or more of these genes has been shown to result in reduced lignin deposition (see Anterola & Lewis, 2002; Boerjan et al., 2003), and thus these genes provide potential targets for miRNA-mediated gene expression modulation.

In some embodiments, genes associated with cellulose biosyntheses are targeted for modulation. Representative, non-limiting genes that have been identified that are associated with cellulose biosynthesis include cellulose synthase (CeS; also referred to as CESA in some plants), cellulose synthaselike (CSL), glucosidase, glucan synthase, Korrigan endocellulase, callose synthase, and sucrose synthase.

In some embodiments, other plant genes are targeted for modulation using the methods of the present invention. A non-limiting list of gene families that can be targeted include hormone-related genes, including but not limited to isopentyl transferase (ipt), gibberellic acid (GA) oxidase, auxin (AUX), auxin-responsive and auxin-induced genes, and members of the rooting locus (ROL) gene family; hemicellulose-related genes, disease-related genes, stress-related genes, growth-related genes and transcription factors.

In certain embodiments the nucleic acid sequence in a construct of the invention does not encode an RNA aptamer such as those described in U.S. Patent Publication 20060200878. In certain embodiments the nucleic acid sequence does not encode a ribozyme. In certain embodiments the construct of the invention is not a construct described in Adenot, X., Elmayan, T., Lauressergues, D., Boutet, S., Bouche, N., Gasciolli, V., and Vaucheret, H., Curr. Biol. 16, 927-932, 2006. In particular, in certain embodiments the construct of the invention is not the construct referred to as pART27-AtTAS3 in the afore-mentioned publication. In certain embodiments the construct of the invention is not one that comprises at least a 50 nt portion of the TAS3 insert of the afore-mentioned vector. In certain embodiments of the invention the nucleic acid sequence is not a nucleic acid sequence described in the afore-mentioned publication. In certain embodiments of the invention the nucleic acid sequence, or construct, of the invention is not one described previously in the art, wherein such nucleic acid sequence or construct may have included smRNA complementary sites flanking a nucleic acid sequence for purposes other than one or more of those purposes contemplated by the present invention and/or wherein the creators or users of the construct did not recognize the existence of the dual smRNA complementary sites flanking a nucleic acid sequence and/or did not recognize the properties described herein that are conferred by dual smRNA complementary sites flanking a nucleic acid sequence, e.g., where the creators or users did not recognize that the presence of smRNA complementary sites on each side of a nucleic acid sequence enhances the production of siRNA from an RNA obtained by transcription of the construct, relative to the production of siRNA in the presence of only one smRNA complementary site. Such nucleic acid sequences and constructs may be explicitly excluded from the invention. In certain embodiments of the invention the smRNA complementary sites in a construct of the invention do not naturally flank the same nucleic acid sequence in nature, e.g., in plants. In certain embodiments of the invention the nucleic acid sequence is not, or does not comprise, a TAS gene or fragment thereof having a length of between 10, 12, 15, 18, 20, 25, 50, or 100 nucleotides up to the full length of the TAS gene, or up to any length shorter than the full length of the TAS gene. In certain embodiments of the invention the nucleic acid sequence is not, or does not comprise, a TAS3 gene or fragment thereof having a length of between 10, 12, 15, 18, 20, 25, 50, or 100 nucleotides up to the full length of the TAS3 gene, or up to any length shorter than the full length of the TAS gene. In certain embodiments of the invention the nucleic acid sequence is not, or does not comprise, an *A. thaliana* gene fragment thereof having a length of between 10, 12, 15, 18, 20, 25, 50, or 100 nucleotides up to the full length of the gene, or up to any length shorter than the full length of the gene. In certain embodiments of the invention the nucleic acid sequence is not, or does not comprise, an *N. benthamiana* gene fragment thereof having a length of between 10, 12, 15, 18, 20, 25, 50, or 100 nucleotides up to the full length of the gene, or up to any length shorter than the full length of the gene.

In certain embodiments the nucleic acid sequence is not a nucleic acid sequence that is naturally flanked by miR390 complementary sites in a plant. In certain embodiments the nucleic acid sequence is not a nucleic acid sequence that is naturally flanked by smRNA complementary sites (e.g., miRNA complementary sites) in a plant. In certain embodiments the nucleic acid sequence in the construct is not a fragment of a second nucleic acid sequence that is naturally flanked by miR390 complementary sites in a plant, wherein said fragment has a length of 10, 12, 15, 18, 20, 25, 50, or 100 nucleotides up to the full length of the second nucleic acid sequence. In certain embodiments the nucleic acid sequence in the construct is not a fragment of a second nucleic acid sequence that is naturally flanked by smRNA complementary sites (e.g., miRNA complementary sites) in a plant, wherein said fragment has a length of 10, 12, 15, 18, 20, 25, 50, or 100 nucleotides up to the full length of the second nucleic acid sequence. In certain embodiments of the invention the smRNA complementary sites do not simply serve to liberate the nucleic acid sequence between them from a longer nucleic acid sequence by allowing smRNAs (e.g., miRNAs) to direct cleavage within the complementary sites.

In some embodiments, a pathogen, pest, or other organism consumes smRNA, e.g., siRNA, produced by a plant or plant cell according to the inventive methods, and the consumed nucleic acid directs gene silencing in the organism. Such gene silencing may achieve a beneficial or therapeutic effect on the organism or exert a deleterious effect on the organism. In the latter case, the result may be to control a pest or pathogen.

The invention provides methods for identifying a plant gene whose knockdown yields a desired phenotype. Certain of the methods comprise inhibiting expression of a candidate plant gene using any of the inventive methods for knockdown of a gene provided herein, e.g., by a method involving introducing a construct of the invention comprising a sequence corresponding to the candidate gene flanked by smRNA complementary sites into the plant or a precursor of the plant, or using any method described herein in which dual smRNA binding to an ssRNA and subsequent smRNA-mediated cleavage leads to production of siRNAs that inhibit expression of the candidate gene. Following inhibition of the candidate gene, the phenotype of the plant is assessed with respect to any one or more properties or traits of interest (see below for discussion of such properties and traits). In some embodiments, if the plant exhibits a desirable property or trait (or an improvement in such property or trait), then the candidate gene is identified as a plant gene whose knockdown yields a desirable phenotype. In some embodiments, if the plant exhibits a reduction or absence of an undesirable property or trait (which trait may be the opposite of any desired property or trait), then the candidate gene is identified as a plant gene whose knockdown yields a desirable phenotype. The assessment may be open-ended, e.g., it could include maintaining the plant under any of a variety of environmental condition and determining whether the plant exhibits any desirable property or trait under such conditions. The assessment could determine whether the plant exhibits any one or more specific desired properties or traits or exhibits a reduction or absence of any one or more specific undesired properties or traits. Thus "desirable phenotype" can refer to any desirable phenotype or to any one or more specific desired phenotypes.

The methods may comprise knocking down expression of a plurality of different candidate genes in a plurality of individual plants, wherein a single gene is knocked down in an individual plant. The plants are then assessed to identify one or more plants having a desirable phenotype. The identity of the gene may then be determined. In some instances the identity of the gene will be evident because the identity of the construct that was introduced into the plant or precursor of the plant is known. In some instances a library containing multiple different constructs targeted to different candidate genes (e.g., every gene in the genome of the plant or any subset thereof) is used, and it may be necessary to isolate the construct or a portion of the construct and determine part or all of its sequence in order to determine which gene was knocked down. A similar method could knock down multiple genes in individual plants and thus be used to identify genes which, when knocked down in combination, yield a desirable phenotype.

Once a gene (or genes) whose knockdown yields a desirable phenotype is identified, such knockdown can be accomplished in other plants of the same or different species (e.g., an ortholog in another species can be knocked down) using any method known in the art including, but not limited to, the methods for gene knockdown of the present invention, other methods that employ RNA interference, etc. Alternately, one or both genomic copies of the gene could be functionally inactivated in any of a variety of different ways, e.g., by mutations such as substitution, insertion, deletion, etc., such that one or more (e.g., one, more than one, all) of the functions normally performed by an expression product of the gene when it is functioning in its native environment (that is within an in vivo environment) is significantly inhibited (e.g., by at least 30%, 40%, 50%, 60%, 70%, 80%, 90%, or 95%) as compared with a control in which the gene has not been functionally inactivated. In some embodiments the mutation significantly reduces (e.g., by at least 30%, 40%, 50%, 60%, 70%, 80%, 90%, or 95%) or substantially eliminates (e.g., reduces by at least 98% or at least 99%) expression of the gene or results in an altered expression product that substantially lacks one or more of the functional activities it possesses in the absence of the mutation (e.g., the functional activity whose reduction or loss results in the desirable phenotype). The mutation could be in a coding or noncoding portion of the gene. For example, one or more exons could be completely or partly deleted or an insertion made into a critical region of the gene. The mutation could be in a promoter or other regulatory region. Any manipulation that results in knockdown, knockout, or reduced or absent functional activity of the gene or its expression product could be used.

Thus the above method can further comprise (i) knocking down or functionally inactivating the identified gene using any available method or (ii) identifying a plant in which said gene is already functionally inactivated such that one or more functional activities of its expression product(s) is eliminated or reduced. In one embodiment, a gene whose knockdown yields a desirable phenotype is identified in a first plant species. The first species could be, e.g., a species such as *A. thaliana* that is widely used for research purposes. An ortholog of the gene in second plant species, e.g., a commercially important plant such as a crop plant is identified. The ortholog is then knocked down, mutated at the level of the genome, or its functional activity otherwise inhibited or reduced by a method of the invention involving dual smRNA binding and subsequent smRNA-mediated cleavage or any method known in the art. It will be appreciated that a gene may have a number of functional activities of which only some may be inactivated by any particular mutation or manipulation. It will be appreciated that if a gene or its expression product has multiple activities, it is only necessary to reduce or inhibit the functional activity or activities whose reduction or inhibition is responsible for the desirable phenotype.

The invention also relates in various embodiments to any plant or plant cell in which a gene identified using a method of the invention as being one whose knockdown yields a desirable phenotype is knocked down or functionally inactivated, or wherein the activity of an expression product of the gene is otherwise inhibited using any method known in the art. A variety of methods of eliminating, reducing or inhibiting the function or activity of the gene that do not employ RNAi can be used. Such methods may be referred to as "conventional". For example, the gene could be mutated and thereby functionally inactivated using methods known in the art. Transposon-mediated mutagenesis, chemical mutagenesis, or ultraviolet-induced mutagenesis could be used. Heterozygous mutants can be bred to obtain homozygotes in which both alleles of the gene are mutated. In some embodiments the resulting plant does not contain any introduced DNA sequences that are not naturally found in the plant. Collections of plants having alterations or mutations could be screened to identify a plant having an alteration or mutation in the gene whose knockdown yields a desirable phenotype. Once of skill in the art will be aware of multiple ways to functionally inactivate a gene and/or to identify a plant in which a gene is functionally inactivated either as a result of a naturally occurring mutation or as a result of a genetic manipulation or mutation generated as a result of the hand of man. See, e.g., Acquaah, G., Principles of Plant Genetics and Breeding, Blackwell Publishing, 2006.

Properties and Traits of Interest

Properties and traits of interest include, e.g., herbicide, insect, disease (viral, bacterial, fungal, nematode) or environmental resistance (e.g., drought resistance, salt tolerance), male sterility, drydown, standability, prolificacy, starch properties, oil quantity and quality, yield, or nutritional quality or edible plant products. Improvement of a plant's ability to tolerate various environmental stresses such as, but not limited to, drought, excess moisture, chilling, freezing, high temperature, salt, and oxidative stress, also can be effected through modulation of the expression or activity of appropriate genes of interest, e.g., by inhibiting expression of a target gene. Modulation so as to favorably effect plant water content, total water potential, osmotic potential, and turgor may enhance the ability of the plant to tolerate drought.

Production of mycotoxins, including aflatoxin and fumonisin, by fungi associated with monocotyledonous plants such as maize, and plants such as peanuts, is a significant factor in rendering the grain not useful. These fungal organisms often do not cause disease symptoms and/or may not interfere with the growth of the plant, but they produce chemicals (mycotoxins) that are toxic to animals. It is contemplated that inhibition of the growth of these fungi would reduce the synthesis of these toxic substances and therefore reduce grain losses due to mycotoxin contamination. Inhibition of biosynthetic genes responsible for synthesis of the mycotoxin using the present invention would be of considerable use. The result would be a reduced presence of mycotoxins on grain, peanuts, or other crops and enhanced safety. Similar principles apply to inhibiting synthesis of a variety of toxic or otherwise undesirable compounds (e.g., antigenic substances) that may be produced by plants or plant pathogens or nonpathogenic organisms (which term includes viruses) that infect or are present in plants. The undesirable compounds may be, e.g., compounds that alter ripening, appearance, shelf life, etc.

In certain embodiments, a transgenic plant of the invention has at least one altered trait, relative to a nontransgenic plant (e.g., relative to an otherwise essentially identical nontransgenic plant), wherein the trait is selected from the group consisting of: (a) improved stress tolerance; (b) improved resistance to a pest or pathogen of the plant; (c) reduced production of a toxin or antigen; (d) modified primary metabolite composition; (e) modified secondary metabolite composition; (f) modified trace element, carotenoid, or vitamin composition; (g) improved yield; (h) improved ability to use nitrogen or other nutrients; (i) modified agronomic characteristics; (j) modified growth or reproductive characteristics; (k) improved harvest, storage, or processing quality; (l) improved resistance to an herbicide, fungicide, insecticide or pesticide; (m) altered accumulation of an herbicide, fungicide, insecticide, pesticide, heavy metal, or contaminant within plant tissues. Improved stress tolerance can comprise improved tolerance of water deficit or drought, heat, cold, non-optimal nutrient or salt levels, non-optimal light levels, crowding, allelopathy, or wounding). The plant may exhibit improved resistance to a pest or pathogen (e.g., insect, nematode, fungal, bacterial, or viral pest or pathogen) of the plant. The plant may exhibit a modified primary metabolite (e.g., fatty acid, oil, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition; a modified trace element (e.g., iron, zinc), carotenoid (e.g., beta-carotene, lycopene, lutein, zeaxanthin, or other carotenoids and xanthophylls), or vitamin (e.g., tocopherols) composition; improved yield (e.g., improved yield under non-stress conditions or improved yield under biotic or abiotic stress); improved ability to use nitrogen or other nutrients; modified agronomic characteristics (e.g., delayed ripening; delayed senescence; earlier or later maturity; improved shade tolerance; improved resistance to root or stalk lodging; improved resistance to "green snap" of stems; modified photoperiod response); modified growth or reproductive characteristics (e.g., intentional dwarfing; intentional male sterility, useful, e.g., in improved hybridization procedures; improved vegetative growth rate; improved germination; improved male or female fertility); improved harvest, storage, or processing quality (e.g., improved resistance to pests during storage, improved resistance to breakage, improved appeal to consumers); or any combination of these traits. It may be desirable to modify the amino acid (e.g., lysine, methionine, tryptophan, or total protein), oil (e.g., fatty acid composition or total oil), carbohydrate (e.g., simple sugars or starches), trace element, carotenoid, or vitamin content of seeds of crop plants (e.g., canola, cotton, safflower, soybean, sugarbeet, sunflower, wheat, maize, or rice), preferably in combination with improved seed harvest, storage, or processing quality, and thus provide improved seed for use in animal feeds or human foods. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e.g., peanut allergens including ara h 1, wheat allergens including gliadins and glutenins, soy allergens including P34 allergen, globulins, glycinins, and conglycinins) or of a toxic metabolite (e.g., cyanogenic glycosides in cassaya, *solanum* alkaloids in members of the Solanaceae). The plant may exhibit altered accumulation of an herbicide, fungicide, insecticide, pesticide, heavy metal, or other contaminant, within plant tissues. Increased accumulation of certain of these agents may be advantageous as it may increase resistance of the plant to plant pathogens or make the plant more useful for bioremediation. Decreased accumulation of certain of these agents may be advantageous as it may make a food or food product incorporating plant material safer for consumption, e.g., by humans or other animals.

Exemplary Uses

The present invention contemplates a wide variety of uses for the plants, plant cells, plant cell and root lines described herein, of which but a few are described here. Plants are a source of numerous products useful for human and animal existence. Plants that have been improved by modulating expression or activity of a gene of interest or a gene product encoded thereby using the compositions and methods of the invention may be used for any purpose known in the art for which plants are typically used, e.g., as sources of food, wood, industrially useful chemicals, shade, esthetic or ornamental purposes, etc. The transgenic plant may be harvested, or one may harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338 and PCT Publications WO 95/06128 and WO 02/057471.

Transgenic plants, plant cell lines and root lines may be used, without limitation, for the production of any of a variety of useful products that may be produced in plants such as industrially useful or pharmaceutically active compounds (antibodies, vaccine antigens, polypeptides, small molecules) or RNA species. Transgenic plants may also be used for environmental remediation such as to take decontaminate soil or water, e.g., to take up heavy metals from soil or water, etc. The invention provides a food (e.g., an edible fruit or vegetable), processed food product or food supplement, a plant extract, ornamental flower, etc., obtained from a plant of the present invention. Modulating expression or activity of a gene or gene product (e.g., inhibiting gene expression) is of use for research purposes, e.g., in order to explore fundamental biological mechanisms, enhance understanding of gene function, and thereby lead to further improvement in useful characteristics of plants.

Where numerical ranges are given in this document, endpoints are included within the range unless otherwise indicated, and the invention also includes embodiments in which either endpoint (upper or lower) is excluded and embodiments in which both endpoints are excluded. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

The terms "approximately" or "about", when referring to a numerical value, amount, or percentage encompasses variations of ±10% in certain embodiments, ±5% in certain embodiments, ±1% in certain embodiments, and ±0.5% in certain embodiments, from the stated value, amount, or percentage, as appropriate to the practice of the invention. Where such variation may result in a fraction, the fraction may be rounded to the nearest integer value in certain embodiments.

In certain embodiments of the invention the terms "approximately" or "about" in reference to a number include values that fall within a range of 10%, 5%, 1%, or 0.5% in either direction (greater than or less than) of the number unless otherwise stated or where context dictates otherwise (e.g., where by definition it is not possible to exceed 100% of a value). Unless otherwise indicated, the invention includes embodiments in which any one or more relevant values, amounts, or percentages as set forth in the description and/or claims is modified by the term "about" and embodiments in which the value, amount, or percentage is exactly as set forth therein. The terms "derive", "deriving", "derived", "derived from", etc., can refer to a process of obtaining a first entity from a second entity (e.g., directly obtaining) and/or a process involving one or more intermediate steps as known in the art and/or described herein. For example, a plant is "derived from" a precursor such as a plant cell by obtaining or providing a plant cell and performing one or more procedures or steps known to those of skill in the art that result in production of a plant. Applicant reserves the right to substitute the terms "obtain", "obtaining", "obtained" or "obtained from" for the afore-mentioned terms.

In the claims or description above, articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim, e.g., one that is dependent on the same base claim unless otherwise indicated or unless it would be evident to one of ordinary skill in the art that a contradiction or inconsistency would arise. Where elements are presented as lists, e.g., in Markush group format, it is to be understood that each subgroup of the elements is also disclosed, and any element(s) can be removed from the group. For example, any smRNA complementary sequence, any smRNA (e.g., an siRNA or miRNA), any target gene, any plant, any construct, any nucleic acid sequence, etc. can be removed from any group in which it appears. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity some of these embodiments have not been specifically set forth in haec verba herein. Applicant reserves the right to delete any one or more nucleic acid sequences from the instant specification and/or figures at any time. Such deletion shall not be considered to constitute adding new matter but may be done, e.g., for purposes of convenience, e.g., where such nucleic acid sequence is not needed to describe or enable the claims.

Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format. Furthermore, any claim reciting an optional feature or element may be rewritten to make such optional feature mandatory, to exclude such optional feature, or to explicitly allow such optional feature to be present or absent.

It is understood that where the claim refer to a nucleic acid construct, the invention provides methods of using the nucleic acid construct (e.g., to modulate expression of a gene of interest in plants or plant cells), methods of making the nucleic acid construct, methods of generating plants comprising the nucleic acid construct, etc. Thus the invention includes embodiments in which any of the nucleic acid constructs of the invention is employed in any method disclosed herein. Features relevant to the nucleic acid construct of claims dependent on claim 9 may be present in the nucleic acid construct of claims 5 and claims dependent thereon in various embodiments of the invention.

Furthermore, the invention includes embodiments in which any specific feature or characteristic as described in the more detailed Exemplification herein is applied to or present in any of the descriptions or embodiments set forth herein.

It will be understood by those skilled in the art that various changes in form and details may be made without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the work described herein, high-throughput DNA sequencing was adapted to the discovery of endogenous small RNAs from the moss *Physcomitrella patens* and *Arabidopsis*. The data demonstrate that *P. patens* has four loci that give rise to phased siRNAs resembling tasiRNAs. These moss siRNAs are in phase with cleavage sites for miR390, the same miRNA important for tasiRNA phasing in flowering plants (Allen et al., 2005). The four moss siRNA loci are each flanked by dual miR390 complementary sites that are both cleaved in vivo. *Arabidopsis* TAS3 also has a second, conserved miR390 complementary site that had not been originally recognized; as in *P. patens*, the region that generates phased siRNAs falls between the two miR390 complementary sites. The newly identified upstream miR390 complementary site of AtTAS3 is not cleaved, even though it binds a miR390-associated silencing complex in vitro and is necessary for full AtTAS3 function in vivo, indicating that conserved miRNA complementary sites can function independently of target cleavage in plants. The work described herein also shows that *Arabidopsis* genes with two or more small RNA complementary sites universally produce phased siRNAs from the regions that fall between the sites. These results indicate that dual miRNA complementary sites are a trigger for siRNA biogenesis that has been conserved for the past 400 million years and provide potential insights into the recognition and silencing of aberrant RNAs.

One of the first reports of tasiRNAs noted their ~21-nt phasing, which was suggestive of successive DCL-catalyzed cleavage beginning from a defined point on a dsRNA substrate (Vazquez et al., 2004b). It was subsequently recognized that the single-stranded tasiRNA precursors are cleaved by miRNAs (Allen et al., 2005; Yoshikawa et al., 2005), and that this cleavage site defines a starting point for DCL4-catalyzed siRNA processing (Gasciolli et al., 2005; Xie et al., 2005). Yet the majority of *Arabidopsis* miRNA targets are cleaved without initiating the biogenesis of detectable amounts of siRNAs (Lu et al., 2005).

In the case of the siRNAs triggered by miR390, the expressed siRNAs emanated from a region flanked by miR390 complementary sites. The phasing registers of the PpTAS siRNA populations (FIG. 1) and the observation of miR390-directed cleavage at both complementary sites in PpTAS1 (FIG. 1A) were consistent with successive DCL activity initiated from both ends of a dsRNA whose termini were defined by dual miR390-mediated cleavage events. The location of the pine tasiARFs, which also appeared to be flanked by two cleavable sites (FIGS. 2B and 3A), suggested that the same process produces siRNAs in gymnosperms. Furthermore, phased siRNAs were universally observed to emanate from regions of *Arabidopsis* genes bounded by small RNA complementary sites (FIGS. 5, 8A-8C). Small RNAs whose 5' ends are within one nucleotide of the residues predicted by successive cleavage in precise 21-nt increments account for 71% of all small RNAs observed from *P. patens* and *Arabidopsis* genes with two or more complementary sites, indicating that such loci produce phased siRNAs. The major reason that the percentage of phased siRNAs is not even higher is the occurrence of both 21- and 22-nt small RNAs; thus, precise 21-nt phasing degenerates as a result of occasional 22-nt cleavages. We conclude that one discriminating molecular feature of an RNA that triggers RdRp activity and subsequent entry into a phased siRNA pathway is the occurrence of dual small RNA-mediated cleavage events. Perhaps the resulting lack of any molecular signatures of normally processed mRNA (i.e. lack of 5' cap, 3' poly-A tail, and other mRNA-associated factors such as those deposited during splicing) direct such dual cleavage products to become RdRp substrates (FIG. 6A).

Figure 2:
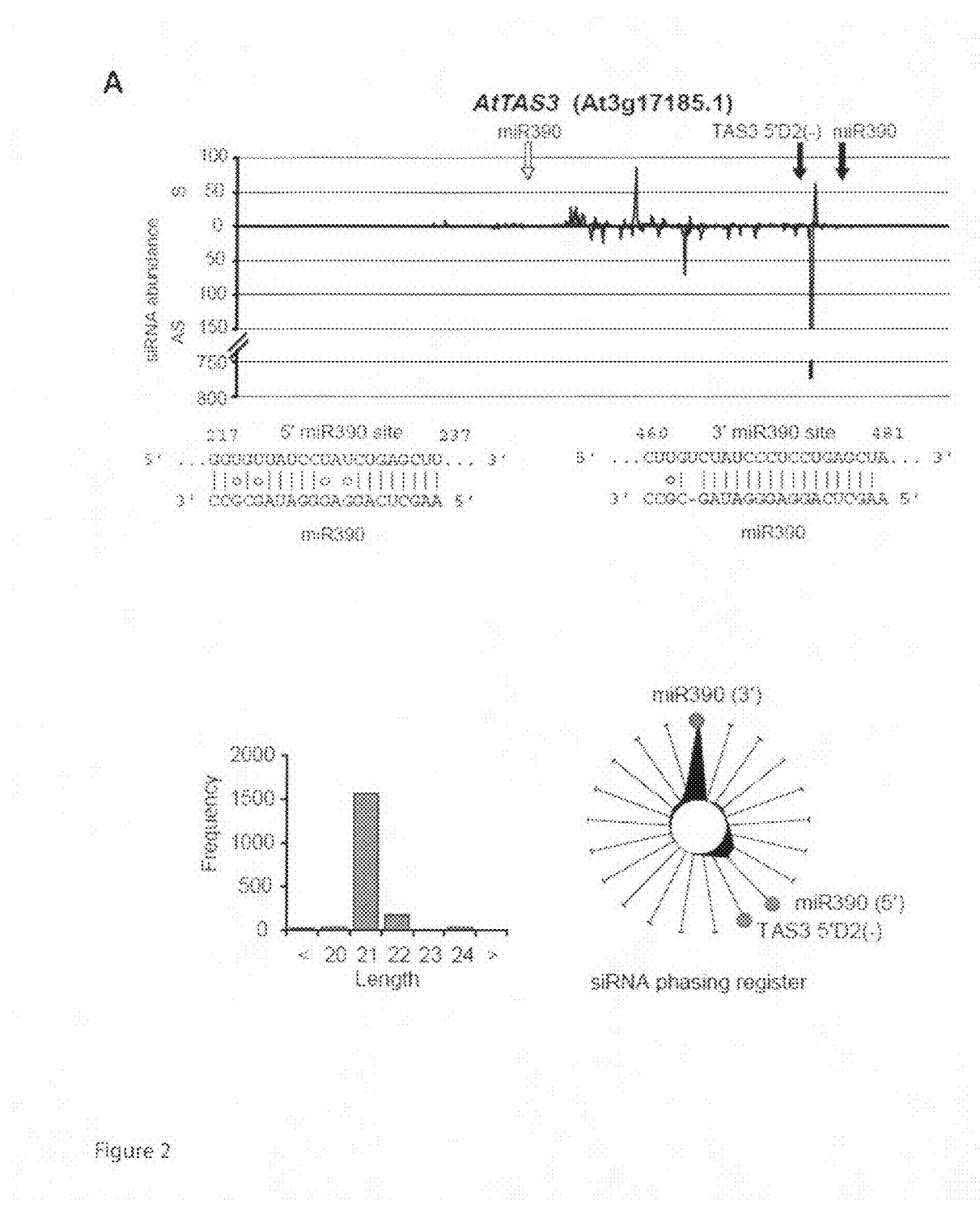
FIG. 2 shows that dual miR390 complementary sites were conserved in seed-plant TAS3 loci. (A) *Arabidopsis* TAS3 siRNAs. The positions, length distribution, and phasing register of *Arabidopsis* small RNAs (SEQ ID NOs: 92 and 291, respectively, in order of appearance) corresponding to AtTAS3 are plotted as in FIG. 1. A high-resolution graph is also available (FIG. 7). The two miR390 complementary sites (SEQ ID NO: 1) are indicated by arrows, with the open arrow indicating that no evidence of cleavage at the 5' site was found. The site of secondary cleavage proposed to be directed by the highly abundant TAS3 5'D2(-) tasiRNA is also indicated (Allen et al., 2005). The most populated register contained 883 siRNAs (48.5%); 1,440 (79%) of the siRNAs fell in the same or adjacent registers as a complementary site. (B) TAS3 ESTs from diverse flowering plant genera (SEQ ID NOs: 292-331, respectively, in order of appearance) contained dual miR390 complementary sites that flanked the area of predicted tasiRNA production. Alignments were generated using ClustalW and color-coded based on the confidence of the local alignment using the CORE function of T-Coffee. tasiARF refers to the regions homologous to AtTAS3 5'D7(+) and 5'D8(+). The regions corresponding to the 5' miR390 complementary site, tasiARF, and 3' miR390 complementary site are expanded. Black and white lines indicate the registers in phase with the 3' and 5' sites, respectively. EST details are given in Table 3. Gymnosperm is abbreviated (Gym). (C) Analysis of miR390 complementary sites in EST homologs of AtTAS3. Complementary site positions were numbered starting with the residue corresponding to the 5' nucleotide of miR390, and scored based on their pairing to *Arabidopsis* miR390a. Gray, G:U wobbles; black, other non-Watson-Crick pairs. This analysis was restricted to the flowering-plant TAS3 homologs because the 5' site of the *Pinus taeda* homolog is cleaved.
Figures 1, 2B:
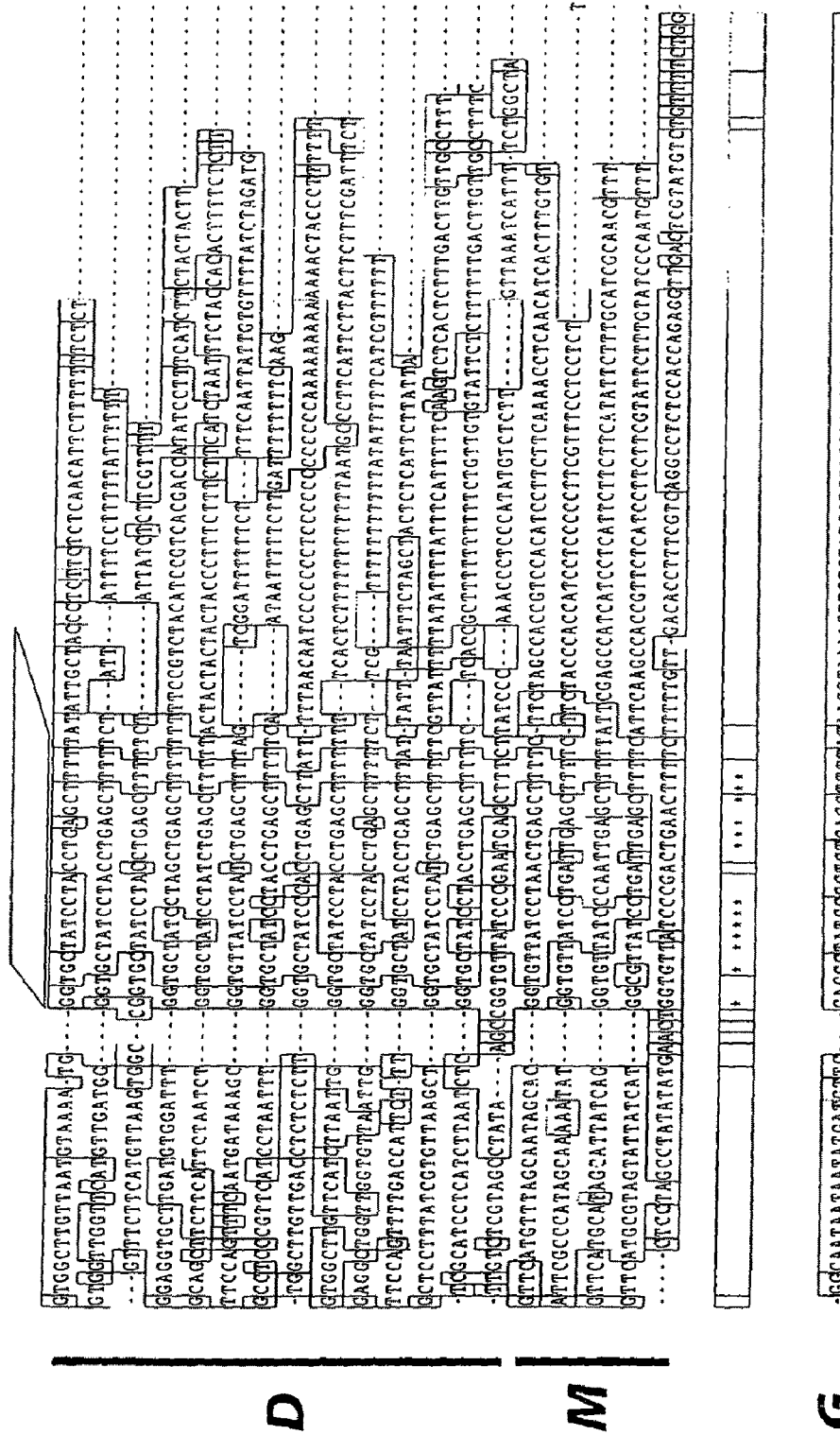
Figures 2, 2B:
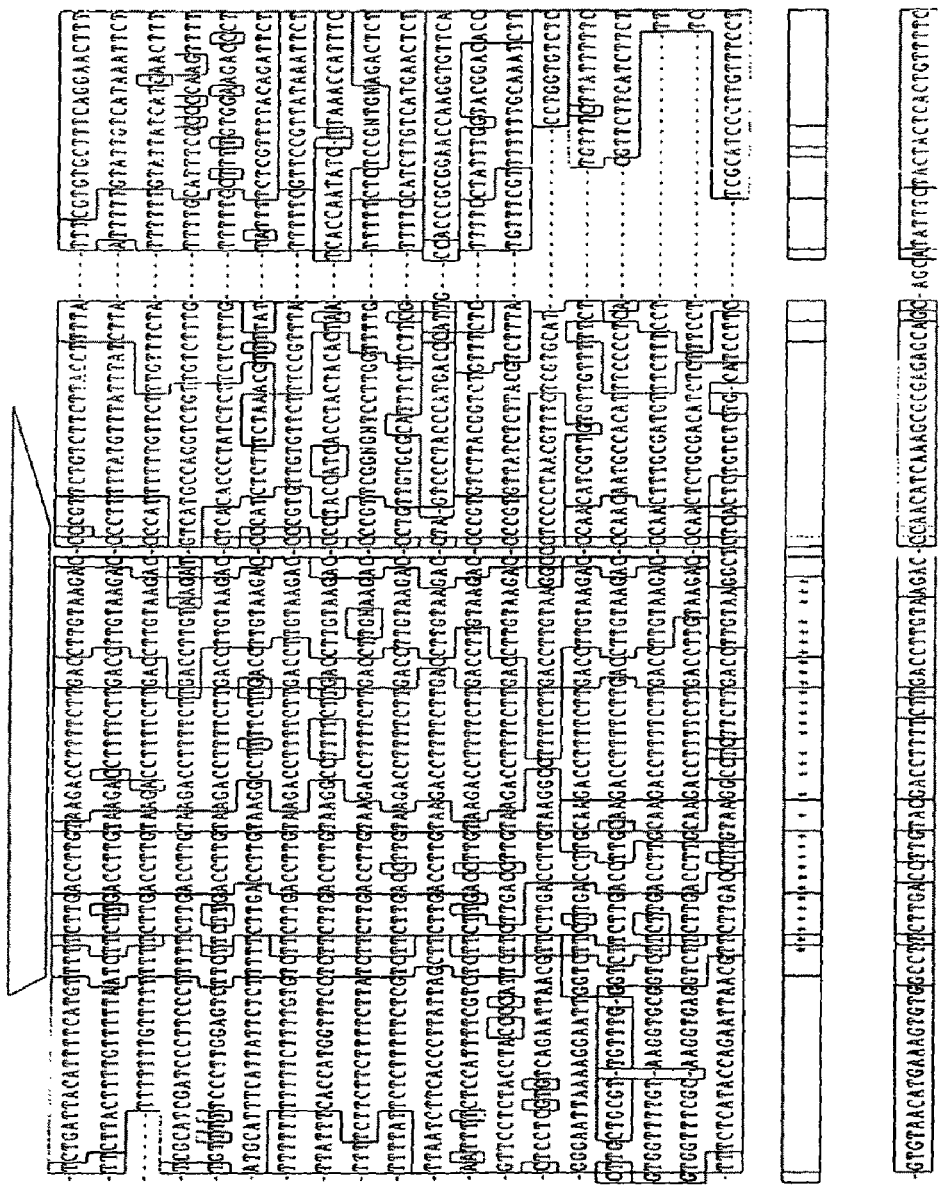
Figures 2, 2B, 3:
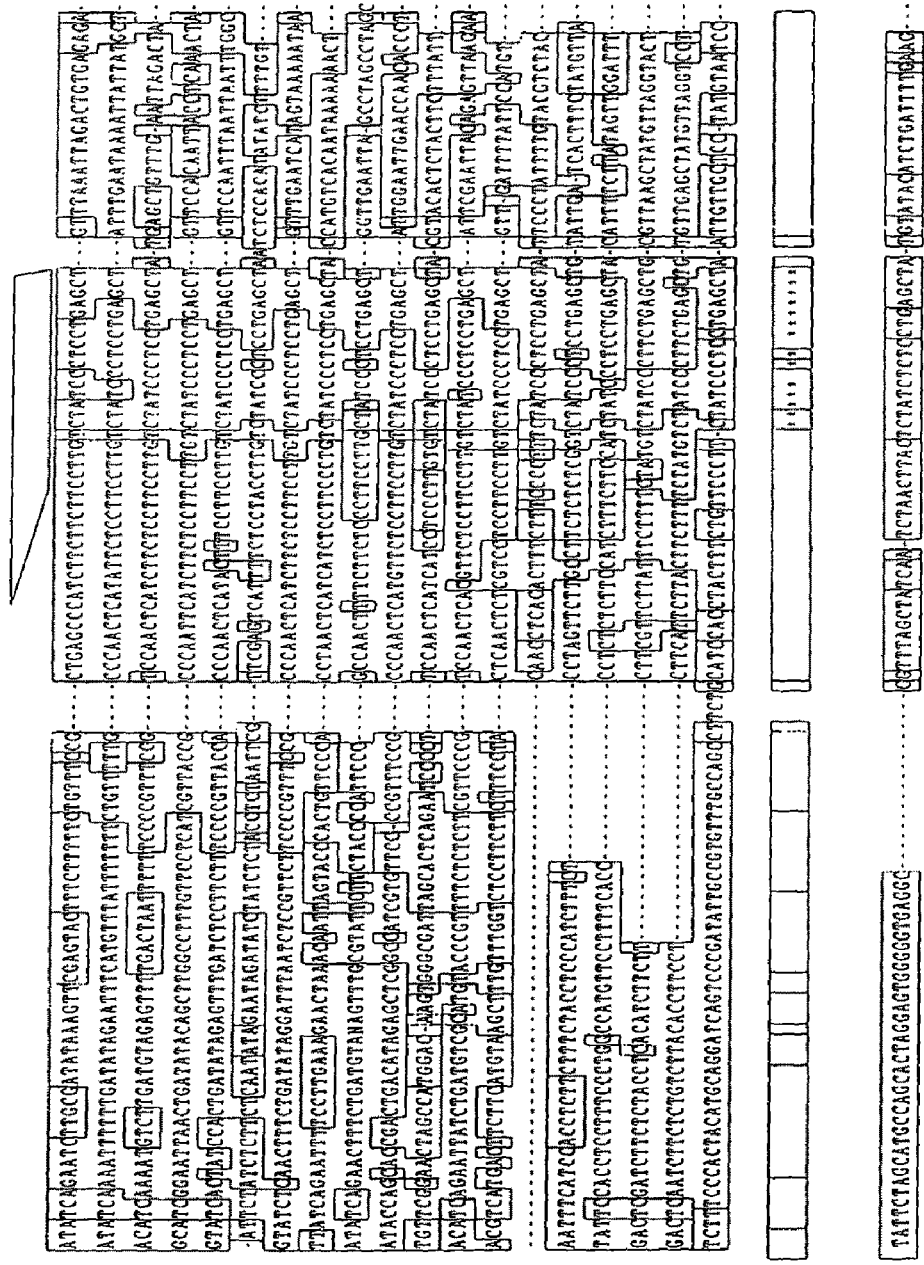
FIG. 3 shows a cleavage-independent miRNA-target interaction in flowering plants. (A) miR390-directed (SEQ ID NO: 1) cleavage of a target with a mismatch at position 10, but not one with a mismatch flanked by two G:U wobbles. The 5' complementary site of AtTAS3(SEQ ID NO: 92) was changed to the indicated sequences to mimic the sites found in *P. patens* TAS3 (SEQ ID NO: 287), or *P. taeda* TAS3 (SEQ ID NO: 38). Cap-labeled RNAs containing only the 5' complementary site were incubated with miR390-programmed wheat-germ lysate for the indicated times. Black and red arrowheads indicate the positions of uncut and cleaved substrate, respectively. (B) The 5' miR390 site of AtTAS3 resisted miR390-mediated cleavage because of conserved mismatches at positions 9-11. Cap-labeled AtTAS3 RNA encompassing both sites was incubated for the indicated times with wheat-germ lysate, with or without supplemental miR390. The sequences of 5' and 3' complementary site variants are shown paired to miR390(SEQ ID NO: 1). Red indicates the 5' site; blue indicates the 3' site; +, wild-type (SEQ ID NOs: 92 and 291, respectively, in order of appearance); Δ, disruptive mutation (SEQ ID NOs: 332 and 334, respectively, in order of appearance); R, repaired site (SEQ ID NO: 333). The positions of RNAs cleaved at the 3' and 5' site are indicated with blue and red arrowheads, respectively, while uncleaved substrate RNA is indicated by a black arrowhead. (C) The cleavage-refractory 5' miR390 complementary site of AtTAS3 was a potent inhibitor of miR390-mediated cleavage. The relative rates of in vitro target cleavage using 1 nM of radiolabeled AtTAS3-derived RNA containing only the wild-type 3' complementary site as substrate are plotted with varying concentrations of unlabeled RNA containing the wild-type 3' site (blue circles), the wild-type 5' site (red squares), the disrupted 3' site (black diamonds) or the disrupted 5' site (black triangles). The blue line shows the best fit to the data for the wild-type 3' site and indicates a $K_m$ for this site of 8.4 nM, whereas the red line shows the best fit to the data for the wild-type 5' site and indicates a $K_i$ for this site of 1.4 nM.
Figure 2:
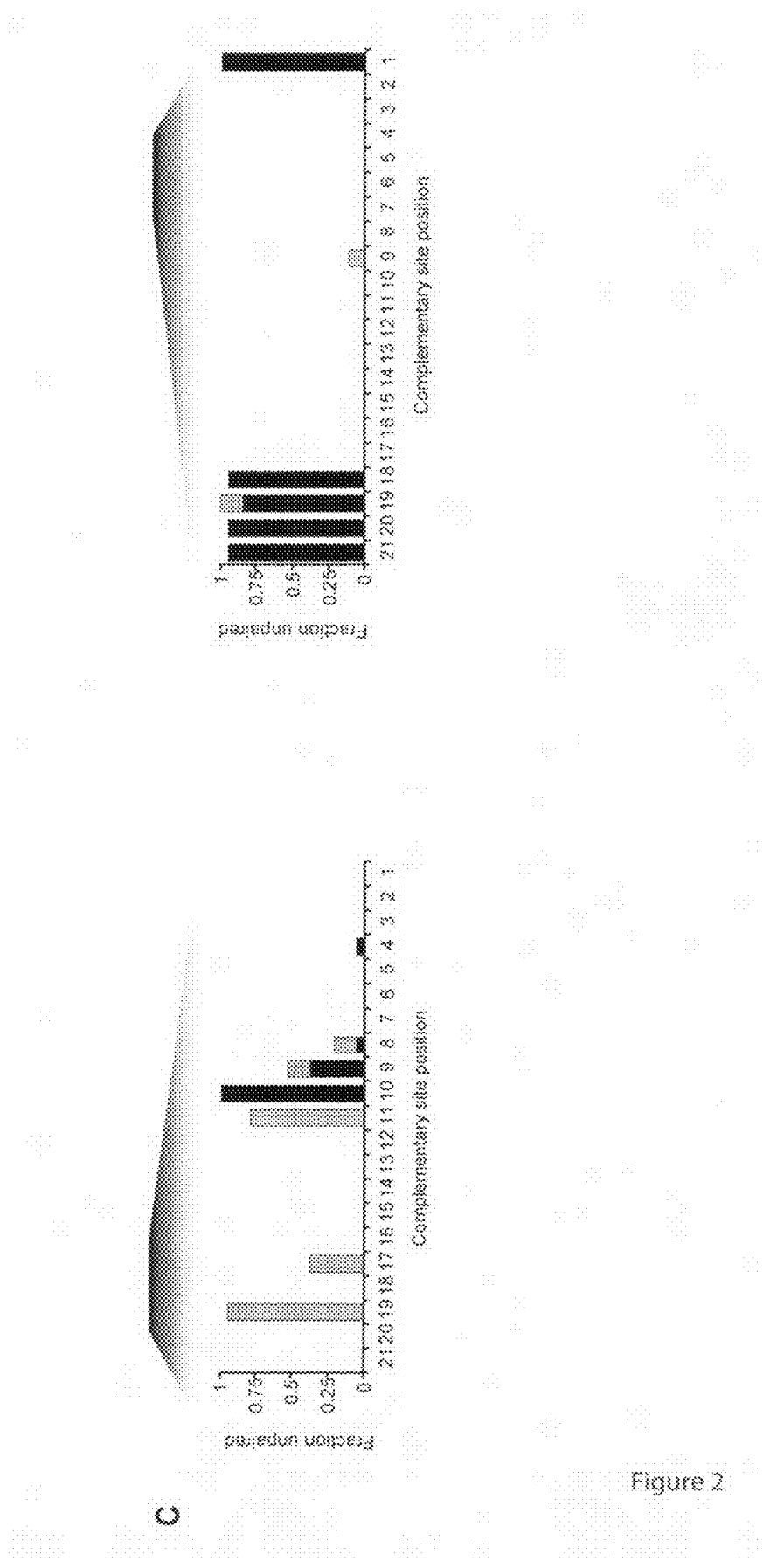
Figure 3:
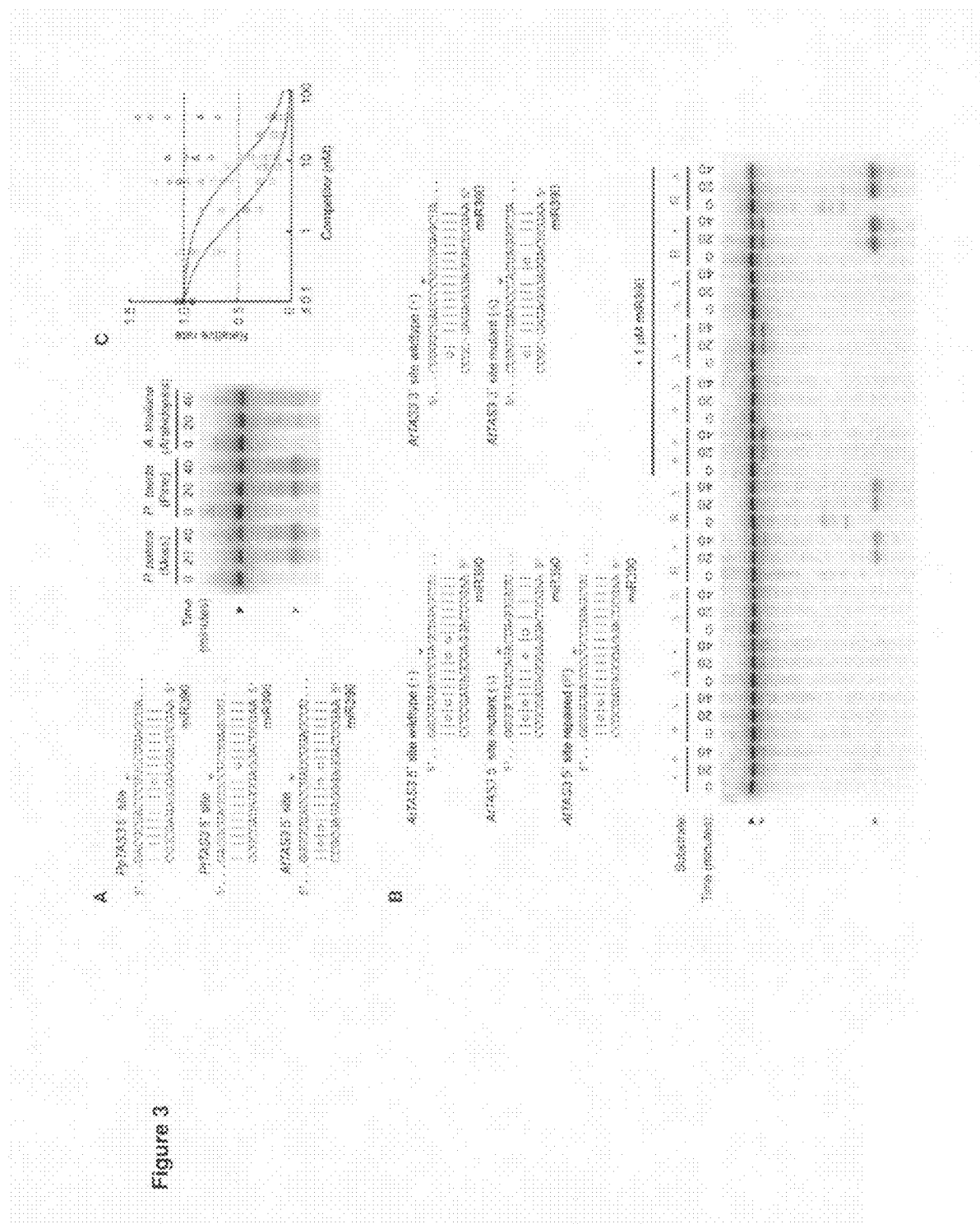
Figure 4:
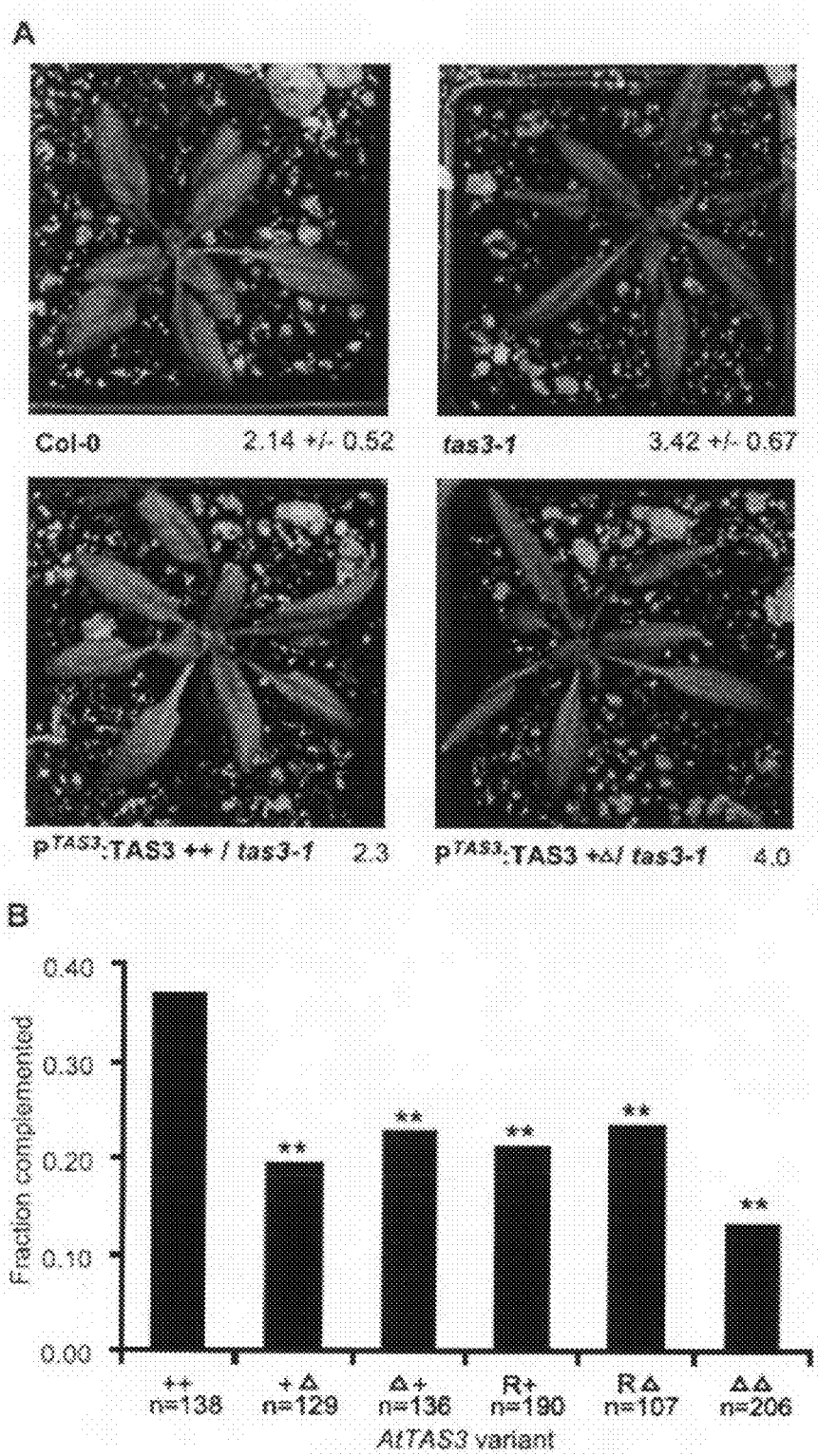
FIG. 4 shows that dual miR390 complementary sites are required for full AtTAS3 function. (A) Representative tas3-1 transformants. The mean and standard deviation of the length to width ratio of the sixth leaf is reported for Col-0 (n=40) and tas3-1 (n=41) control plants. Transformants with a ratio of less than 2.7 were scored as complementing (example at lower left), while those with ratios higher than 2.7 were scored as non-complementing (example at lower right). (B) The fraction of complemented tas3-1 primary transformants after transformation with the indicated variants of AtTAS3. The number (n) of independent T1 plants examined for each variant is listed below. The sequences of 5' and 3' site variants are as in FIG. 3. All statistically significant differences from the wildtype (p<0.01), as evaluated based on Chi-square goodness-of-fit tests, are indicated (**).
Figure 5:
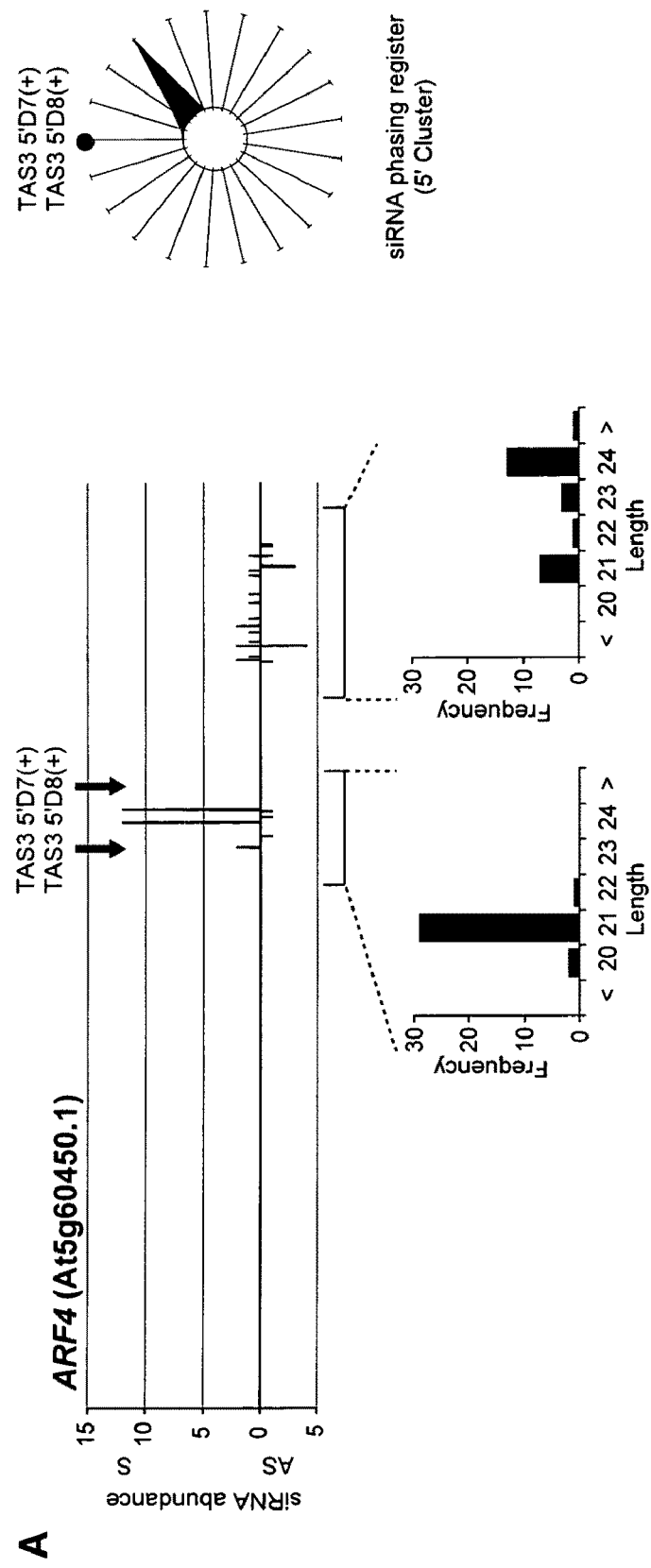
FIG. 5 demonstrates that multiple small RNA complementary sites correlate with siRNA production from *Arabidopsis* genes. (A) The positions, length distribution, and phasing register of *Arabidopsis* small RNAs corresponding to ARF4 mRNA are plotted as in FIG. 1. The most populated register contained 26 siRNAs (81.3%). The positions within the mRNA of the complementary sites to the tasiARFs TAS3 5'D7(+) and TAS3 5'D8(+) RNAs are indicated by black arrows. The length distributions of two distinct clusters of ARF4-derived small RNAs are indicated separately. (B) Small RNAs corresponding to the PPR mRNAs At1g63130.1 (SEQ ID NOs: 210, 4, 93, 2, 106 and 3, respectively, in order of appearance) and At1g63150.1(SEQ ID NOs: 211, 4, 94, and 2, respectively, in order of appearance) are plotted as in (A). Complementary sites for miR161.1, miR400, and TAS2 3'D6(−) are indicated by arrows and displayed below. Small RNAs that matched only one site in the *Arabidopsis genome* are represented by black, whereas small RNAs with more than one match to the genome are plotted in red, after normalizing for the number of matching loci (e.g., a sequence with 3 reads that matches the genome twice would contribute 1.5 counts to each locus). The most populated register for At1g63130.1 contained 96 (43.3%) unique and 78(56.1%) ambiguous siRNAs; 118(85%) of the unique and 149 (67%) of the ambiguous siRNAs fell in the same or adjacent registers as a complementary site. The most populated register for Atl g63150.1 contained 41 (39.9%) unique and 44 (24.6%) ambiguous siRNAs; 92 (51%) of the unique and 70 (68%) of the ambiguous siRNAs fell in the same or adjacent registers as a complementary site. The 13 other PPR genes with multiple small RNA complementary sites also gave rise to phased siRNAs (FIGS. 8A-8C).
Figure 5:
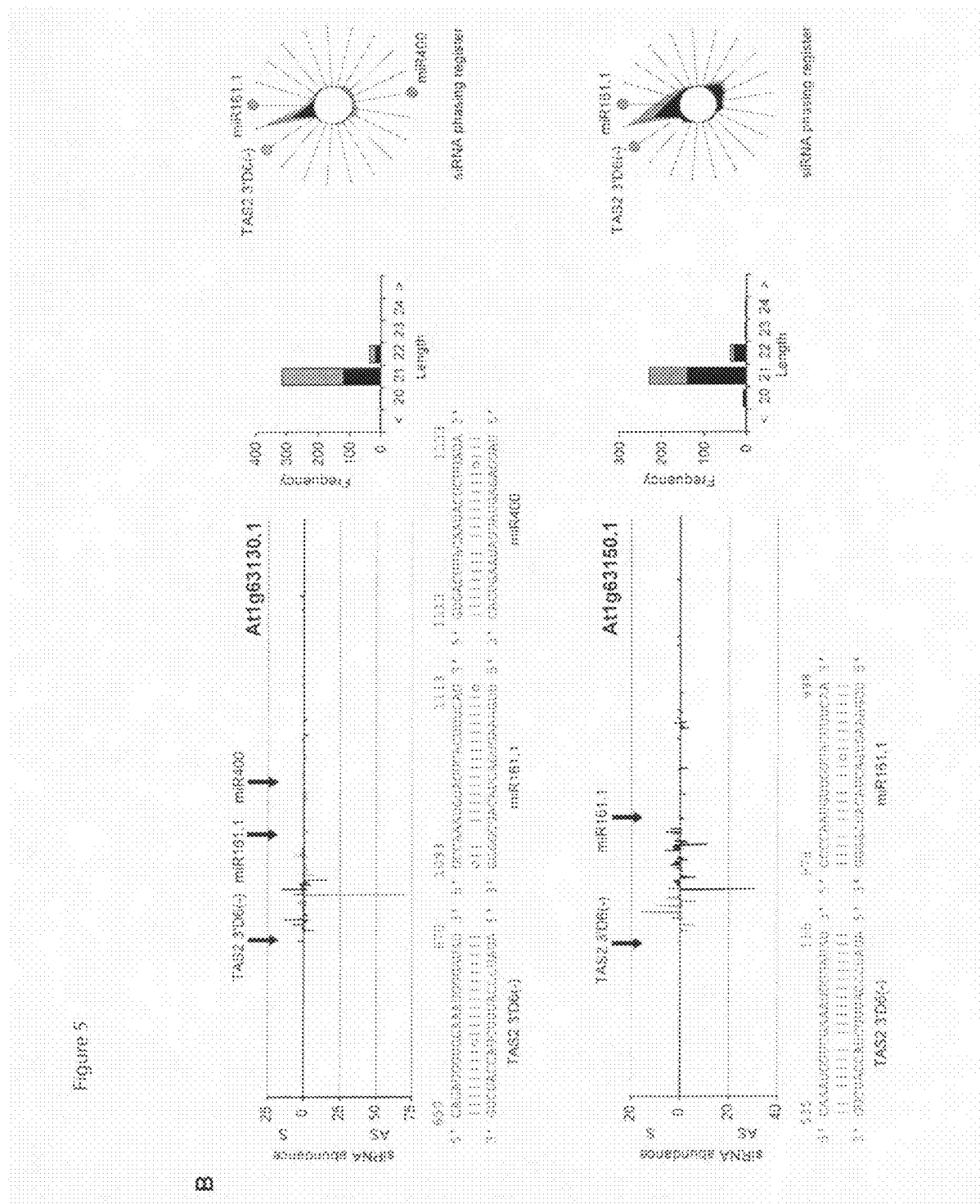

*Arabidopsis* TAS3 also contains dual miR390 complementary sites, the importance of which was highlighted by their conservation during seed-plant evolution and their requirement for efficient complementation of tas3 plants (FIGS. 2-4). The observation that tasiRNAs from such a wide breadth of plant lineages derive from loci falling between miR390 complementary sites suggests an ancient and broadly conserved hallmark of siRNA biogenesis. Curiously, the 5' miR390 complementary sites of flowering plant TAS3 loci consistently contained mismatches to miR390 at positions critical for target cleavage (FIG. 2C). These conserved mismatches at the center of the complementary site prevented miR390-mediated cleavage in vitro, yet they permitted efficient binding (FIG. 3). Taken together, these results indicated that this site functions independent of target cleavage in initiating production of AtTAS3 tasiRNAs (FIG. 6B), and there may be additional instances in which miRNA binding without cleavage could have important functions in plants.

Figure 9A:
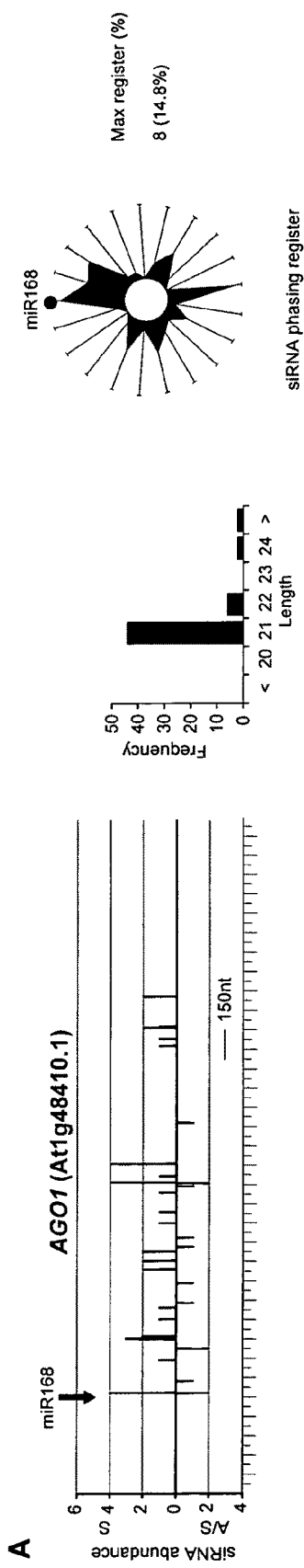
FIG. 9 shows production of siRNAs from known Arabidopsis miRNA targets. (A) The normalized number of sequenced small RNAs having their 5' residues at each position along the AGO1 (At1g48410.1) cDNA is plotted for both the sense (S) and antisense (A/S) strands. The position corresponding to the miR168 complementary site is indicated by an arrow. Length distributions and phasing of small RNAs are displayed as in FIGS. 8A-8C. The numbers and percentages of siRNAs in the most populated register (Max register) are indicated on the right. (B) miR393 targets TIR1 (At3g62980.1), AFB1 (At4g03190.1), AFB2 (At3g26810.1), AFB3 (At1g12820.1), and At3g23690 analyzed as in (A).
Figures 1, 9B:
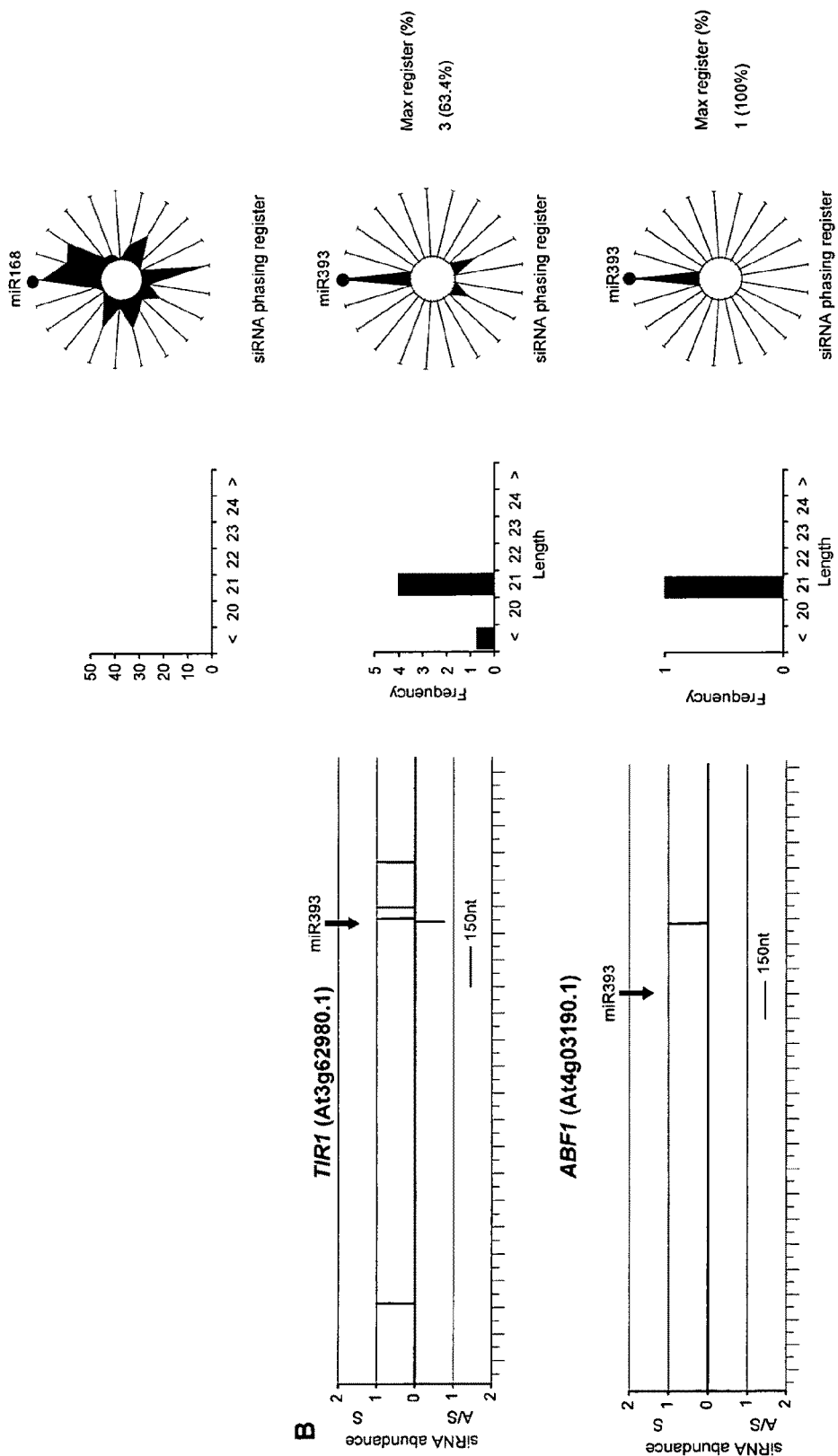
Figures 2, 9B:
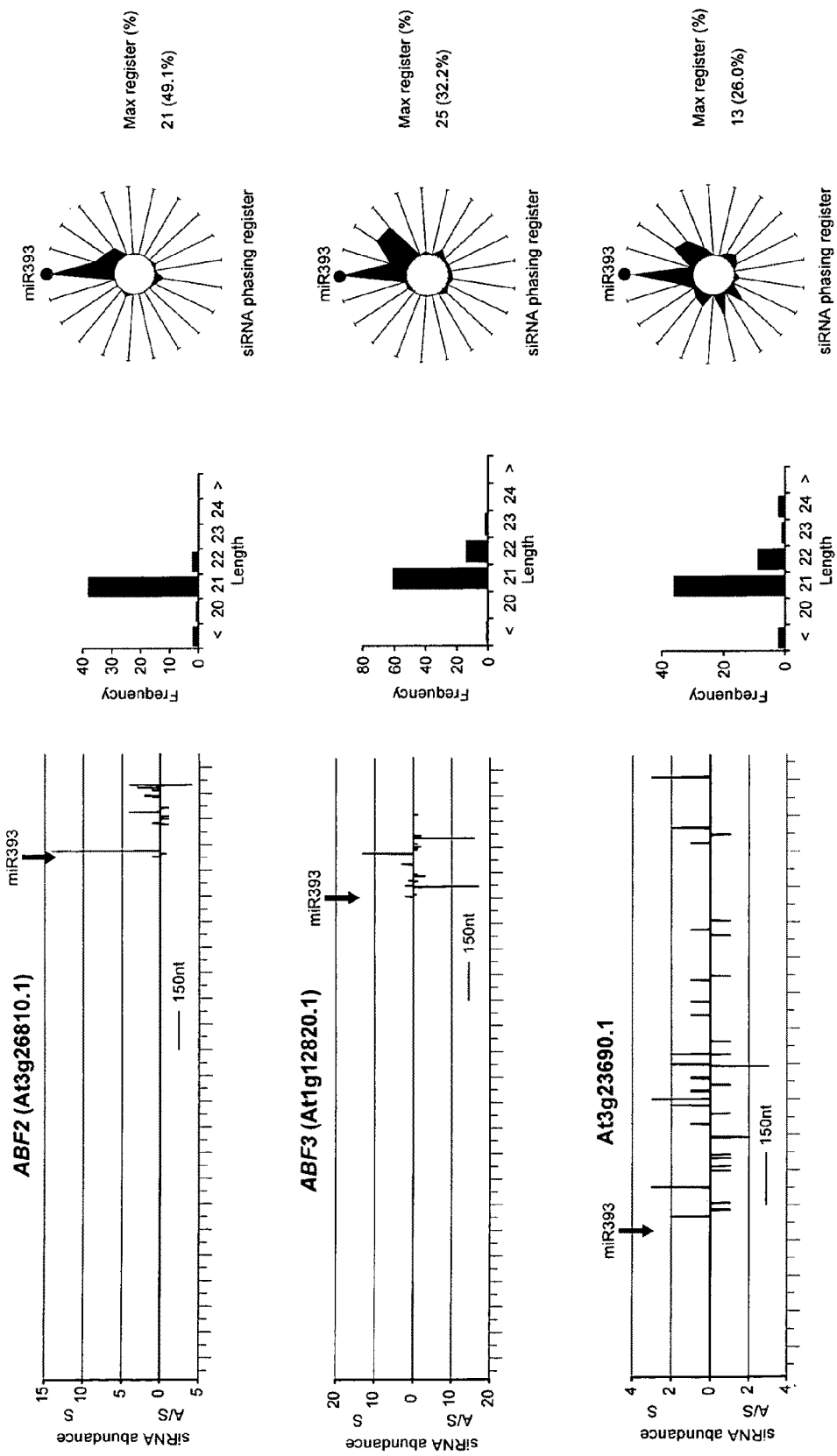

*Arabidopsis* TAS1a-c and TAS2 precursors are cleaved at a single site upstream of the segment converted to siRNAs (Allen et al., 2005). Similarly, some other singly-cleaved *Arabidopsis* miRNA targets give rise to siRNAs from the area downstream of miRNA-mediated cleavage (Lu et al., 2005; Ronemus et al., 2006; FIG. 9). We considered the possibility that these or other *Arabidopsis* miRNA targets might possess a second, previously unrecognized, miRNA complementary site. Even after drastically relaxing the stringency of target-site prediction to a level where past efforts have been unable to distinguish signal from noise, potential second sites were found in only three of 77 targets for which cleavage has been validated; none of the three were in AtTAS1a-c, AtTAS2, or the targets of miR168 and miR393 (data not shown). Thus, it was concluded that there are very few, if any, unknown second sites among the currently known miRNA targets. Perhaps these transcripts have another mechanism for downstream cleavage involving another type of ribonuclease. Alternatively, downstream cleavage might be bypassed; in principle, RDR6 could be recruited to the these transcripts by some other means, perhaps through a downstream binding element (FIG. 6C). In each of these cases (AtTAS1a-c, AtTAS2, and the targets of miR168 and miR393), the miRNA itself cannot be acting as a primer for RDR6-mediated RNA polymerization because all sequenced siRNAs arise exclusively from the region 3' of the miRNA complementary site.

Production of siRNAs upstream of a single miRNA complementary site has been observed for a highly transcribed gene designed to be a miRNA "sensor" (Parizotto et al., 2004). Work described herein points to a possible mechanism for how such upstream siRNAs might be triggered. Perhaps a rare, upstream non-specific cleavage coupled with efficient miRNA-mediated processing defines an initial RDR6 template in much the same way as dual miRNA-mediated cleavage does (FIG. 6D). Because the miRNA sensor is highly expressed, initial siRNAs would likely encounter additional transcripts and direct their cleavage upstream of the miRNA complementary site, thereby generating more RDR6 substrates and initiating a cascade resulting in the repression of the sensor. Indeed, the probability of rare, non-specific RNA cleavage occurring twice on the same mRNA molecule will increase as the abundance of that mRNA increases. For very highly expressed messages (such as those from a virus or an over-expressed transgene) background, non-specific cleavage events might generate a few fragments that lack both a 5' cap and a 3' poly-A tail (FIG. 6E). If, as observations described herein suggest, this type of RNA fragment is efficiently recognized by the RDR6/DCL4 pathway, the resulting siRNAs would target other copies of the highly expressed transcript, facilitating the formation of more fragments without caps and tails and initiating a cascade that ultimately silences the virus or transgene. This model postulates that the triggers for tasiRNA biogenesis and siRNA-mediated virus resistance are mechanistically similar—a postulate supported by the fact that a single Dicer-like protein, DCL4, is primarily responsible for both processes in wild-type *Arabidopsis* (Gasciolli et al., 2005; Xie et al., 2005; Yoshikawa et al., 2005; Bouche et al., 2006; Deleris et al., 2006). This two-hit model also provides a molecular mechanism that rationalizes threshold models proposed based upon earlier studies, which indicated that high initial expression levels of transgenes correlate with high frequencies of silencing initiation (Lindbo et al., 1993; Smith et al., 1994; Elmayan and Vaucheret, 1996). In this model, the plant cell detects over-abundant mRNA species by initiating silencing when a given transcript exceeds an abundance threshold whereby both the spontaneous production of fragments lacking caps and tails and the subsequent targeting of the transcript by the resulting siRNAs becomes likely. This hypothesis thus outlines a mechanistic model for the initial identification of aberrant/dangerous RNA by the silencing machinery, and further suggests that triggering of siRNA production can be directed to less abundant transcripts by the presence of dual miRNA complementary sites, as appears to occur for the miR390-targeted TAS loci.

EXEMPLIFICATION

Experimental Procedures

RNA Extractions

Total RNA from *Physcomitrella patens* was isolated from three wild-type samples cultivated on minimal media agar overlaid with cellophane discs under standard conditions: Protonemata (7 day culture, 22°, 16 hrs. light), protonemata+ young gametophores (14 day culture, 22°, 16 hrs. light), and gametophore+sporophytes (on media lacking $NH_4$-tartarate; 21 days at 22°, 16 hrs. light, followed by transfer to 15°, 8 hrs. light, with irrigation, for 39 days). Specimens were ground in 100 mM Tris-HCl pH 9.0, 2% hexadecyltrimethylammonium bromide, 0.5% SDS, 2% polyvinyl pyrrolidone 40, 5 mM EDTA, 10 mM β-mercaptoethanol. Samples were then phenol-chloroform extracted, ethanol precipitated, resuspended in 250 mM NaCl, and placed on ice for 20 minutes to precipitate carbohydrates. After centrifugation, the supernatant was ethanol precipitated to recover total RNA.

Small RNA Sequencing and Data Analysis

Construction of small RNA cDNA libraries was performed as described (Lau et al., 2001) and adapted for pyrosequencing (Supplemental Experimental Procedures). After phenol/chloroform extraction and native PAGE purification, 5 μg of purified PCR products for each library was delivered to 454 Life Sciences (Branford, CT, USA) for pyrosequencing. After discarding small RNAs that matched the *P. patens* chloroplast genome or the sense polarities of the nuclear 5S, 5.8S, 18S, or 26S rRNAs, the sequenced small RNAs were matched to the ~5.4 million *P. patens* WGS traces available at the time of analysis. Matching RNAs were classified as repetitive or non-repetitive (Table 2, Supplemental Experimental Procedures). PpTAS1-4 were found by using an algorithm that searched for clusters of non-repetitive small RNAs from both the sense and antisense strand of WGS traces whereby a significant fraction of the small RNAs were in phase with each other (in the same or adjacent registers, accounting for the 2-nt offset expected between the sense and antisense strands). Homologs of *Arabidopsis* TAS3(FIG. 2B, Table 3) were found by searching the est_others database for EST sequences that contained a sequence highly similar to 5'-TTCTTGACCTTGTAAGGC-CTTTTCTTGACCTTGTAAGACCCC-3' (SEQ ID NO: 33) (representing the two tasiARFs).

5'-RACE

Cleaved transcripts were detected using 5'-RACE (Llave et al., 2002).

Oligonucleotides

Oligos used for library preparation, RACE, mutagenesis, and transcription are listed in the Supplemental Experimental Procedures.

In vitro Assays

Wheat-germ extract was prepared as previously described (Tang et al., 2003). Templates for in vitro transcription were made by PCR from constructs used for tas3-1 complementation (pART27-AtTAS3; Adenot et al., 2006). All RNAs were gel-purified, and substrate RNA was radiolabeled by capping, using guanylyl transferase (Ambion, Houston, Tex.) and alpha-$^{32}$P GTP. Cleavage reactions contained 50% wheat germ extract (v/v), 5 mM DTT, 0.1 U/μl RNasin (Promega), 25 mM phosphocreatine, 1 mM ATP, 40 mM KOAc, and 0.03 μg/μl creatine kinase. Extract was incubated with buffer±1 μM phosphorylated miR390 for 20 minutes at 26° C., then added to 10,000 cpm of RNA (~5 fmol) per reaction. Reactions were stopped by addition of 25 volumes of TRI reagent (Ambion, Houston, Tex.) at the indicated time points, followed by RNA extraction and PAGE analysis. For competition assays, extract was preincubated for 10 minutes at 26° C. then added to labeled substrate (1 nM final) premixed with unlabeled competitor. Percent cleavage was calculated as the density of the cleaved band divided by the sum of the densities of the cleaved and full-length bands, and initial rates were calculated by regression. For 3' wildtype competition, data were fit to the Michaelis-Menten equation, correcting for the fraction of total. RNA that was radiolabeled: $V_{obs}=(1\ nM/1\ nM+X\ nM)\cdot(v_{max}[1+X]\ nM)/(K_m+[1+X]\ nM)$, where X was the concentration of unlabeled 3' wildtype competitor. For 5' wildtype competition, data were fit for competitive inhibition: $V_{obs}=(v_{max}\cdot 1\ nM)/(K_m\cdot(1+X/K_i)+1\ nM)$, where X was the concentration of the unlabeled 5' wildtype competitor.

tas3-1 Complementation

Variants of pART27-AtTAS3 (FIG. 3B) were produced using QuickChange mutagenesis (Stratagene, La Jolla, Calif.), and transformed into tas3-1 plants (Adenot et al., 2006). After 23-26 days of growth at ~22° in 16 hours light, 8 hours dark, the length-to-width ratio of the sixth rosette leaf was determined for each transformant. Non-transformed wild-type and tas3-1 plants gave ratios of 2.14+/−0.52 and 3.42+/−0.67, respectively. Therefore, we classified transformants as "complementing" if this ratio was less than 2.7, recognizing that 17% of non-transformed tas3-1 plants also scored as complemented, which represents the background of the assay.

Accessions

The consensus sequences of PpTAS1-4 were deposited in Genbank (BK005825-BK005828). 127,135 unique, genome-matched *P. patens* and 340,114 unique, genome-matched *Arabidopsis* small RNAs were deposited with the Gene Expression Omnibus (GSE5103 and GSE5228, respectively). The sequences of the *P. patens* and *Arabidopsis* small RNAs analyzed in this study are also available in Supplemental Databases 1 and 2, respectively.

Supplemental Experimental Procedures

Pyrosequencing of Small RNAs

The small RNA sequencing protocol of (Lau et al., 2001) was adapted in the following aspects: Primary reverse-transcriptase polymerase chain reactions (RT-PCR) were stopped during the linear phase of amplification (as determined by analysis of samples derived from consecutive cycles) and used as template in a second PCR, using 5'-phosphorylated oligos and substituting the 5' oligo to 5'-ATCGTAGGCAC-CTGAGA-3' (SEQ ID NO: 34), again taking care to stop the PCR during the linear phase of amplification. The change in primer sequence replaced the AAA triplet proximal to the insert with AGA, thereby preventing a homopolymeric run that might have decreased accuracy of sequencing. The phosphorylation of the oligos facilitated blunt-end ligation of the primer-binding sequences needed for emulsion PCR and sequencing. Amplification was not performed beyond the linear phase because denaturation without synthesis could prevent rare sequences from migrating as perfectly double-stranded DNA during the subsequent gel purification.

Data Analysis

Pyrosequencing reads that did not have a perfect match to the 11 nucleotides of both the 5' and 3' adapters that immediately flanked the inserts were discarded. Inserts containing ambiguous nucleotides or that were less than 15 or greater than 28 nucleotides in length were also discarded. This process retained 4,016 di-deoxy-derived and 873,631 pyrosequencing-derived P. patens small RNA reads (Table 2). The datasets were then merged, in the process removing small RNAs containing matches to the P. patens chloroplast genome (AP005672) or to the sense polarities of the nuclear 5S, 5.8S, 18S, or 26S rRNAs, leading to the 561,102 (214,996 unique) sequences (Table 2). Matching of the small RNAs to whole-genome shotgun (WGS) sequence traces was accomplished by a process utilizing the script "query_tracedb.pl" (see the National Center for Biotechnology Information (NCBI) Web site, Traces) to access the NCBI trace archive and detect perfect sense and antisense hits by string matching. Each of the approximately 5.4 million such traces available at the time of analysis (October, 2005) were compared against each of the 214,996 non-redundant, filtered small RNAs. The analysis was fragmented into 271 jobs of 20,000 WGS traces each. To escape the computational burden of reporting each WGS match for small RNAs arising from highly repetitive genomic loci, the number of WGS matches for any given small RNA during each 20,000 WGS job was capped at 12, with subsequent matches during that job being ignored. P. patens small RNAs matching repetitive genomic DNA were defined as those that either reached the 12 matches per 20,000 WGS traces cap in more than 33% of the jobs or those that had more than 1,000 total matched WGS traces. 127,135 of the 214,996 non-redundant filtered small RNAs had at least one match within the WGS data, with 15.7% (19,974) of the matched small RNAs being classified as repetitive (Table 2). Sequences and isolation frequencies of the 127,135 unique, genome-matched P. patens small RNAs have been deposited with the Gene Expression Omnibus (GSE5103).

TABLE 2

Sequenced small RNAs from the moss *Physcomitrella patens*

| Dataset | Number of reads | Unique small RNAs |
|---|---|---|
| Di-deoxy sequenced | 4,016 | |
| Pyrosequenced | 873,631 | |
| Combined and filtered small RNAs | 561,102 | 214,996 |
| Matched to one or more WGS traces | 384,441 | 127,135 |
| Highly repetitive matches to WGS traces | 39,975 | 19,974 |
| Non-repetitive matches to WGS traces | 344,466 | 107,161 |

TABLE 3

Seed plant homologs of AtTAS3

| Accession | Species | Aligned Coordinates[a] |
|---|---|---|
| BP947370 | Bruguiera gymnorhiza | 272-355, 356-439, 440-513, 514-576 |
| CK652751 | Manihot esculenta | 159-227, 228-311, 312-385, 386-448 |
| DT498974 | Populus trichocarpa | 212-274, 275-352, 353-426, 427-489 |
| CN490861 | Malus domestica | 121-214, 215-298, 299-372, 373-435 |
| BE330988 | Glycine max | 157-255, 256-339, 340-413, 414-476 |
| BX838290 | Arabidopsis thaliana | 156-241, 242-325, 326-399, 400-462 |
| CX663477 | Citrus paradisi x Poncirus trifoliata | 235-307, 308-391, 392-465, 466-528 |
| CO077318 | Gossypium raimondii | 287-385, 386-469, 470-543, 544-606 |
| CA795323 | Theobroma cacao | 108-204, 205-288, 289-361, 362-424 |
| DT025007 | Vitis vinifera | 201-280, 281-364, 365-437, 438-500 |
| BF479835 | Mesembryanthemumcrystallinum | 145-221, 222-305, 306-379, 380-442 |
| AJ797948 | Antirrhinum majus | 239-340, 341-424, 425-498, 499-561 |
| DV105041 | Lycopersicon esculentum | 237-335, 336-419, 420-493, 494-556 |
| BF264964 | Hordeum vulgare | 285-376, 377-460, 461-471, 472-534 |
| AU100890 | Oryza sativa | 282-376, 377-460, 461-513, 514-576 |
| CN010916 | Triticum aestivum | 331-411, 412-495, 496-548, 549-611 |
| CA145655 | Saccharum officinarum | 177-272, 273-356, 357-388, 389-451 |
| CD464142 | Sorghum bicolor | 288-383, 384-467, 468-499, 500-562 |
| BE519095 | Zea mays | 123-230, 231-314, 315-387, 388-450 |
| DR112999 | Pinus taeda | 227-335[b], 427-510, 511-574, 575-637 |

[a]The global alignment shown in FIG. 2 was generated by combining four CORE-scored ClustalW alignments of the indicated sub-sequences.
[b]A 91 nucleotide region (336-426) of the *Pinus taeda* TAS3 homolog was not alignable.

Databases

P. patens genomic data was obtained from the NCBI trace archive in October, 2005 as described above. Analyses of Arabidopsis small RNAs utilized the TAIR version 6 release of the Arabidopsis genome and cDNA set, released Nov. 8, 2005.

Supplemental Databases

Database S1 FASTA formatted file of P. patens small RNAs corresponding to PpTAS1-4. Headers: Unique identifier|number of times sequenced|corresponding locus or loci. The number of times sequenced is out of a total of 384,441 reads (representing 127,135 different RNAs; Gene Expression Omnibus accession GSE5103) that matched the P. patens whole-genome shotgun traces (Table 2).

Database S2 FASTA formatted file of Arabidopsis small RNAs corresponding to AtTAS3, ARF4, AGO1, TIR1, ABF1-3, At3g23690.1, and 15 PPR genes. Headers: Unique identifier|number of times sequenced|number of matches to the Arabidopsis genome|normalized frequency|corresponding locus or loci. The normalized frequency is the number of times sequenced divided by the number of matches to the genome. The number of times sequenced is out of a total of 887,266 reads (representing 340,114 unique RNAs) from wild-type Col-0 *Arabidopsis* that match the nuclear, plastid, or mitochondrial genomes (Rajagopalan, Vaucheret, and Bartel, submitted; Gene Expression Omnibus accession GSE5228).

Detection of Cleavage Products by RT-PCR cDNA specific for PpTAS1 or AtTAS3 was generated and sequenced using RNA ligase mediated RT-PCR from total RNA per the manufacturer's (Generacer; Invitrogen, Carlsbad, Calif., USA) instructions, except for the omission of phosphatase and tobacco acid pyrophosphatase treatment of the RNA. For PpTAS1, an oligo corresponding to the region downstream of the 3' miR390 complementary site was used to prime first-strand cDNA synthesis (5'-GTATGTGACTC-CATTACATCAACTGCA-3'; SEQ ID NO:11), and amplification of the cDNAs was achieved with a nested oligo (5'-TATCACCGCCGCCTGTGGCCGGCTAAGA-3' SEQ ID NO:12). For AtTAS3, an oligo corresponding to the region between the two miR390 complementary sites was used to prime first-strand cDNA synthesis (5'-GAGGTAGAGATA-GATATCTATTCTATATT-3' SEQ ID NO:13), and amplification of the cDNAs was achieved with a nested oligo (5'-AGAAAGAGATGGGGTCTTACAAGGTCAA-3' SEQ ID NO:14).

In vitro RNA Cleavage and Competition Assays, and Construction of Mutagenized AtTAS3 Derivatives All RNA substrates were prepared by transcription of PCR-based templates amplified from pART27-AtTAS3 (Adenot et al., 2006) or mutagenized derivatives thereof. Complementation of tas3-1 plants was also accomplished using pART27-AtTAS3 and its mutagenized derivatives, which were made by site-directed mutagenesis using Quick-Change-XL (Stratagene, La Jolla, Calif.) with the following oligonucleotide pairs:

```
5'site mutants
AtTAS3 5' Δ forward:
                                               SEQ ID NO: 15
5'-CAATGATAAAGCGGTGTTATCATACTAGTGATTTTAGTCGGATTTTTTC-3'

AtTAS3 5' Δ reverse:
                                               SEQ ID NO: 16
5'-GAAAAAATCCGACTAAAATCACTAGTATGATAACACCGCTTTATCATTG-3'

AtTAS3 5' Δ repair forward:
                                               SEQ ID NO: 17
5'-CAATGATAAAGCGGTGTTATCCCTCCTGAGCTTTTAGTCGGATTTTTTC-3'

AtTAS3 5' repair reverse:
                                               SEQ ID NO: 18
5'-GAAAAAATCCGACTAAAAGCTCAGGAGGGATAACACCGCTTTATCATTG-3'

Physcomitrella patens TAS3 5' forward:
                                               SEQ ID NO: 19
5'-CAATGATAAAGCGACGCTACCCTTCCTGAGCTATTAGTCGGATTTTTTC-3'

Physcomitrella patens TAS3 5' reverse:
                                               SEQ ID NO: 20
5'-GAAAAAATCCGACTAATAGCTCAGGAAGGGTAGCGTCGCTTTATCATTG-3'

Pinus taeda TAS3 5' forward:
                                               SEQ ID NO: 21
5'-CAATGATAAAGCGACGCTATCCCCTCTGAGCTTTTAGTCGGATTTTTTC-3'

Pinus taeda TAS3 5' reverse:
                                               SEQ ID NO: 22
5'-GAAAAAATCCGACTAAAAGCTCAGAGGGGATAGCGTCGCTTTATCATTG-3'
3' site mutants
AtTAS3 3' Δ forward:
                                               SEQ ID NO: 23
5'-CTCCTACCTTGTCTATCCCACTAGTGCTAATCTCCACATATATC-3'

AtTAS3 3' Δ reverse:
                                               SEQ ID NO: 24
5'GATATATGTGGAGATTAGCACTAGTGGGATAGACAAGGTAGGAG-3'
```

The following primers were used to produce T7 templates by PCR for the specified substrates:

```
miR390 dual-site substrate:
                                               SEQ ID NO: 25
forward: 5'-GCTAATACGACTCACTATAGGGCATTAAGGAAAACATAACC-3'

SEQ ID NO: 26
reverse: 5'-CAGTGTGATGGATATCTGCAG-3' miR390 5' substrate:
                                               SEQ ID NO: 27
forward: 5'-GCTAATACGACTCACTATAGGGCATTAAGGAAAACATAACC-3'

SEQ ID NO: 28
reverse: 5'-GAGAATAATGAAATGCATC-3'
```

-continued

```
miR390 5' competitor:
                                              SEQ ID NO: 29
forward: 5'-GCTAATACGACTCACTATAGGGATCCGCTGTGCTGAGAC-3'

SEQ ID NO: 30
reverse: 5'-GAGAATAATGAAATGCATC-3' miR390 3' substrate and competitor:
                                              SEQ ID NO: 31
forward: 5'-GCTAATACGACTCACTATAGGGAATAGATATCTATCTCTACCTC-3'

SEQ ID NO: 32
reverse: 5'-CAGTGTGATGGATATCTGCAG-3'
```

Results

Endogenous Small RNAs from Moss

Small RNA was prepared from three developmentally staged samples of the moss *Physcomitrella patens* and sequenced using either the standard di-deoxy method (Lau et al., 2001) or a recently described pyrosequencing technology (Margulies et al., 2005) to yield a total of 561,102 small RNA reads, representing 214,996 unique sequences (Table 2). These sequences were compared to the 5.4 million traces available at the time of the analysis from the *P. patens* whole-genome shotgun (WGS) project. A total of 127,135 unique small RNA sequences, represented by 384,441 reads, had at least one perfect match to the WGS traces (Table 2). The remaining sequences that did not perfectly match any WGS trace were not analyzed further and were presumed to be either sequences from genomic regions missed by the WGS project, sequencing errors, or unclassified contaminant sequences. Some of the genome-matched sequences were classified as miRNAs. These accounted for 42% of the genome-matched reads, leaving 58% that did not appear to arise from loci with the characteristics of known miRNAs, suggesting that, similar to *Arabidopsis, P. patens* might express many endogenous siRNAs. Among these potential siRNAs, 18% (39,975 reads representing 19,974 sequences) matched more than 1,000 traces, which would correspond to more than 100 endogenous loci; these were designated as repetitive small RNAs (Table 2). Once a genome assembly is available it will be interesting to evaluate whether repeat elements are more or less likely than other regions of the genome to give rise to moss small RNAs.

The Antiquity of tasiRNAs

The first characterized tasiRNA loci showed no sign of conservation beyond *Arabidopsis* (Peragine et al., 2004; Vazquez et al., 2004b). However, two related tasiRNAs from the AtTAS3 locus, required for the proper timing of vegetative development and regulation of organ polarity (Adenot et al., 2006; Fahlgren et al., 2006; Garcia et al., 2006; Hunter et al., 2006), are conserved among diverse flowering plants (Allen et al., 2005; Williams et al., 2005). To explore the possibility that tasiRNAs might have emerged much earlier in plant evolution, the non-repetitive WGS moss traces were searched for clustered small RNA hits in both sense and antisense orientation, wherein a significant fraction were phased in ~21-nt increments. Four candidate tasiRNA loci were found (PpTAS1-4), one of which was represented by 15,730 reads-4.1% of all of the non-repetitive, genome-matched reads (FIG. 1A). Indeed, a cDNA corresponding to this locus (PpTAS1) had previously been suspected of being a tasiRNA precursor based on the sequencing of three corresponding small RNAs (Arazi et al., 2005).

Figures 1, 7:
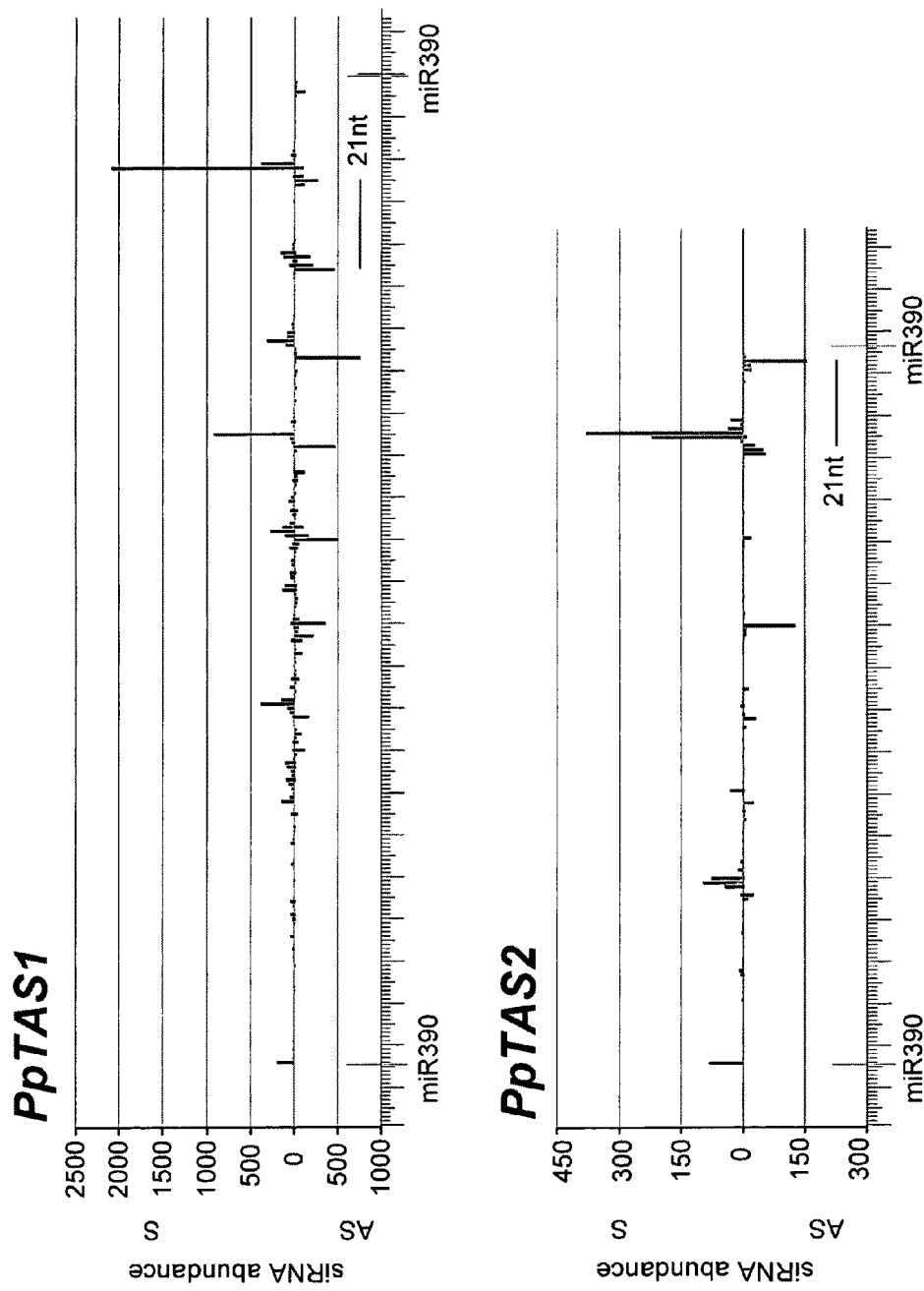
FIG. 7 shows high-resolution versions of graphs shown in FIGS. 1 and 2A. Identical small RNAs between PpTAS1 and PpTAS2 are indicated by red, and small RNAs identical between PpTAS2 and PpTAS3 are indicated by green. PpTAS4 does not express any small RNAs in common with the other three P. patens TAS loci, and, other than the miR390 complementary sites, none of the four loci share any detectable homology to AtTAS3 (data not shown).
Figures 2, 7:
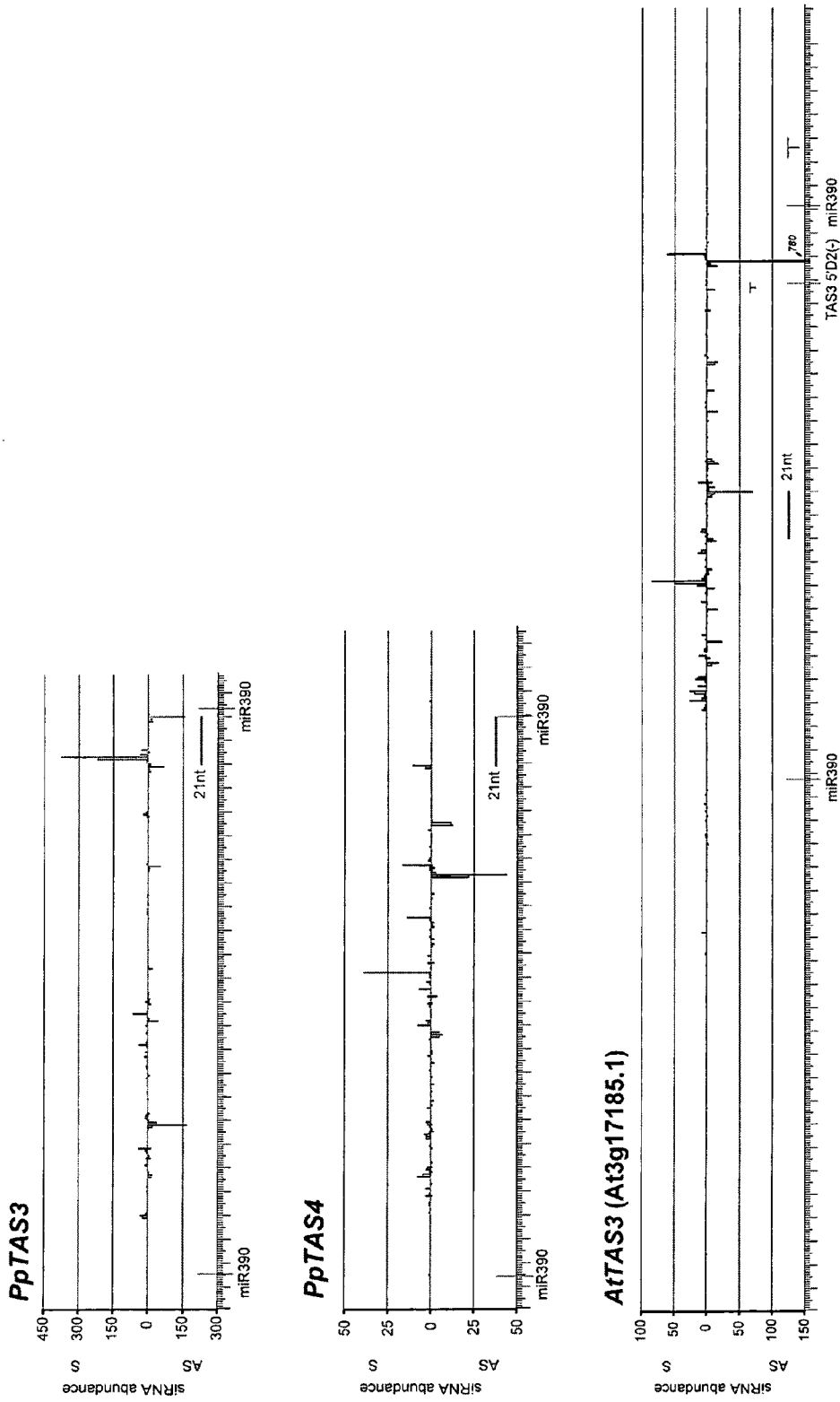
Figures 1, 8A:
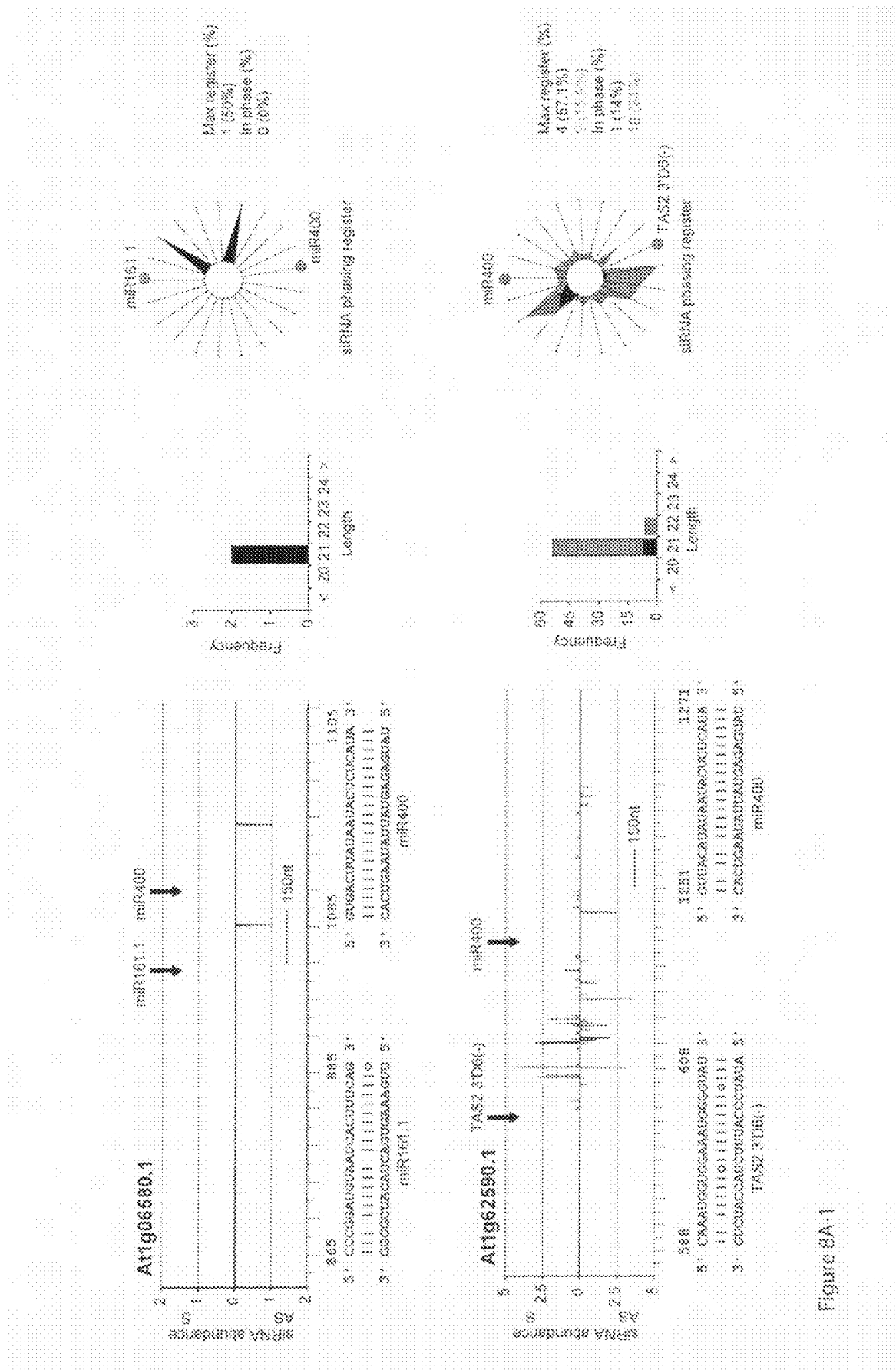
Figures 2, 8A:
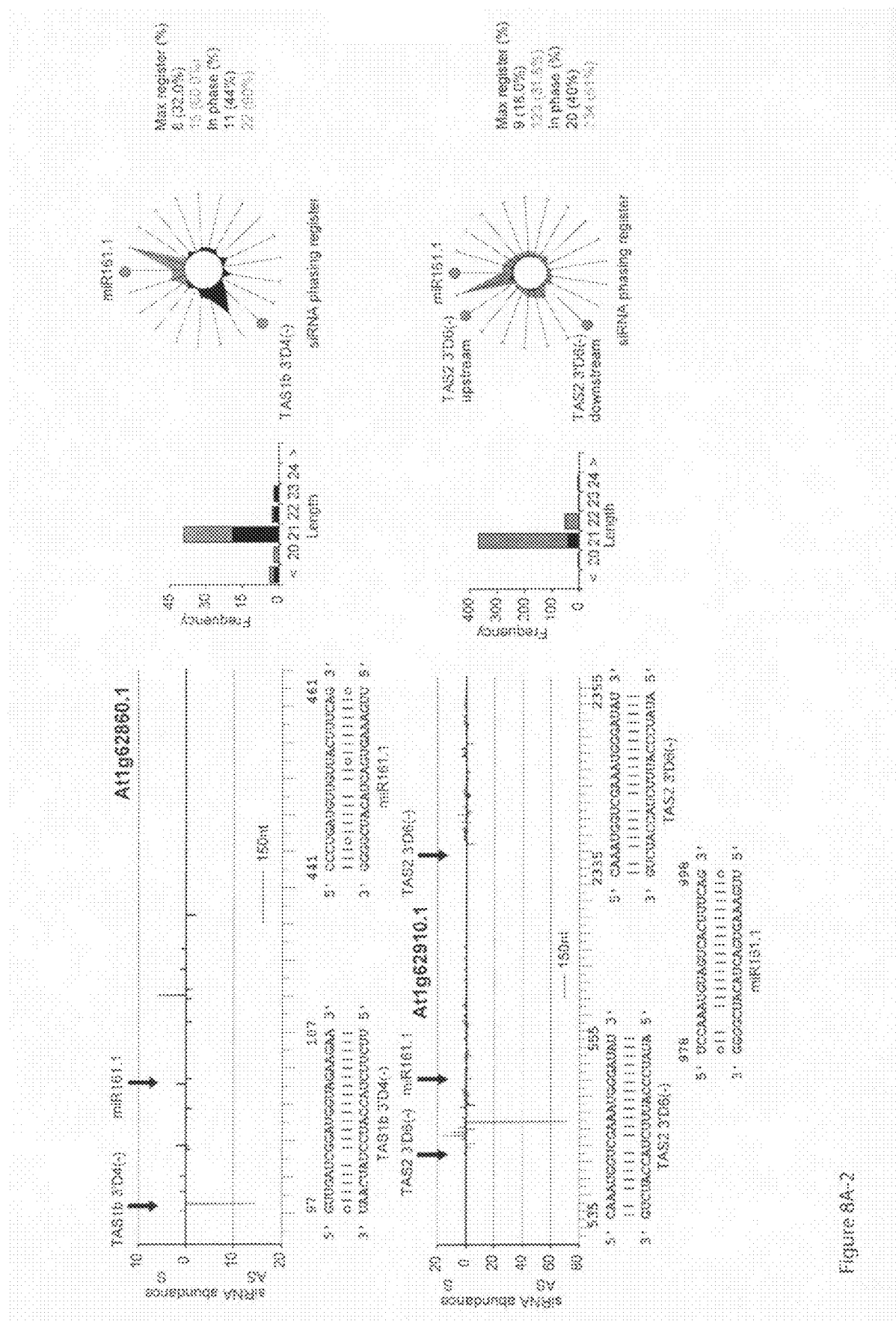
Figures 3, 8A:
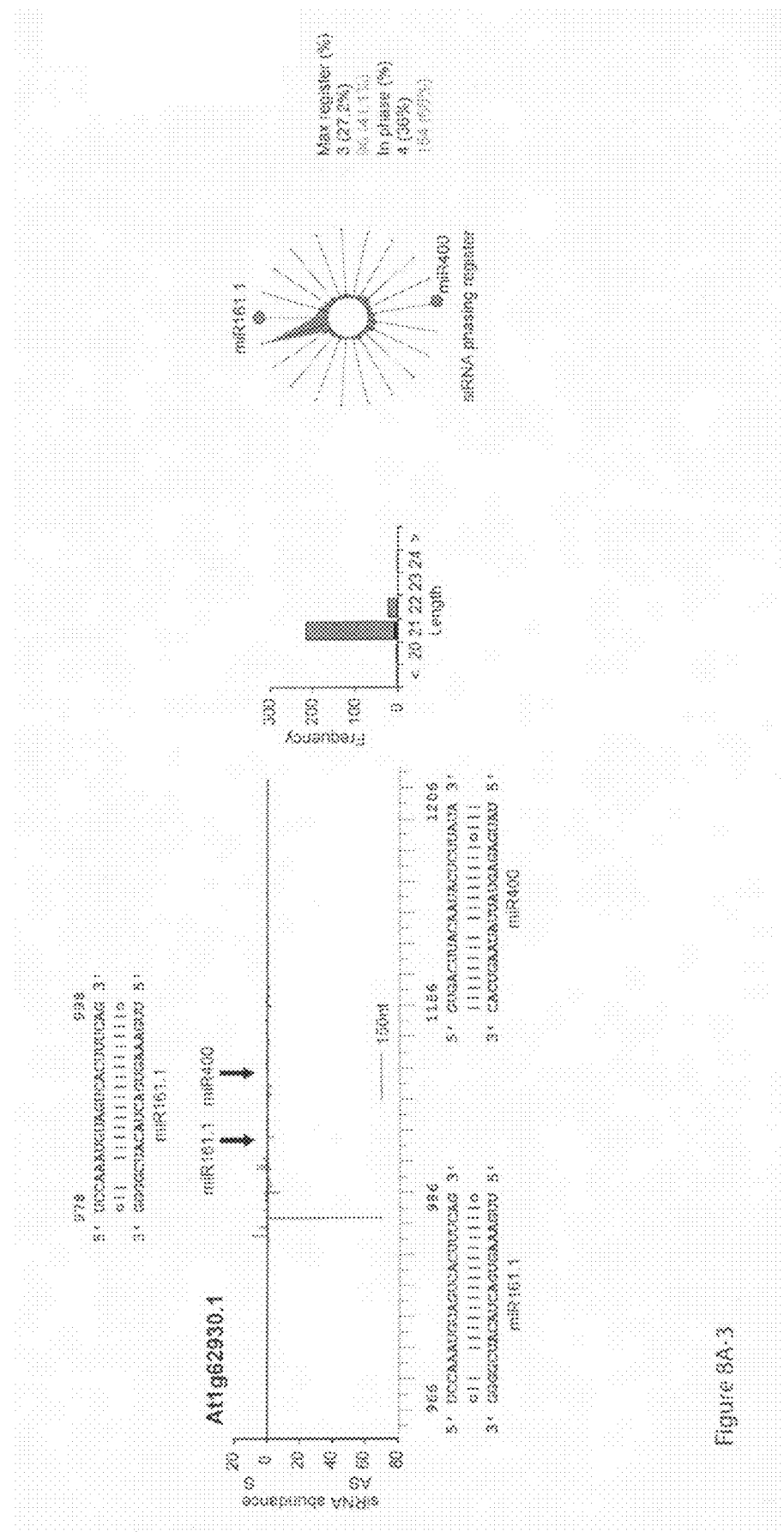
Figures 1, 8B:
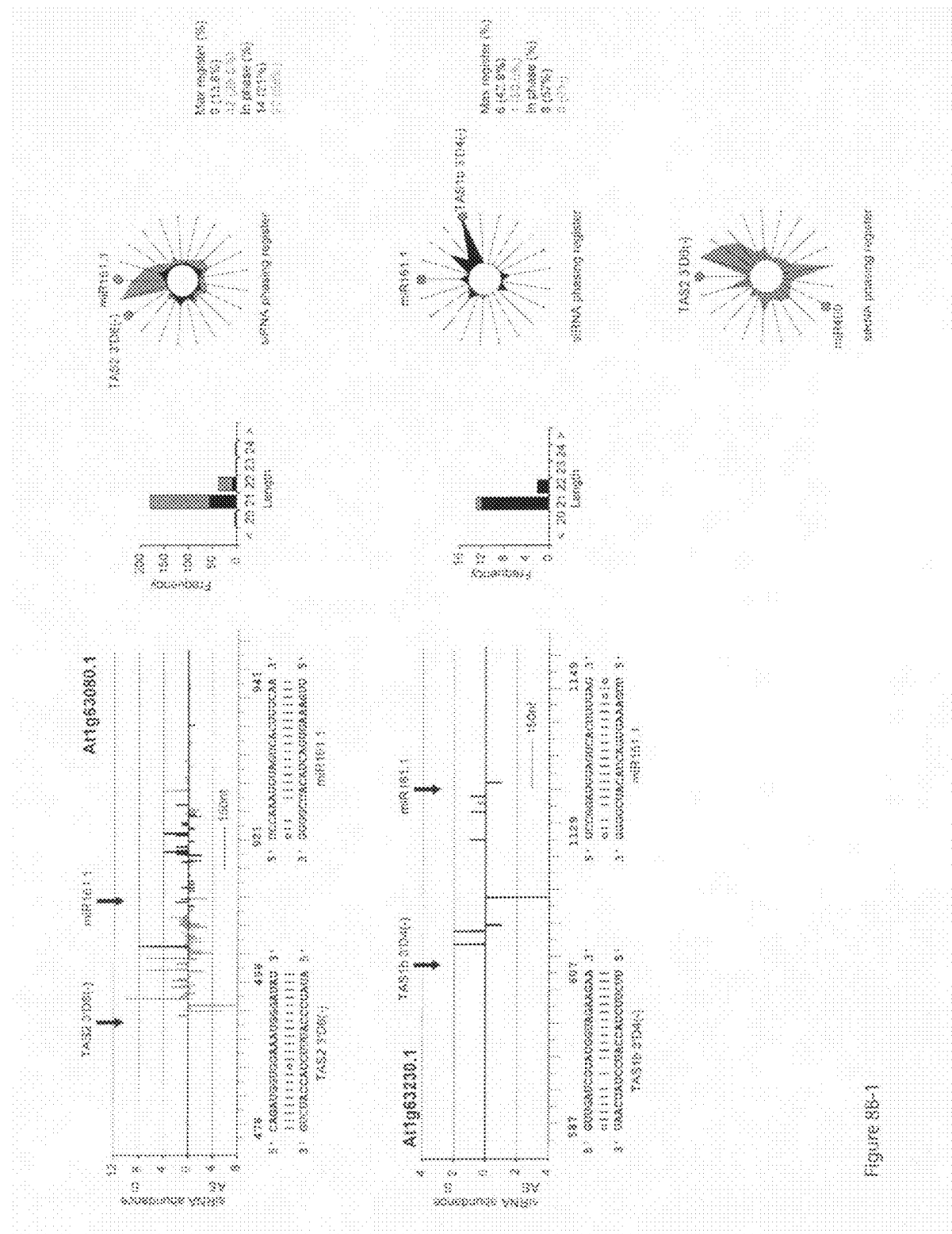
Figures 2, 8B:
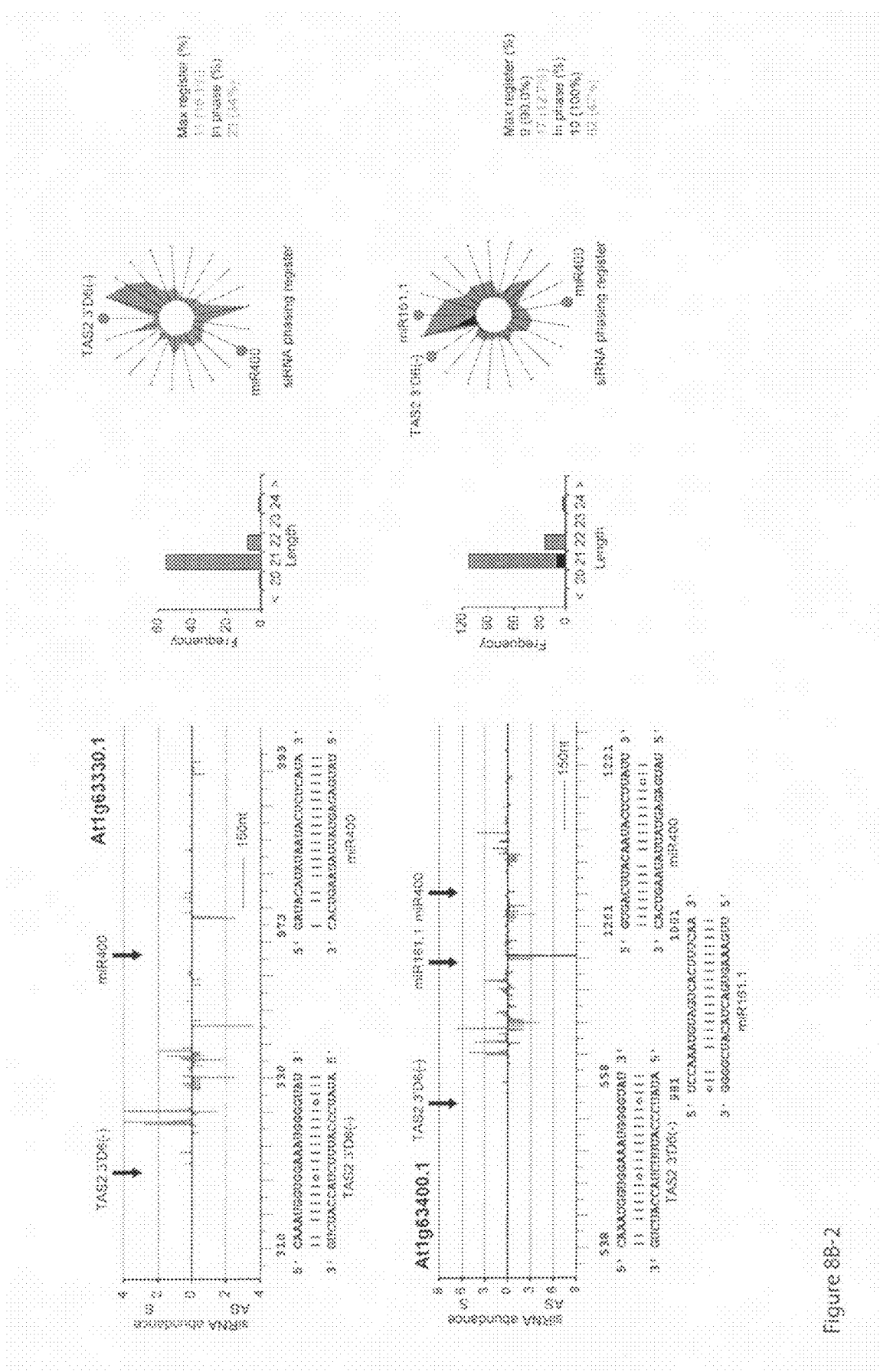
Figures 3, 8B:
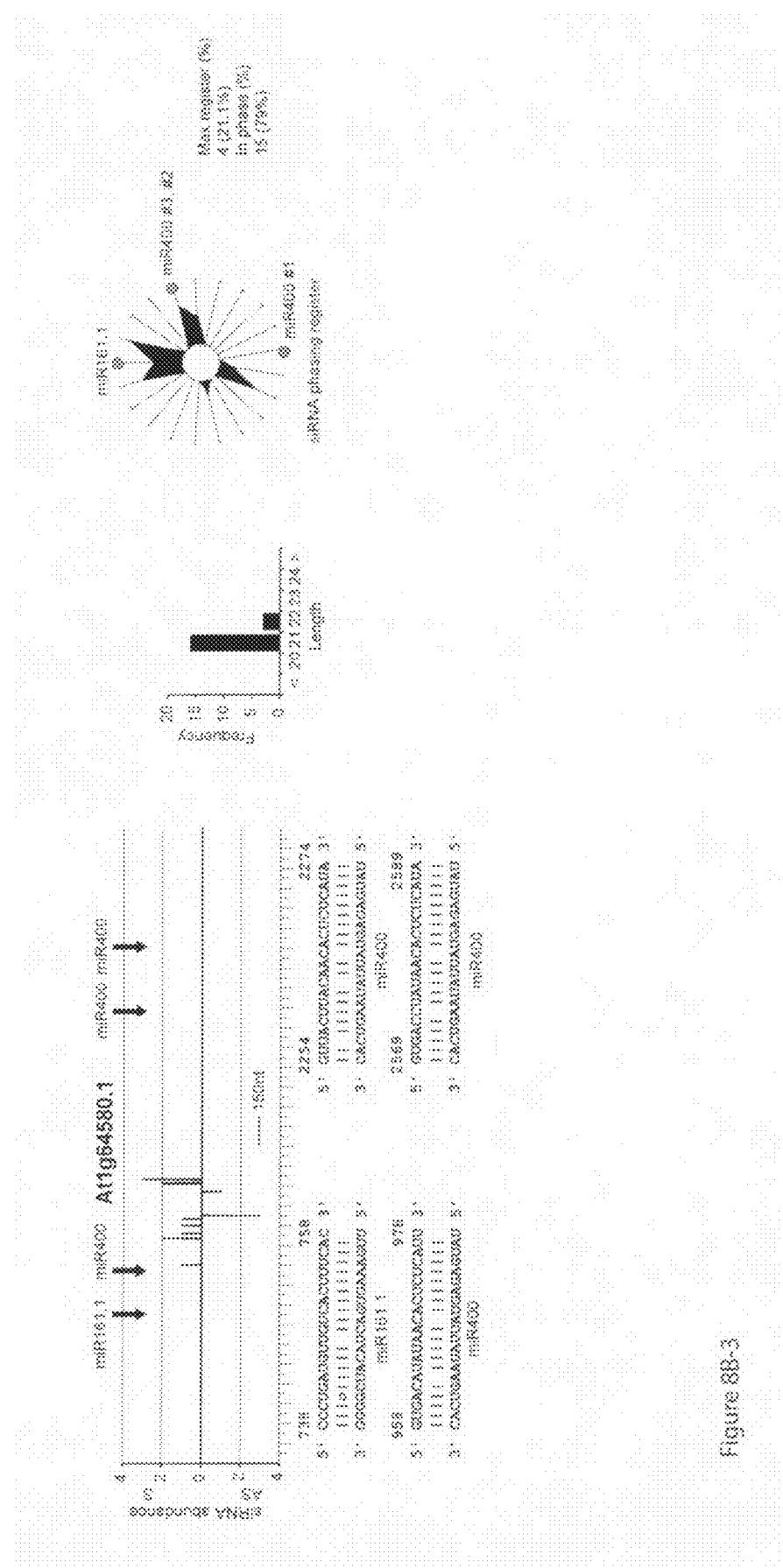

All known *Arabidopsis* tasiRNA loci have miRNA complementary sites thought to be important for setting the register of phased siRNA production (Allen et al., 2005; Yoshikawa et al., 2005). All four moss TAS loci had complementary sites for miR390 positioned so as to set the phasing register of the dominant siRNA species (FIG. 1). miR390 is conserved throughout land plants (Axtell and Bartel, 2005) and is the same miRNA that sets the phasing register for the *Arabidopsis* TAS3 siRNAs (Allen et al., 2005). PpTAS2 has one siRNA in common with PpTAS1 and another in common with PpTAS3, but otherwise the four *P. patens* TAS loci shared little sequence identity beyond their miR390 complementary sites (FIG. 7). Moreover, no sequences resembling the *Arabidopsis* tasiRNAs were discerned in any of the four PpTAS loci, begging the question as to the evolutionary relationship between the TAS loci of moss and those of higher plants. Nonetheless, the presence of miR390 complementary sites in the PpTAS loci supported the idea that these four loci were indeed tasiRNA genes and suggested that miR390 has been setting the phasing register of tasiRNAs since the last common ancestor of moss and angiosperms.

Surprisingly, each of the PpTAS loci contained not one but two miR390 complementary sites, one upstream and another downstream of the siRNA-corresponding region (FIG. 1). The phasing register of the siRNAs was consistent with cleavage at both complementary sites: 71.3% of the PpTAS-derived small RNAs began within one nucleotide of the residues predicted by cleavage at either the 5' or 3' site. miR390-mediated cleavage was confirmed at both sites of PpTAS1 using 5'-RACE (Llave et al., 2002); 11 out of 17 sequenced cleavage products had 5' residues corresponding precisely to those predicted by cleavage at either the 5' or 3' miR390 complementary site (FIG. 1A). These observations indicated that tasiRNA biogenesis from PpTAS loci is triggered by two miR390-directed cleavage events that together define the intervening cleavage product as a substrate for subsequent RdRp and Dicer activity.

Dual miR390 Complementary Sites are a Conserved Feature of tasiRNA Precursors

Having found two miR390 complementary sites in each of the four moss TAS loci, we examined the *Arabidopsis* TAS3 locus to see if it might also have two sites. A second miR390 site was found, located upstream of the tasiRNA region (FIG. 2A). Pyrosequencing of small RNAs from wild-type *Arabidopsis* inflorescences, leaves, seedlings and siliques yielded 887,266 reads that matched the *Arabidopsis* genome (Rajagopalan, Vaucheret, and Bartel, submitted) of which 1,806 were AtTAS3-derived tasiRNAs. Many were in phase with the 3' cleavage site, but a sizable proportion, particularly from the center and 5' region of the locus, were not (FIG. 2A). These alternatively phased siRNAs were largely in a register predicted by miR390-directed cleavage at the newly identified 5' site. However, these alternatively phased siRNAs were almost equally consistent with the register that would be set by the most abundant TAS3 siRNA, TAS3 5'D2(-) (FIG. 2A). Because the newly identified 5' miR390 complementary site in AtTAS3 was unable to direct miR390-directed cleavage (see below), we favor the hypothesis put forward by Allen et al. (2005) that the alternatively phased AtTAS3 tasiRNAs are phased by TAS3 5'D2(−)-mediated cleavage.

EST sequences representing AtTAS3 homologs from diverse seed plants have two reported regions of nucleotide conservation: a ~42-nt region corresponding to the AtTAS3 tasiRNAs that target ARF3 and ARF4 (tasiARFs) and a ~21-nt region corresponding to the 3' miR390 complementary site (Allen et al., 2005). We found a third conserved region of seed-plant AtTAS3 homologs, which corresponded to the 5' miR390 complementary site (FIG. 2B), suggesting that dual targeting of tasiRNA precursors is an evolutionarily conserved function of miR390. For most of the AtTAS3 homologs, cleavage at the 3' miR390 complementary site would set the phasing register required for the accurate production of the two conserved tasiARFs, which explains why the length of the region between tasiARFs and the 3' miR390 complementary site is relatively constant (FIG. 2B; Allen et al., 2005). In contrast, the lengths of the regions between the newly identified 5' miR390 complementary sites and the tasiARFs were variable and generally out of phase with the tasiARFs (FIG. 2B). The exception was the sole gymnosperm AtTAS3 homolog; for the loblolly pine (*Pinus taeda*) TAS3 homolog, the 5' miR390 complementary site was the one that was in the proper register to direct accurate production of the tasiARFs, whereas the 3' site was nine nucleotides out of phase.

Cleavage-Independent Function of a Conserved Plant miRNA Complementary Site

The 5' miR390 complementary site of AtTAS3 was unusual for a plant miRNA target in containing a mismatch and two G:U wobbles involving nucleotides 9-11 of miR390 (FIG. 2A). Such mismatches in nucleotides surrounding the potential scissile phosphate inhibit miRNA-directed endonucleolytic cleavage in vitro and in vivo (Mallory et al., 2004; Schwab et al., 2005). Mismatches involving positions 9-11 of miR390 were a conserved feature of the 5' sites of TAS3 homologs and were in stark contrast to the pairing preferences for the 3' sites of the same homologs (FIG. 2C) and those observed for plant miRNA complementary sites in general (Mallory et al., 2004). 5' RACE failed to detect cDNA ends terminating within the upstream site (data not shown), which suggested that the conserved, non-canonical 5' miR390 complementary sites of flowering-plant TAS3 genes might function independently of target cleavage.

We next tested, using wheat-germ extract (Tang et al., 2003), the biochemical properties of the miR390 complementary sites. A substrate containing the 5' miR390 complementary site of a moss TAS gene (PpTAS3) was cleaved in vitro (FIG. 3A). Similarly, the 5' complementary site from the gymnosperm homolog (PtTAS3) was efficiently cleaved despite the presence of a mismatch at position 10 (FIG. 3A). Cleavage at the PtTAS3 5' site demonstrated that some cleavage targets could be missed when using target-prediction guidelines, such as those of Schwab et al. (2005), that forbid mismatches at position 10. In contrast, cleavage of the 5' site of *Arabidopsis* TAS3 (AtTAS3), which lacked Watson-Crick pairing at positions 9, 10 and 11, was not detected under conditions in which cleavage of the 3' site was observed (FIG. 3A-B). Mutations disrupting the 3' site abolished cleavage, whereas adding additional miR390 to increase the amount of miR390-programmed silencing specifically enhanced cleavage (FIG. 3B). Repairing the mismatches to nucleotides 9-11 of miR390 resulted in efficient cleavage at the 5' site, indicating that cleavage of the wild-type 5' site would have been detected had it occurred (FIG. 3B).

Cleavage of the PtTAS3 5' site provided an explanation for why the pine tasiARFs were in phase with the 5' miR390 complementary site rather than the 3' site (FIG. 2B); because the PtTAS3 site can be cleaved, it could be the site that sets the phasing register for tasiARF production in pine. As a corollary, the mismatches found in the 5' site of AtTAS3 and conserved among flowering plants appear to prevent cleavage that would set an inappropriate register for tasiARF production from the TAS3 genes of most flowering plants.

If the newly identified 5' miR390 complementary site of AtTAS3 evolved to interact with miR390 without being cleaved, we reasoned that it would efficiently bind the miR390-programmed silencing complex. To test this idea, we measured the ability of different sites to bind and sequester endogenous silencing complex. Adding unlabeled RNA with the AtTAS3 3' site (identical to the labeled substrate) competed for cleavage of labeled substrate with classical Michaelis-Menten behavior ($K_m$=8.4 nM; $k_{cat}$=0.006/s, estimating the concentration of endogenous miR390 silencing complex at 32 pM by quantitative Northern). Adding AtTAS3 5' site reduced the rate of cleavage even more efficiently, with the $K_i$ of the 5' site ~5-fold below the $K_m$ of the 3' site (FIG. 3C). Disrupting complementarity to miR390 abolished the ability of both the 3' and 5' substrates to act as competitive inhibitors of miR390-mediated cleavage, thereby demonstrating the specificity of inhibition (FIG. 3C). These observations coupled with the conservation of central mismatches indicated that the newly identified 5' sites of flowering plants have evolved to bind the miR390 silencing complex while simultaneously avoiding cleavage. Indeed, analysis of flowering plant AtTAS3 homologs showed that mismatches outside positions 8-11 were rare and almost never more disruptive than a G:U wobble (FIG. 2C).

Both miR390 Complementary Sites are Required for Full AtTAS3 Function

We transformed tas3-1−/− plants with an AtTAS3 genomic construct that can complement the tas3-1 developmental defects (Adenot et al., 2006) and compared the frequency of complementation to that observed with variant constructs that had changes in one or both of the miRNA complementary sites (FIG. 4). Of the T1 plants transformed with the wild-type AtTAS3 construct (++), 37% were complemented for AtTAS3 function, as indicated by lack of the elongated and curled leaves characteristic of the tas3-1 line. Disrupting the 3' complementary site (+Δ) lowered the frequency of complementation to 19.4%, demonstrating the importance of the 3' site. Mutations of the 5' complementary site that either disrupted binding (Δ+) or enhanced cleavage (R+) in vitro both lowered the frequency of complementation to levels comparable to that of the 3'-site disruption. These results demonstrated the importance of binding without cleavage at this site that was out of phase with the functional siRNAs. Simultaneous disruption of both sites (ΔΔ) lowered the apparent complementation frequency to 13.1%, a value indistinguishable from the background level of the assay. The lower complementation frequency of the ΔΔ construct compared to all constructs with single sites suggested some complementation by the single-site constructs, even the RΔ construct. We suspect that the relatively infrequent cases in which the single-site constructs complemented the tas3-1 phenotype were due to miRNA-enhanced siRNA generation from the integrated transgene locus; transgenes often trigger siRNA production, especially when they include an miRNA complementary site (Parizotto et al., 2004), and the inventory of small RNAs produced from TAS3 transgenes might occasionally include sufficient levels of tasiARFs to enable wild-type development. Overall, the differential efficacies of the wild-type and single-site constructs demonstrated the importance of both miR390 complementary sites for AtTAS3 function, and when considered together with our other results for the AtTAS3 5' site, they indicated that a miRNA-binding site that is not cleaved can nonetheless play an important, evolutionarily conserved role in plants.

A Conserved Trigger for siRNA Biogenesis

To test the hypothesis that dual small RNA complementary sites predispose the bounded region toward phased siRNA production, we examined *Arabidopsis* genes with multiple complementary sites for evidence of siRNA production. ARF3 and ARF4 both possess two sites complementary to the tasiARFs TAS3 5'D7(+) and TAS3 5'D8(+) (Allen et al., 2005; Williams et al., 2005). For both ARF3 and ARF4, our set of 887,266 *Arabidopsis* small RNA reads contained siRNAs from the region bounded by the tasiARF complementary sites. These included 33 siRNA reads from the bounded region of ARF4, and one read from the bounded region of ARF3. All 33 of the ARF4 reads were in phase with each other (FIG. 5A), and the single ARF3 read was in perfect phase with the cleavage sites (data not shown). For ARF3, no additional reads were observed outside of the bounded region, but for ARF4, an additional population of sense and antisense small RNAs arose from the region downstream of the 3' complementary site. However, in contrast to the 21-nt, phased siRNAs from the region spanning the two sites, the siRNAs from the downstream cluster were not in phase with each other and were a mixture of 21mers and 24mers (FIG. 5A). On the whole, the endogenous siRNAs from ARF3 and ARF4 supported the hypothesis that dual small RNA-mediated cleavage events predispose the intervening fragment for recognition by an RdRp, leading to the production of phased siRNAs.

Several repetitive pentatricopeptide repeat (PPR) genes have been predicted or validated as targets of miR161, miR400, and AtTAS1b- and AtTAS2-derived tasiRNAs (Rhoades et al., 2002; Allen et al., 2004; Sunkar and Zhu, 2004; Vazquez et al., 2004a; Allen et al., 2005). We found 15 PPR genes that had at least two sites complementary to miR161.1, miR400, TAS1b 3'D4(−), or TAS2 3'D6(−). All 15 of these genes, including At1g62670, which was recently reported to give rise to secondary siRNAs (Ronemus et al., 2006), produced siRNAs from between small RNA complementary sites (FIGS. 5B, 8A-8C). The PPR-associated siRNA populations were predominantly 21 nt in length, with a small proportion being 22 nt. Because of the highly repetitive nature of these target genes, many of the siRNAs could not be assigned to a single locus; however, even with this complication, the majority of the PPR-derived siRNAs were in a 21-nt phase at registers consistent with cleavage at the known or predicted target sites, with 58% beginning within one nucleotide of that predicted by cleavage at one of the sites (FIGS. 5B, 8A-8C). This represented a substantial enrichment of phased siRNAs when compared to a random distribution of small RNAs falling into each of the possible 21 registers.

Analyses of secondary siRNAs deriving from miRNA targets with a single complementary site underscored the importance of dual complementary sites. Very little evidence for the production of siRNAs from single-site miRNA targets has been reported, with only the targets of miR168, miR393, and miR408 generating small RNAs that have been detected by sequencing of *Arabidopsis* small RNAs (Lu et al., 2005; Ronemus et al., 2006). The very low abundance of secondary siRNAs corresponding to *Arabidopsis* miRNA targets was also observed when analyzing our large set of sequenced *Arabidopsis* small RNAs: As previously reported, significant numbers of secondary siRNAs were derived from AGO1, the only known target of miR168, as well as from the targets of miR393 (FIG. 9). Sense and antisense small RNAs, predominantly 21 nt in length, arose only from the region downstream of the miRNA complementary sites, and they tended to be in phase with the end defined by miRNA-mediated cleavage (FIG. 9). The phasing register, sizes, and downstream location of these secondary siRNAs were reminiscent of AtTAS1a-c and AtTAS2 tasiRNAs, suggesting that they may have arisen through a common mechanism. Nonetheless, these examples were exceptions to the general observation that plant miRNA targets with single miRNA complementary sites were not efficient substrates for RdRp activity and subsequent production of secondary siRNAs. Even deeper sequencing of *Arabidopsis* small RNA populations may reveal that siRNA formation from single-site miRNA targets is a more widespread, albeit very low-efficiency phenomenon. Taken together, our results strongly supported a model in which dual miRNA complementary sites consistently predispose the bounded region of the target toward entry into a tasiRNA-like pathway, whereas a single miRNA complementary site triggers siRNA production much less reliably and efficiently.

References

Following is a listing of certain references cited throughout the application. Other references are cited elsewhere herein. The teachings of all cited references are incorporated herein by reference for all purposes.

Adenot, X., Elmayan, T., Lauressergues, D., Boutet, S., Bouche, N., Gasciolli, V., and Vaucheret, H. (2006). DRB4-dependent TAS3 trans-acting siRNAs control leaf morphology through AGO7. Curr. Biol. 16, 927-932.

Allen, E., Xie, Z., Gustafson, A. M., and Carrington, J. C. (2005). microRNA-directed phasing during trans-acting siRNA biogenesis in plants. Cell 121, 207-221.

Allen, E., Xie, Z., Gustafson, A. M., Sung, G. H., Spatafora, J. W., and Carrington, J. C. (2004). Evolution of microRNA genes by inverted duplication of target gene sequences in *Arabidopsis thaliana*. Nat. Genet. 36, 1282-1290.

Arazi, T., Talmor-Neiman, M., Stav, R., Riese, M., Huijser, P., and Baulcombe, D. C. (2005). Cloning and characterization of micro-RNAs from moss. Plant J. 43, 837-848.

Axtell, M. J., and Bartel, D. P. (2005). Antiquity of microRNAs and their targets in land plants. Plant Cell 17, 1658-1673.

Bartel, D. P. (2004). MicroRNAs: genomics, biogenesis, mechanism, and function. Cell 116, 281-297.

Bouche, N., Lauressergues, D., Gasciolli, V., and Vaucheret, H. (2006). An antagonistic function for *Arabidopsis* DCL2 in development and a new function for DCL4 in generating viral siRNAs. EMBO J. 25, 3347-3356.

Deleris, A., Gallego-Bartolome, J., Bao, J., Kasschau, K. D., Carrington, J. C., and Voinnet, O. (2006). Hierarchical action and inhibition of plant Dicer-Like proteins in antiviral defense. Science 313, 68-71.

Elmayan, T., and Vaucheret, H. (1996). Expression of single copies of a strongly expressed 35S transgene can be silenced post-transcriptionally. Plant J. 9, 787-797.

Fahlgren, N., Montgomery, T. A., Howell, M. D., Allen, E., Dvorak, S. K., Alexander, A. L., and Carrington, J. C. (2006). Regulation of AUXIN RESPONSE FACTOR3 by TAS3 ta-siRNA affects developmental timing and patterning in *Arabidopsis*. Curr. Biol. 16, 939-944.

Garcia, D., Collier, S. A., Byrne, M. E., and Martienssen, R. A. (2006). Specification of leaf polarity in *Arabidopsis* via the trans-acting siRNA Pathway. Curr. Biol. 16, 933-938.

Gasciolli, V., Mallory, A. C., Bartel, D. P., and Vaucheret, H. (2005). Partially redundant functions of *Arabidopsis*

DICER-like enzymes and a role for DCL4 in producing trans-acting siRNAs. Curr. Biol. 15, 1494-1500.

Hunter, C., Willmann, M. R., Wu, G., Yoshikawa, M., de la Luz Gutierrez-Nava, M., and Poethig, R. S. (2006). Trans-acting siRNA-mediated repression of ETTIN and ARF4 regulates heteroblasty in *Arabidopsis*. Development 133, 2973-2981.

Lau, N. C., Lim, L. P., Weinstein, E. G., and Bartel, D. P. (2001). An abundant class of tiny RNAs with probable regulatory roles in *Caenorhabditis elegans*. Science 294, 858-862.

Lindbo, J. A., Silva-Rosales, L., Proebsting, W. M., and Dougherty, W. G. (1993). Induction of a highly specific antiviral state in transgenic plants: Implications for regulation of gene expression and virus resistance. Plant Cell 5, 1749-1759.

Llave, C., Xie, Z., Kasschau, K. D., and Carrington, J. C. (2002). Cleavage of Scarecrow-like mRNA targets directed by a class of *Arabidopsis* miRNA. Science 297, 2053-2056.

Lu, C., Tej, S. S., Luo, S., Haudenschild, C. D., Meyers, B. C., and Green, P. J. (2005). Elucidation of the small RNA component of the transcriptome. Science 309, 1567-1569.

Mallory, A. C., Reinhart, B. J., Jones-Rhoades, M. W., Tang, G., Zamore, P. D., Barton, M. K., and Bartel, D. P. (2004). MicroRNA control of PHABULOSA in leaf development: importance of pairing to the microRNA 5' region. EMBO J. 23, 3356-3364.

Margulies, M., Egholm, M., Altman, W. E., Attiya, S., Bader, J. S., Bemben, L. A., Berka, J., Braverman, M. S., Chen, Y. J., Chen, Z., et al. (2005). Genome sequencing in microfabricated high-density picolitre reactors. Nature 437, 376-380.

Parizotto, E. A., Dunoyer, P., Rahm, N., Himber, C., and Voinnet, O. (2004). In vivo investigation of the transcription, processing, endonucleolytic activity, and functional relevance of the spatial distribution of a plant miRNA. Genes Dev. 18, 2237-2242.

Peragine, A., Yoshikawa, M., Wu, G., Albrecht, H. L., and Poethig, R. S. (2004). SGS3 and SGS2/SDE1/RDR6 are required for juvenile development and the production of trans-acting siRNAs in *Arabidopsis*. Genes Dev. 18, 2368-2379.

Rhoades, M. W., Reinhart, B. J., Lim, L. P., Burge, C. B., Bartel, B., and Bartel, D. P. (2002). Prediction of plant microRNA targets. Cell 110, 513-520.

Ronemus, M., Vaughn, M. W., and Martienssen, R. (2006). MicroRNA-targeted and small interfering RNA-mediated mRNA degradation is regulated by Argonaute, Dicer, and RNA-dependent RNA polymerase in *Arabidopsis*. Plant Cell 18, 1559-1574.

Schwab, R., Palatnik, J. F., Riester, M., Schommer, C., Schmid, M., and Weigel, D. (2005). Specific effects of microRNAs on the plant transcriptome. Dev. Cell 8, 517-527.

Smith, H. A., Swaney, S. L., Parks, T. D., Wernsman, E. A., and Dougherty, W. G. (1994). Transgenic plant virus resistance mediated by untranslatable sense RNAs: Expression, regulation, and fate of nonessential RNAs. Plant Cell 6, 1441-1453.

Sunkar, R., and Zhu, J. K. (2004). Novel and stress-regulated microRNAs and other small RNAs from *Arabidopsis*. Plant Cell 16, 2001-2019.

Tang, G., Reinhart, B. J., Bartel, D. P., and Zamore, P. D. (2003). A biochemical framework for RNA silencing in plants. Genes Dev. 17, 49-63.

Vazquez, F., Gasciolli, V., Crete, P., and Vaucheret, H. (2004a). The nuclear dsRNA binding protein HYL1 is required for microRNA accumulation and plant development, but not posttranscriptional transgene silencing. Curr. Biol. 14, 346-351.

Vazquez, F., Vaucheret, H., Rajagopalan, R., Lepers, C., Gasciolli, V., Mallory, A. C., Hilbert, J. L., Bartel, D. P., and Crete, P. (2004b). Endogenous trans-acting siRNAs regulate the accumulation of *Arabidopsis* mRNAs. Mol. Cell. 16, 69-79.

Williams, L., Carles, C. C., Osmont, K. S., and Fletcher, J. C. (2005). A database analysis method identifies an endogenous trans-acting short-interfering RNA that targets the *Arabidopsis* ARF2, ARF3, and ARF4 genes. Proc. Natl. Acad. Sci. U.S.A. 102, 9703-9708.

Xie, Z., Allen, E., Wilken, A., and Carrington, J. C. (2005). DICER-LIKE 4 functions in trans-acting small interfering RNA biogenesis and vegetative phase change in *Arabidopsis thaliana*. Proc. Natl. Acad. Sci. U.S.A. 102, 12984-12989.

Xie, Z., Johansen, L. K., Gustafson, A. M., Kasschau, K. D., Lellis, A. D., Zilberman, D., Jacobsen, S. E., and Carrington, J. C. (2004). Genetic and functional diversification of small RNA pathways in plants. PLoS Biol. 2, E104.

Yoshikawa, M., Peragine, A., Park, M. Y., and Poethig, R. S. (2005). A pathway for the biogenesis of trans-acting siRNAs in *Arabidopsis*. Genes Dev. 19, 2164-2175.

Zamore, P. D., and Haley, B. (2005). Ribo-gnome: the big world of small RNAs. Science 309, 1519-1524.

What is claimed is:

1. A method of inhibiting expression of a target gene in a plant comprising the steps of:
    expressing a single-stranded RNA in the plant, wherein the single-stranded RNA comprises a nucleic acid sequence that corresponds to a target gene and is flanked by miR390 complementary sites and wherein the single-stranded RNA or a template for transcription thereof was introduced into the plant or an ancestor of the plant, selected from a plant or plant cell from which the plant was generated, by the hand of man; and
    maintaining the plant under conditions in which (i) the single-stranded RNA is cleaved within at least one of said miR390 complementary sites flanking the nucleic acid sequence; (ii) the resulting RNA is transcribed to double-stranded RNA (dsRNA); and (iii) the double-stranded RNA is cleaved to form siRNA that inhibit expression of the target gene, thereby inhibiting expression of the target gene in the plant.

2. The method of claim 1, wherein the target gene is endogenous to a plant.

3. The method of claim 1, wherein the single-standard RNA is cleaved within both of said miR390 complementary sites.

* * * * *

SEQUENCE LISTING

<160> NUMBER OF SEQ ID NOS: 336

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aagcucagga gggauagcgc c                                              21

<210> SEQ ID NO 2
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 2
uugaaaguga cuacaucggg g                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uaugagagua uuauaaguca c                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
auaucccauu ucuaccaucu g                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uucuucuacc auccuaucaa u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uucuugaccu uguaagaccc c                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uucuugaccu uguaaggccu u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
                          oligonucleotide

<400> SEQUENCE: 8
ucgcuuggug caggucggga a                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uccaaaggga ucgcauugau c                                              21

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uucgcuugca gagagaaauc ac                                             22

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtatgtgact ccattacatc aactgca                                        27

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tatcaccgcc gcctgtggcc ggctaaga                                       28

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaggtagaga tagatatcta ttctatatt                                      29

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 14
agaaagagat ggggtcttac aaggtcaa                                    28

<210> SEQ ID NO 15
<211> LENGTH: 49
<212> TYPE: DNA
<213> ORGANISM: Arabidopsis thaliana

<400> SEQUENCE: 15
caatgataaa gcggtgttat catactagtg attttagtcg gattttttc              49

<210> SEQ ID NO 16
<211> LENGTH: 49
<212> TYPE: DNA
<213> ORGANISM: Arabidopsis thaliana

<400> SEQUENCE: 16
gaaaaaatcc gactaaaatc actagtatga taacaccgct ttatcattg              49

<210> SEQ ID NO 17
<211> LENGTH: 49
<212> TYPE: DNA
<213> ORGANISM: Arabidopsis thaliana

<400> SEQUENCE: 17
caatgataaa gcggtgttat ccctcctgag cttttagtcg gattttttc              49

<210> SEQ ID NO 18
<211> LENGTH: 49
<212> TYPE: DNA
<213> ORGANISM: Arabidopsis thaliana

<400> SEQUENCE: 18
gaaaaaatcc gactaaaagc tcaggaggga taacaccgct ttatcattg              49

<210> SEQ ID NO 19
<211> LENGTH: 49
<212> TYPE: DNA
<213> ORGANISM: Physcomitrella patens

<400> SEQUENCE: 19
caatgataaa gcgacgctac ccttcctgag ctattagtcg gattttttc              49

<210> SEQ ID NO 20
<211> LENGTH: 49
<212> TYPE: DNA
<213> ORGANISM: Physcomitrella patens

<400> SEQUENCE: 20
gaaaaaatcc gactaatagc tcaggaaggg tagcgtcgct ttatcattg              49

<210> SEQ ID NO 21
<211> LENGTH: 49
<212> TYPE: DNA
<213> ORGANISM: Pinus taeda

<400> SEQUENCE: 21
caatgataaa gcgacgctat cccctctgag cttttagtcg gattttttc              49

<210> SEQ ID NO 22
<211> LENGTH: 49
<212> TYPE: DNA
<213> ORGANISM: Pinus taeda

<400> SEQUENCE: 22
gaaaaaatcc gactaaaagc tcagagggga tagcgtcgct ttatcattg        49

<210> SEQ ID NO 23
<211> LENGTH: 44
<212> TYPE: DNA
<213> ORGANISM: Arabidopsis thaliana

<400> SEQUENCE: 23
ctcctacctt gtctatccca ctagtgctaa tctccacata tatc              44

<210> SEQ ID NO 24
<211> LENGTH: 44
<212> TYPE: DNA
<213> ORGANISM: Arabidopsis thaliana

<400> SEQUENCE: 24
gatatatgtg gagattagca ctagtgggat agacaaggta ggag              44

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctaatacga ctcactatag ggcattaagg aaaacataac c                  41

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cagtgtgatg gatatctgca g                                       21

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctaatacga ctcactatag ggcattaagg aaaacataac c                  41

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gagaataatg aaatgcatc                                          19

<210> SEQ ID NO 29
<211> LENGTH: 39
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 29
gctaatacga ctcactatag ggatccgctg tgctgagac                            39

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gagaataatg aaatgcatc                                                 19

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gctaatacga ctcactatag ggaatagata tctatctcta cctc                     44

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cagtgtgatg gatatctgca g                                              21

<210> SEQ ID NO 33
<211> LENGTH: 42
<212> TYPE: DNA
<213> ORGANISM: Arabidopsis thaliana

<400> SEQUENCE: 33
ttcttgacct tgtaaggcct tttcttgacc ttgtaagacc cc                       42

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atcgtaggca cctgaga                                                   17

<210> SEQ ID NO 35
<211> LENGTH: 21
<212> TYPE: RNA
<213> ORGANISM: Citrus x paradisi

<400> SEQUENCE: 35
ggugcuaucc uaccugagcu u                                              21
```

-continued

```
<210> SEQ ID NO 36
<211> LENGTH: 21
<212> TYPE: RNA
<213> ORGANISM: Manihot esculenta

<400> SEQUENCE: 36
ggugcuaucc uaccugagcu u                                              21

<210> SEQ ID NO 37
<211> LENGTH: 21
<212> TYPE: RNA
<213> ORGANISM: Populus tremula x Populus tremuloides

<400> SEQUENCE: 37
ggugcuaucc uaccugagcu u                                              21

<210> SEQ ID NO 38
<211> LENGTH: 21
<212> TYPE: RNA
<213> ORGANISM: Pinus taeda

<400> SEQUENCE: 38
gacgcuaucc ccucugagcu u                                              21

<210> SEQ ID NO 39
<211> LENGTH: 21
<212> TYPE: RNA
<213> ORGANISM: Populus trichocarpa

<400> SEQUENCE: 39
ggugcuaucc uaccugagcu u                                              21

<210> SEQ ID NO 40
<211> LENGTH: 21
<212> TYPE: RNA
<213> ORGANISM: Pinus taeda

<400> SEQUENCE: 40
gacgcuaucc ccucugagcu u                                              21

<210> SEQ ID NO 41
<211> LENGTH: 21
<212> TYPE: RNA
<213> ORGANISM: Zea mays

<400> SEQUENCE: 41
gguguuaucc ugauugagcu u                                              21

<210> SEQ ID NO 42
<211> LENGTH: 21
<212> TYPE: RNA
<213> ORGANISM: Gossypium raimondii

<400> SEQUENCE: 42
ggugcuaucc caccugagcu u                                              21

<210> SEQ ID NO 43
<211> LENGTH: 21
<212> TYPE: RNA
<213> ORGANISM: Vitis vinifera

<400> SEQUENCE: 43
ggugcuaucc uaccugagcu u                                              21
```

-continued

```
<210> SEQ ID NO 44
<211> LENGTH: 21
<212> TYPE: RNA
<213> ORGANISM: Euphorbia esula

<400> SEQUENCE: 44
ggugcuaucc uaucugagcu u                                              21

<210> SEQ ID NO 45
<211> LENGTH: 21
<212> TYPE: RNA
<213> ORGANISM: Lycopersicon esculentum

<400> SEQUENCE: 45
ggugcuaucc uaccugagcu u                                              21

<210> SEQ ID NO 46
<211> LENGTH: 21
<212> TYPE: RNA
<213> ORGANISM: Zea mays

<400> SEQUENCE: 46
gguguuaucc cgacugaacu u                                              21

<210> SEQ ID NO 47
<211> LENGTH: 21
<212> TYPE: RNA
<213> ORGANISM: Vitis vinifera

<400> SEQUENCE: 47
ggugcuaucc uaccugagcu u                                              21

<210> SEQ ID NO 48
<211> LENGTH: 21
<212> TYPE: RNA
<213> ORGANISM: Gossypium raimondii

<400> SEQUENCE: 48
ggugcuaucc caccugagcu u                                              21

<210> SEQ ID NO 49
<211> LENGTH: 21
<212> TYPE: RNA
<213> ORGANISM: Theobroma cacao

<400> SEQUENCE: 49
ggugcuaucc uaccugagcu u                                              21

<210> SEQ ID NO 50
<211> LENGTH: 21
<212> TYPE: RNA
<213> ORGANISM: Populus euphratica

<400> SEQUENCE: 50
ggugcuaucc uaccugagcu u                                              21

<210> SEQ ID NO 51
<211> LENGTH: 21
<212> TYPE: RNA
<213> ORGANISM: Hordeum vulgare

<400> SEQUENCE: 51
gguguuaucc cgaaugagcu u                                              21
```

```
<210> SEQ ID NO 52
<211> LENGTH: 21
<212> TYPE: RNA
<213> ORGANISM: Manihot esculenta

<400> SEQUENCE: 52
ggugcuaucc uaccugagcu u                                          21

<210> SEQ ID NO 53
<211> LENGTH: 21
<212> TYPE: RNA
<213> ORGANISM: Malus x domestica

<400> SEQUENCE: 53
ggugcuaucc uaccugagcu u                                          21

<210> SEQ ID NO 54
<211> LENGTH: 21
<212> TYPE: RNA
<213> ORGANISM: Glycine max

<400> SEQUENCE: 54
ggugcuaucc uaucugagcu u                                          21

<210> SEQ ID NO 55
<211> LENGTH: 21
<212> TYPE: RNA
<213> ORGANISM: Sorghum bicolor

<400> SEQUENCE: 55
ggcguuaucc ugauugagcu u                                          21

<210> SEQ ID NO 56
<211> LENGTH: 21
<212> TYPE: RNA
<213> ORGANISM: Populus trichocarpa

<400> SEQUENCE: 56
ggugcuaucc uaccugagcu u                                          21

<210> SEQ ID NO 57
<211> LENGTH: 21
<212> TYPE: RNA
<213> ORGANISM: Vitis vinifera

<400> SEQUENCE: 57
ggugcuaucc uaccugagcu u                                          21

<210> SEQ ID NO 58
<211> LENGTH: 21
<212> TYPE: RNA
<213> ORGANISM: Citrus x paradisi x Poncirus trifoliata

<400> SEQUENCE: 58
ggugcuaucc uaccugagcu u                                          21

<210> SEQ ID NO 59
<211> LENGTH: 21
<212> TYPE: RNA
<213> ORGANISM: Bruguiera gymnorhiza

<400> SEQUENCE: 59
ggugcuaucc uaccugagcu u                                          21
```

```
<210> SEQ ID NO 60
<211> LENGTH: 21
<212> TYPE: RNA
<213> ORGANISM: Sorghum bicolor

<400> SEQUENCE: 60
ggcguuaucc ugauugagcu u                                              21

<210> SEQ ID NO 61
<211> LENGTH: 21
<212> TYPE: RNA
<213> ORGANISM: Triticum aestivum

<400> SEQUENCE: 61
gguguuaucc ugauugagcu u                                              21

<210> SEQ ID NO 62
<211> LENGTH: 21
<212> TYPE: RNA
<213> ORGANISM: Malus x domestica

<400> SEQUENCE: 62
ggugcuaucc uagcugagcu u                                              21

<210> SEQ ID NO 63
<211> LENGTH: 21
<212> TYPE: RNA
<213> ORGANISM: Oryza sativa

<400> SEQUENCE: 63
gguguuaucc uaacugagcu u                                              21

<210> SEQ ID NO 64
<211> LENGTH: 21
<212> TYPE: RNA
<213> ORGANISM: Zea mays

<400> SEQUENCE: 64
gguguuaucc ugauugagcu u                                              21

<210> SEQ ID NO 65
<211> LENGTH: 21
<212> TYPE: RNA
<213> ORGANISM: Populus tremula

<400> SEQUENCE: 65
ggugcuaucc uaccugagcu u                                              21

<210> SEQ ID NO 66
<211> LENGTH: 21
<212> TYPE: RNA
<213> ORGANISM: Antirrhinum majus

<400> SEQUENCE: 66
ggugcuaucc uaucugagcu u                                              21

<210> SEQ ID NO 67
<211> LENGTH: 21
<212> TYPE: RNA
<213> ORGANISM: Sorghum bicolor

<400> SEQUENCE: 67
ggcguuaucc ugauugagcu u                                              21
```

```
<210> SEQ ID NO 68
<211> LENGTH: 21
<212> TYPE: RNA
<213> ORGANISM: Populus trichocarpa x Populus deltoides

<400> SEQUENCE: 68
ggugcuaucc uaccugagcu u                                              21

<210> SEQ ID NO 69
<211> LENGTH: 21
<212> TYPE: RNA
<213> ORGANISM: Mesembryanthemum crystallinum

<400> SEQUENCE: 69
ggugcuaucc uaccugagcu u                                              21

<210> SEQ ID NO 70
<211> LENGTH: 21
<212> TYPE: RNA
<213> ORGANISM: Zea mays

<400> SEQUENCE: 70
ggcguuaucc uaauugagcu u                                              21

<210> SEQ ID NO 71
<211> LENGTH: 21
<212> TYPE: RNA
<213> ORGANISM: Populus trichocarpa

<400> SEQUENCE: 71
ggugcuaucc uaccugagcu u                                              21

<210> SEQ ID NO 72
<211> LENGTH: 21
<212> TYPE: RNA
<213> ORGANISM: Populus trichocarpa

<400> SEQUENCE: 72
ggugcuaucc uaccugagcu u                                              21

<210> SEQ ID NO 73
<211> LENGTH: 21
<212> TYPE: RNA
<213> ORGANISM: Antirrhinum majus

<400> SEQUENCE: 73
ggugcuaucc uaucugagcu u                                              21

<210> SEQ ID NO 74
<211> LENGTH: 21
<212> TYPE: RNA
<213> ORGANISM: Zea mays

<400> SEQUENCE: 74
ggcguuaucc uaauugagcu u                                              21

<210> SEQ ID NO 75
<211> LENGTH: 21
<212> TYPE: RNA
<213> ORGANISM: Populus deltoides

<400> SEQUENCE: 75
ggugcuaucc uaccugagcu u                                              21
```

```
<210> SEQ ID NO 76
<211> LENGTH: 21
<212> TYPE: RNA
<213> ORGANISM: Triticum aestivum

<400> SEQUENCE: 76
gguguuaucc ugauugagcu u                                              21

<210> SEQ ID NO 77
<211> LENGTH: 21
<212> TYPE: RNA
<213> ORGANISM: Citrus clementina

<400> SEQUENCE: 77
ggugcuaucc uaccugagcu u                                              21

<210> SEQ ID NO 78
<211> LENGTH: 21
<212> TYPE: RNA
<213> ORGANISM: Glycine soja

<400> SEQUENCE: 78
ggugcuaucc uaucugagcu u                                              21

<210> SEQ ID NO 79
<211> LENGTH: 21
<212> TYPE: RNA
<213> ORGANISM: Manihot esculenta

<400> SEQUENCE: 79
ggugcuaucc uaccugagcu u                                              21

<210> SEQ ID NO 80
<211> LENGTH: 21
<212> TYPE: RNA
<213> ORGANISM: Populus trichocarpa x Populus deltoides

<400> SEQUENCE: 80
ggugcuaucc uaccugagcu u                                              21

<210> SEQ ID NO 81
<211> LENGTH: 21
<212> TYPE: RNA
<213> ORGANISM: Populus deltoides

<400> SEQUENCE: 81
ggugcuaucc uaccugagcu u                                              21

<210> SEQ ID NO 82
<211> LENGTH: 21
<212> TYPE: RNA
<213> ORGANISM: Sorghum bicolor

<400> SEQUENCE: 82
ggcguuaucc ugauugagcu u                                              21

<210> SEQ ID NO 83
<211> LENGTH: 21
<212> TYPE: RNA
<213> ORGANISM: Saccharum officinarum

<400> SEQUENCE: 83
gguguuaucc caauugagcu u                                              21
```

```
<210> SEQ ID NO 84
<211> LENGTH: 21
<212> TYPE: RNA
<213> ORGANISM: Zea mays

<400> SEQUENCE: 84
gguguuaucc ugauugagcu u                                      21

<210> SEQ ID NO 85
<211> LENGTH: 21
<212> TYPE: RNA
<213> ORGANISM: Populus trichocarpa

<400> SEQUENCE: 85
ggugcuaucc uaccugagcu u                                      21

<210> SEQ ID NO 86
<211> LENGTH: 21
<212> TYPE: RNA
<213> ORGANISM: Zea mays

<400> SEQUENCE: 86
ggcguuaucc uaauugagcu u                                      21

<210> SEQ ID NO 87
<211> LENGTH: 21
<212> TYPE: RNA
<213> ORGANISM: Zea mays

<400> SEQUENCE: 87
gguguuaucc cgacuaaacu u                                      21

<210> SEQ ID NO 88
<211> LENGTH: 21
<212> TYPE: RNA
<213> ORGANISM: Triticum aestivum

<400> SEQUENCE: 88
gguguuaucc ugauugagcu u                                      21

<210> SEQ ID NO 89
<211> LENGTH: 21
<212> TYPE: RNA
<213> ORGANISM: Populus trichocarpa

<400> SEQUENCE: 89
ggugcuaucc uaccugagcu u                                      21

<210> SEQ ID NO 90
<211> LENGTH: 21
<212> TYPE: RNA
<213> ORGANISM: Populus deltoides

<400> SEQUENCE: 90
ggugcuaucc uaccugagcu u                                      21

<210> SEQ ID NO 91
<211> LENGTH: 21
<212> TYPE: RNA
<213> ORGANISM: Saccharum officinarum

<400> SEQUENCE: 91
gguguuaucc ugaucgagcu u                                      21
```

```
<210> SEQ ID NO 92
<211> LENGTH: 21
<212> TYPE: RNA
<213> ORGANISM: Arabidopsis thaliana

<400> SEQUENCE: 92
gguguuaucc uaucugagcu u                                              21

<210> SEQ ID NO 93
<211> LENGTH: 21
<212> TYPE: RNA
<213> ORGANISM: Arabidopsis thaliana

<400> SEQUENCE: 93
uccaaaugua gucacuuuca g                                              21

<210> SEQ ID NO 94
<211> LENGTH: 21
<212> TYPE: RNA
<213> ORGANISM: Arabidopsis thaliana

<400> SEQUENCE: 94
ccccaauguu guuacuuuca a                                              21

<210> SEQ ID NO 95
<211> LENGTH: 21
<212> TYPE: RNA
<213> ORGANISM: Arabidopsis thaliana

<400> SEQUENCE: 95
cccggaugua aucacuuuca g                                              21

<210> SEQ ID NO 96
<211> LENGTH: 21
<212> TYPE: RNA
<213> ORGANISM: Arabidopsis thaliana

<400> SEQUENCE: 96
cccugauguu guuacuuuca g                                              21

<210> SEQ ID NO 97
<211> LENGTH: 21
<212> TYPE: RNA
<213> ORGANISM: Arabidopsis thaliana

<400> SEQUENCE: 97
uccaaaugua gucacuuuca g                                              21

<210> SEQ ID NO 98
<211> LENGTH: 21
<212> TYPE: RNA
<213> ORGANISM: Arabidopsis thaliana

<400> SEQUENCE: 98
uccaaaugua gucacuuuca g                                              21

<210> SEQ ID NO 99
<211> LENGTH: 21
<212> TYPE: RNA
<213> ORGANISM: Arabidopsis thaliana

<400> SEQUENCE: 99
uccaaaugua gucacuuuca a                                              21
```

<210> SEQ ID NO 100
<211> LENGTH: 21
<212> TYPE: RNA
<213> ORGANISM: Arabidopsis thaliana

<400> SEQUENCE: 100
uccggaugua gucacuuuua g                                              21

<210> SEQ ID NO 101
<211> LENGTH: 21
<212> TYPE: RNA
<213> ORGANISM: Arabidopsis thaliana

<400> SEQUENCE: 101
uccaaaugua gucacuuuca a                                              21

<210> SEQ ID NO 102
<211> LENGTH: 21
<212> TYPE: RNA
<213> ORGANISM: Arabidopsis thaliana

<400> SEQUENCE: 102
cccugauguu gucacuuuca c                                              21

<210> SEQ ID NO 103
<211> LENGTH: 21
<212> TYPE: RNA
<213> ORGANISM: Arabidopsis thaliana

<400> SEQUENCE: 103
cccugaugua uuuacuuuca a                                              21

<210> SEQ ID NO 104
<211> LENGTH: 21
<212> TYPE: RNA
<213> ORGANISM: Arabidopsis thaliana

<400> SEQUENCE: 104
accugaugua aucacuuuca a                                              21

<210> SEQ ID NO 105
<211> LENGTH: 21
<212> TYPE: RNA
<213> ORGANISM: Arabidopsis thaliana

<400> SEQUENCE: 105
cccugaugua uucacuuuca g                                              21

<210> SEQ ID NO 106
<211> LENGTH: 21
<212> TYPE: RNA
<213> ORGANISM: Arabidopsis thaliana

<400> SEQUENCE: 106
gugacuuaca auacucuuau a                                              21

<210> SEQ ID NO 107
<211> LENGTH: 21
<212> TYPE: RNA
<213> ORGANISM: Arabidopsis thaliana

<400> SEQUENCE: 107
gugacuuaua auacucucau a                                              21

-continued

<210> SEQ ID NO 108
<211> LENGTH: 21
<212> TYPE: RNA
<213> ORGANISM: Arabidopsis thaliana

<400> SEQUENCE: 108
guuacauaua auacucucau a                                              21

<210> SEQ ID NO 109
<211> LENGTH: 21
<212> TYPE: RNA
<213> ORGANISM: Arabidopsis thaliana

<400> SEQUENCE: 109
gugacuuaca auacucuuau a                                              21

<210> SEQ ID NO 110
<211> LENGTH: 21
<212> TYPE: RNA
<213> ORGANISM: Arabidopsis thaliana

<400> SEQUENCE: 110
gauacauaua auacucucau a                                              21

<210> SEQ ID NO 111
<211> LENGTH: 21
<212> TYPE: RNA
<213> ORGANISM: Arabidopsis thaliana

<400> SEQUENCE: 111
gugacuuaca auacucuuau u                                              21

<210> SEQ ID NO 112
<211> LENGTH: 21
<212> TYPE: RNA
<213> ORGANISM: Arabidopsis thaliana

<400> SEQUENCE: 112
gugacauaua acacucucau u                                              21

<210> SEQ ID NO 113
<211> LENGTH: 21
<212> TYPE: RNA
<213> ORGANISM: Arabidopsis thaliana

<400> SEQUENCE: 113
guaacuuaua guauucucau u                                              21

<210> SEQ ID NO 114
<211> LENGTH: 21
<212> TYPE: RNA
<213> ORGANISM: Arabidopsis thaliana

<400> SEQUENCE: 114
guggcuuaua cuucucucau a                                              21

<210> SEQ ID NO 115
<211> LENGTH: 21
<212> TYPE: RNA
<213> ORGANISM: Arabidopsis thaliana

<400> SEQUENCE: 115
gugacuuaua auacgcuuau a                                              21

<210> SEQ ID NO 116
<211> LENGTH: 21
<212> TYPE: RNA
<213> ORGANISM: Arabidopsis thaliana

<400> SEQUENCE: 116
uucccgagcu gcaucaagcu a                                        21

<210> SEQ ID NO 117
<211> LENGTH: 22
<212> TYPE: RNA
<213> ORGANISM: Arabidopsis thaliana

<400> SEQUENCE: 117
gagacaaugc gaucccuuug ga                                       22

<210> SEQ ID NO 118
<211> LENGTH: 22
<212> TYPE: RNA
<213> ORGANISM: Arabidopsis thaliana

<400> SEQUENCE: 118
gagaccaugc gaucccuuug ga                                       22

<210> SEQ ID NO 119
<211> LENGTH: 22
<212> TYPE: RNA
<213> ORGANISM: Arabidopsis thaliana

<400> SEQUENCE: 119
gaaacaaugc gaucccuuug ga                                       22

<210> SEQ ID NO 120
<211> LENGTH: 22
<212> TYPE: RNA
<213> ORGANISM: Arabidopsis thaliana

<400> SEQUENCE: 120
ggucagagcg aucccuuugg ca                                       22

<210> SEQ ID NO 121
<211> LENGTH: 22
<212> TYPE: RNA
<213> ORGANISM: Arabidopsis thaliana

<400> SEQUENCE: 121
gaaacaaugc gaucccuuug ga                                       22

<210> SEQ ID NO 122
<211> LENGTH: 21
<212> TYPE: RNA
<213> ORGANISM: Acorus americanus

<400> SEQUENCE: 122
aaacaaugcg aucccuuugg a                                        21

<210> SEQ ID NO 123
<211> LENGTH: 21
<212> TYPE: RNA
<213> ORGANISM: Ananas comosus

<400> SEQUENCE: 123
aaacaaugcg aucccuuugg a                                        21

<210> SEQ ID NO 124
<211> LENGTH: 21
<212> TYPE: RNA
<213> ORGANISM: Ananas comosus

<400> SEQUENCE: 124
aaacaaugcg aucccuuugg a                                               21

<210> SEQ ID NO 125
<211> LENGTH: 21
<212> TYPE: RNA
<213> ORGANISM: Aquilegia formosa x Aquilegia pubescens

<400> SEQUENCE: 125
aaacaaugcg aucccuuugg a                                               21

<210> SEQ ID NO 126
<211> LENGTH: 21
<212> TYPE: RNA
<213> ORGANISM: Brassica rapa subsp. pekinesis

<400> SEQUENCE: 126
aaacaaugcg aucccuuugg a                                               21

<210> SEQ ID NO 127
<211> LENGTH: 21
<212> TYPE: RNA
<213> ORGANISM: Citrus sinensis

<400> SEQUENCE: 127
aaucuaugag aucacuuugg a                                               21

<210> SEQ ID NO 128
<211> LENGTH: 21
<212> TYPE: RNA
<213> ORGANISM: Coffea arabica

<400> SEQUENCE: 128
aaacaaugcg aucccuuugg a                                               21

<210> SEQ ID NO 129
<211> LENGTH: 21
<212> TYPE: RNA
<213> ORGANISM: Coffea canephora

<400> SEQUENCE: 129
aaacaaugcg aucccuuugg a                                               21

<210> SEQ ID NO 130
<211> LENGTH: 21
<212> TYPE: RNA
<213> ORGANISM: Coffea canephora

<400> SEQUENCE: 130
aaacaaugcg aucccuuugg a                                               21

<210> SEQ ID NO 131
<211> LENGTH: 21
<212> TYPE: RNA
<213> ORGANISM: Coffea canephora

<400> SEQUENCE: 131
aaaccaugcu aucccuuugg a                                               21

```
<210> SEQ ID NO 132
<211> LENGTH: 21
<212> TYPE: RNA
<213> ORGANISM: Coffea canephora

<400> SEQUENCE: 132
aaacaaugcg aucccuuugg a                                              21

<210> SEQ ID NO 133
<211> LENGTH: 21
<212> TYPE: RNA
<213> ORGANISM: Coffea canephora

<400> SEQUENCE: 133
aaacaaugcg aucccuuugg a                                              21

<210> SEQ ID NO 134
<211> LENGTH: 21
<212> TYPE: RNA
<213> ORGANISM: Eucalyptus tereticornis

<400> SEQUENCE: 134
aaacaaugcg aucccuuugg a                                              21

<210> SEQ ID NO 135
<211> LENGTH: 21
<212> TYPE: RNA
<213> ORGANISM: Glycine max

<400> SEQUENCE: 135
aaacaaugcg aucccuuugg a                                              21

<210> SEQ ID NO 136
<211> LENGTH: 21
<212> TYPE: RNA
<213> ORGANISM: Glycine max

<400> SEQUENCE: 136
aaacgaugcg aucccuuugg a                                              21

<210> SEQ ID NO 137
<211> LENGTH: 21
<212> TYPE: RNA
<213> ORGANISM: Glycine max

<400> SEQUENCE: 137
aaacaaugcg aucccuuugg a                                              21

<210> SEQ ID NO 138
<211> LENGTH: 21
<212> TYPE: RNA
<213> ORGANISM: Glycine max

<400> SEQUENCE: 138
aaacaaugcg aucccuuugg a                                              21

<210> SEQ ID NO 139
<211> LENGTH: 21
<212> TYPE: RNA
<213> ORGANISM: Glycine max

<400> SEQUENCE: 139
aaacaaugcg aucccuuugg a                                              21
```

<210> SEQ ID NO 140
<211> LENGTH: 21
<212> TYPE: RNA
<213> ORGANISM: Glycine max

<400> SEQUENCE: 140
aaacaaugcg aucccuuugg a                                              21

<210> SEQ ID NO 141
<211> LENGTH: 21
<212> TYPE: RNA
<213> ORGANISM: Glycine max

<400> SEQUENCE: 141
aaacaaugcg aucccuuugg a                                              21

<210> SEQ ID NO 142
<211> LENGTH: 21
<212> TYPE: RNA
<213> ORGANISM: Glycine max

<400> SEQUENCE: 142
aaacaaugcg aucccuuugg a                                              21

<210> SEQ ID NO 143
<211> LENGTH: 21
<212> TYPE: RNA
<213> ORGANISM: Glycine max

<400> SEQUENCE: 143
aaacaaugcg aucccuuugg a                                              21

<210> SEQ ID NO 144
<211> LENGTH: 21
<212> TYPE: RNA
<213> ORGANISM: Glycine max

<400> SEQUENCE: 144
aaacaaugcg aucccuuugg a                                              21

<210> SEQ ID NO 145
<211> LENGTH: 21
<212> TYPE: RNA
<213> ORGANISM: Glycine max

<400> SEQUENCE: 145
aaacaaugcg aucccuuugg a                                              21

<210> SEQ ID NO 146
<211> LENGTH: 21
<212> TYPE: RNA
<213> ORGANISM: Glycine max

<400> SEQUENCE: 146
aaacaaugcg aucccuuugg a                                              21

<210> SEQ ID NO 147
<211> LENGTH: 21
<212> TYPE: RNA
<213> ORGANISM: Glycine max

<400> SEQUENCE: 147
aaacaaugcg aucccuuugg a                                              21

<210> SEQ ID NO 148
<211> LENGTH: 21
<212> TYPE: RNA
<213> ORGANISM: Glycine max

<400> SEQUENCE: 148
aaacaaugcg aucccuuugg a                                              21

<210> SEQ ID NO 149
<211> LENGTH: 21
<212> TYPE: RNA
<213> ORGANISM: Glycine max

<400> SEQUENCE: 149
aaacaaugcg aucccuuugg a                                              21

<210> SEQ ID NO 150
<211> LENGTH: 21
<212> TYPE: RNA
<213> ORGANISM: Glycine max

<400> SEQUENCE: 150
aaacaaugcg aucccuuugg a                                              21

<210> SEQ ID NO 151
<211> LENGTH: 21
<212> TYPE: RNA
<213> ORGANISM: Glycine max

<400> SEQUENCE: 151
aaacaaugcg aucccuuugg a                                              21

<210> SEQ ID NO 152
<211> LENGTH: 21
<212> TYPE: RNA
<213> ORGANISM: Glycine max

<400> SEQUENCE: 152
aaacaaugcg aucccuuugg a                                              21

<210> SEQ ID NO 153
<211> LENGTH: 21
<212> TYPE: RNA
<213> ORGANISM: Glycine max

<400> SEQUENCE: 153
aaacaaugcg aucccuuugg a                                              21

<210> SEQ ID NO 154
<211> LENGTH: 21
<212> TYPE: RNA
<213> ORGANISM: Glycine soja

<400> SEQUENCE: 154
aaacaaugcg aucccuuugg a                                              21

<210> SEQ ID NO 155
<211> LENGTH: 21
<212> TYPE: RNA
<213> ORGANISM: Gossypium arboreum

<400> SEQUENCE: 155
aaacaaugcg aucccuuugg a                                              21

```
<210> SEQ ID NO 156
<211> LENGTH: 21
<212> TYPE: RNA
<213> ORGANISM: Gossypium hirsutum

<400> SEQUENCE: 156
aaacaaugcg aucccuuugg a                                              21

<210> SEQ ID NO 157
<211> LENGTH: 21
<212> TYPE: RNA
<213> ORGANISM: Gossypium hirsutum

<400> SEQUENCE: 157
aaacaaugcg aucccuuugg a                                              21

<210> SEQ ID NO 158
<211> LENGTH: 21
<212> TYPE: RNA
<213> ORGANISM: Gossypium hirsutum

<400> SEQUENCE: 158
aaacaaugcg aucccuuugg a                                              21

<210> SEQ ID NO 159
<211> LENGTH: 21
<212> TYPE: RNA
<213> ORGANISM: Helianthus argophyllus

<400> SEQUENCE: 159
agucaaugcg aucccugugg a                                              21

<210> SEQ ID NO 160
<211> LENGTH: 21
<212> TYPE: RNA
<213> ORGANISM: Helianthus argophyllus

<400> SEQUENCE: 160
agucaaugcg aucccugugg a                                              21

<210> SEQ ID NO 161
<211> LENGTH: 21
<212> TYPE: RNA
<213> ORGANISM: Helianthus petiolaris

<400> SEQUENCE: 161
aaucaaugag gucucuuugg a                                              21

<210> SEQ ID NO 162
<211> LENGTH: 21
<212> TYPE: RNA
<213> ORGANISM: Lactuca sativa

<400> SEQUENCE: 162
aaucaaugag gucucuuugg a                                              21

<210> SEQ ID NO 163
<211> LENGTH: 21
<212> TYPE: RNA
<213> ORGANISM: Lactuca sativa

<400> SEQUENCE: 163
aaucaaugag gucucuuugg a                                              21
```

```
<210> SEQ ID NO 164
<211> LENGTH: 21
<212> TYPE: RNA
<213> ORGANISM: Lotus japonicus

<400> SEQUENCE: 164
gcacgaggcg aucccuuugg a                                          21

<210> SEQ ID NO 165
<211> LENGTH: 21
<212> TYPE: RNA
<213> ORGANISM: Malus x domestica

<400> SEQUENCE: 165
aagcaaugcg aucccuuugg a                                          21

<210> SEQ ID NO 166
<211> LENGTH: 21
<212> TYPE: RNA
<213> ORGANISM: Malus x domestica

<400> SEQUENCE: 166
aaacaaugcg aucccuuugg a                                          21

<210> SEQ ID NO 167
<211> LENGTH: 21
<212> TYPE: RNA
<213> ORGANISM: Malus x domestica

<400> SEQUENCE: 167
aagcaaugcg aucccuuugg a                                          21

<210> SEQ ID NO 168
<211> LENGTH: 21
<212> TYPE: RNA
<213> ORGANISM: Malus x domestica

<400> SEQUENCE: 168
aagcaaugcg aucccuuugg a                                          21

<210> SEQ ID NO 169
<211> LENGTH: 21
<212> TYPE: RNA
<213> ORGANISM: Malus x domestica

<400> SEQUENCE: 169
aagcaaugcg aucccuuugg a                                          21

<210> SEQ ID NO 170
<211> LENGTH: 21
<212> TYPE: RNA
<213> ORGANISM: Malus x domestica

<400> SEQUENCE: 170
aaacaaugcg aucccuuugg a                                          21

<210> SEQ ID NO 171
<211> LENGTH: 21
<212> TYPE: RNA
<213> ORGANISM: Malus x domestica

<400> SEQUENCE: 171
aagcaaugcg aucccuuugg a                                          21
```

-continued

<210> SEQ ID NO 172
<211> LENGTH: 21
<212> TYPE: RNA
<213> ORGANISM: Malus x domestica

<400> SEQUENCE: 172
aagcaaugcg aucccuuugg a                                              21

<210> SEQ ID NO 173
<211> LENGTH: 21
<212> TYPE: RNA
<213> ORGANISM: Malus x domestica

<400> SEQUENCE: 173
aagcaaugcg aucccuuugg a                                              21

<210> SEQ ID NO 174
<211> LENGTH: 21
<212> TYPE: RNA
<213> ORGANISM: Malus x domestica

<400> SEQUENCE: 174
aaacaaugcg aucccuuugg a                                              21

<210> SEQ ID NO 175
<211> LENGTH: 21
<212> TYPE: RNA
<213> ORGANISM: Malus x domestica

<400> SEQUENCE: 175
aaacacugcg aucccuuugg a                                              21

<210> SEQ ID NO 176
<211> LENGTH: 21
<212> TYPE: RNA
<213> ORGANISM: Malus x domestica

<400> SEQUENCE: 176
aaacaaugcg aucccuuugg a                                              21

<210> SEQ ID NO 177
<211> LENGTH: 21
<212> TYPE: RNA
<213> ORGANISM: Malus x domestica

<400> SEQUENCE: 177
aagcaaugcg aucccuuugg a                                              21

<210> SEQ ID NO 178
<211> LENGTH: 21
<212> TYPE: RNA
<213> ORGANISM: Malus x domestica

<400> SEQUENCE: 178
aagcaaugcg aucccuuugg a                                              21

<210> SEQ ID NO 179
<211> LENGTH: 21
<212> TYPE: RNA
<213> ORGANISM: Malus x domestica

<400> SEQUENCE: 179
aaacaaugcg aucccuuugg a                                              21

```
<210> SEQ ID NO 180
<211> LENGTH: 21
<212> TYPE: RNA
<213> ORGANISM: Malus x domestica

<400> SEQUENCE: 180
aagcaaugcg aucccuuugg a                                              21

<210> SEQ ID NO 181
<211> LENGTH: 21
<212> TYPE: RNA
<213> ORGANISM: Malus x domestica

<400> SEQUENCE: 181
aagcaaugcg aucccuuugg a                                              21

<210> SEQ ID NO 182
<211> LENGTH: 21
<212> TYPE: RNA
<213> ORGANISM: Manihot esculenta

<400> SEQUENCE: 182
aaacaaugcg aucccuuugg a                                              21

<210> SEQ ID NO 183
<211> LENGTH: 21
<212> TYPE: RNA
<213> ORGANISM: Medicago truncatula

<400> SEQUENCE: 183
aaacaaugcg aucccuuugg a                                              21

<210> SEQ ID NO 184
<211> LENGTH: 21
<212> TYPE: RNA
<213> ORGANISM: Medicago truncatula

<400> SEQUENCE: 184
aaacaaugcg aucccuuugg a                                              21

<210> SEQ ID NO 185
<211> LENGTH: 21
<212> TYPE: RNA
<213> ORGANISM: Medicago truncatula

<400> SEQUENCE: 185
aaacaaugcg aucccuuugg a                                              21

<210> SEQ ID NO 186
<211> LENGTH: 21
<212> TYPE: RNA
<213> ORGANISM: Medicago truncatula

<400> SEQUENCE: 186
aaacaaugcg aucccuuugg a                                              21

<210> SEQ ID NO 187
<211> LENGTH: 21
<212> TYPE: RNA
<213> ORGANISM: Medicago truncatula

<400> SEQUENCE: 187
aaacaaugcg aucccuuugg a                                              21
```

<210> SEQ ID NO 188
<211> LENGTH: 21
<212> TYPE: RNA
<213> ORGANISM: Medicago truncatula

<400> SEQUENCE: 188
aaacaaugcg aucccuuugg a                                              21

<210> SEQ ID NO 189
<211> LENGTH: 21
<212> TYPE: RNA
<213> ORGANISM: Medicago truncatula

<400> SEQUENCE: 189
aaacaaugcg aucccuuugg a                                              21

<210> SEQ ID NO 190
<211> LENGTH: 21
<212> TYPE: RNA
<213> ORGANISM: Picea glauca

<400> SEQUENCE: 190
aaucaaugcg aucccuuugg a                                              21

<210> SEQ ID NO 191
<211> LENGTH: 21
<212> TYPE: RNA
<213> ORGANISM: Pinus taeda

<400> SEQUENCE: 191
aaucaaugcg aucccuuugg a                                              21

<210> SEQ ID NO 192
<211> LENGTH: 21
<212> TYPE: RNA
<213> ORGANISM: Pinus taeda

<400> SEQUENCE: 192
aaucaaugcg aucccuuugg a                                              21

<210> SEQ ID NO 193
<211> LENGTH: 21
<212> TYPE: RNA
<213> ORGANISM: Pinus taeda

<400> SEQUENCE: 193
aaucaaugcg aucccuuugg a                                              21

<210> SEQ ID NO 194
<211> LENGTH: 21
<212> TYPE: RNA
<213> ORGANISM: Pinus taeda

<400> SEQUENCE: 194
aaucaaugcg aucccuuugg a                                              21

<210> SEQ ID NO 195
<211> LENGTH: 21
<212> TYPE: RNA
<213> ORGANISM: Pinus taeda

<400> SEQUENCE: 195
aaucaaugcg aucccuuugg a                                              21

<210> SEQ ID NO 196
<211> LENGTH: 21
<212> TYPE: RNA
<213> ORGANISM: Poncirus trifoliata

<400> SEQUENCE: 196
gaucagagcg aucccuuuga a                                              21

<210> SEQ ID NO 197
<211> LENGTH: 21
<212> TYPE: RNA
<213> ORGANISM: Populus tremula x Populus tremuloides

<400> SEQUENCE: 197
aaacaaugcg aucccuuugg a                                              21

<210> SEQ ID NO 198
<211> LENGTH: 21
<212> TYPE: RNA
<213> ORGANISM: Populus tremula x Populus tremuloides

<400> SEQUENCE: 198
aaacaaugcg aucccuuugg a                                              21

<210> SEQ ID NO 199
<211> LENGTH: 21
<212> TYPE: RNA
<213> ORGANISM: Populus tremula x Populus tremuloides

<400> SEQUENCE: 199
aaacaaugcg aucccuuugg a                                              21

<210> SEQ ID NO 200
<211> LENGTH: 21
<212> TYPE: RNA
<213> ORGANISM: Populus tremuloides

<400> SEQUENCE: 200
aaacaaugcg aucccuuugg a                                              21

<210> SEQ ID NO 201
<211> LENGTH: 21
<212> TYPE: RNA
<213> ORGANISM: Populus trichocarpa

<400> SEQUENCE: 201
aaacaaugcg aucccuuugg a                                              21

<210> SEQ ID NO 202
<211> LENGTH: 21
<212> TYPE: RNA
<213> ORGANISM: Populus trichocarpa x Populus deltoides

<400> SEQUENCE: 202
aaacaaugcg aucccuuugg a                                              21

<210> SEQ ID NO 203
<211> LENGTH: 21
<212> TYPE: RNA
<213> ORGANISM: Populus trichocarpa x Populus deltoides

<400> SEQUENCE: 203
aaacaaugcg aucccuuugg a                                              21

```
<210> SEQ ID NO 204
<211> LENGTH: 21
<212> TYPE: RNA
<213> ORGANISM: Populus x canadensis

<400> SEQUENCE: 204
aaacaaugcg aucccuuugg a                                              21

<210> SEQ ID NO 205
<211> LENGTH: 21
<212> TYPE: RNA
<213> ORGANISM: Prunus persica

<400> SEQUENCE: 205
aaucuaugag aucacuuugg a                                              21

<210> SEQ ID NO 206
<211> LENGTH: 21
<212> TYPE: RNA
<213> ORGANISM: Ricinus communis

<400> SEQUENCE: 206
aaacaaugcg aucccuuugg a                                              21

<210> SEQ ID NO 207
<211> LENGTH: 21
<212> TYPE: RNA
<213> ORGANISM: Saruma henryi

<400> SEQUENCE: 207
aaacaaugcg aucccuuugg a                                              21

<210> SEQ ID NO 208
<211> LENGTH: 21
<212> TYPE: RNA
<213> ORGANISM: Zingiber officinale

<400> SEQUENCE: 208
aaacaaugcg aucccuuugg a                                              21

<210> SEQ ID NO 209
<211> LENGTH: 21
<212> TYPE: RNA
<213> ORGANISM: Zingiber officinale

<400> SEQUENCE: 209
aaacaaugcg aucccuuugg a                                              21

<210> SEQ ID NO 210
<211> LENGTH: 21
<212> TYPE: RNA
<213> ORGANISM: Arabidopsis thaliana

<400> SEQUENCE: 210
cagauggugg aaaugggaua u                                              21

<210> SEQ ID NO 211
<211> LENGTH: 21
<212> TYPE: RNA
<213> ORGANISM: Arabidopsis thaliana

<400> SEQUENCE: 211
caaauggucg aaaugggaua u                                              21
```

<210> SEQ ID NO 212
<211> LENGTH: 21
<212> TYPE: RNA
<213> ORGANISM: Arabidopsis thaliana

<400> SEQUENCE: 212
caaauggugg aaaugggghua u                                              21

<210> SEQ ID NO 213
<211> LENGTH: 21
<212> TYPE: RNA
<213> ORGANISM: Arabidopsis thaliana

<400> SEQUENCE: 213
caaaggugcg aaaugggaua u                                               21

<210> SEQ ID NO 214
<211> LENGTH: 21
<212> TYPE: RNA
<213> ORGANISM: Arabidopsis thaliana

<400> SEQUENCE: 214
cagauggugg aaaugggaua u                                               21

<210> SEQ ID NO 215
<211> LENGTH: 21
<212> TYPE: RNA
<213> ORGANISM: Arabidopsis thaliana

<400> SEQUENCE: 215
caaauggugg aaauggggua u                                               21

<210> SEQ ID NO 216
<211> LENGTH: 21
<212> TYPE: RNA
<213> ORGANISM: Arabidopsis thaliana

<400> SEQUENCE: 216
caaauggugg aaauggggua u                                               21

<210> SEQ ID NO 217
<211> LENGTH: 21
<212> TYPE: RNA
<213> ORGANISM: Arabidopsis thaliana

<400> SEQUENCE: 217
caaauggugg gaaugggaua u                                               21

<210> SEQ ID NO 218
<211> LENGTH: 21
<212> TYPE: RNA
<213> ORGANISM: Arabidopsis thaliana

<400> SEQUENCE: 218
guugaucgua ugguagaaga a                                               21

<210> SEQ ID NO 219
<211> LENGTH: 21
<212> TYPE: RNA
<213> ORGANISM: Arabidopsis thaliana

<400> SEQUENCE: 219
aaggucuugc aaggucaaga a                                               21

```
<210> SEQ ID NO 220
<211> LENGTH: 21
<212> TYPE: RNA
<213> ORGANISM: Arabidopsis thaliana

<400> SEQUENCE: 220
agggucuugc aaggucaaga a                                             21

<210> SEQ ID NO 221
<211> LENGTH: 21
<212> TYPE: RNA
<213> ORGANISM: Citrus x paradisi

<400> SEQUENCE: 221
uugucuaucc cuccugagcu g                                             21

<210> SEQ ID NO 222
<211> LENGTH: 21
<212> TYPE: RNA
<213> ORGANISM: Manihot esculenta

<400> SEQUENCE: 222
uugucuaucc cuccugagcu a                                             21

<210> SEQ ID NO 223
<211> LENGTH: 21
<212> TYPE: RNA
<213> ORGANISM: Populus tremula x Populus tremuloides

<400> SEQUENCE: 223
uugucuaucc cuccugagcu g                                             21

<210> SEQ ID NO 224
<211> LENGTH: 21
<212> TYPE: RNA
<213> ORGANISM: Pinus taeda

<400> SEQUENCE: 224
uacucuaucu cuccugagcu a                                             21

<210> SEQ ID NO 225
<211> LENGTH: 21
<212> TYPE: RNA
<213> ORGANISM: Populus trichocarpa

<400> SEQUENCE: 225
uugucuaucc cuccugagcu a                                             21

<210> SEQ ID NO 226
<211> LENGTH: 21
<212> TYPE: RNA
<213> ORGANISM: Pinus taeda

<400> SEQUENCE: 226
uacucuaucu cuccugagcu a                                             21

<210> SEQ ID NO 227
<211> LENGTH: 21
<212> TYPE: RNA
<213> ORGANISM: Zea mays

<400> SEQUENCE: 227
agcucuaucc cuucugagcu g                                             21
```

<210> SEQ ID NO 228
<211> LENGTH: 21
<212> TYPE: RNA
<213> ORGANISM: Gossypium raimondii

<400> SEQUENCE: 228
cugucuaucc cuccugagcu a                                              21

<210> SEQ ID NO 229
<211> LENGTH: 21
<212> TYPE: RNA
<213> ORGANISM: Vitis vinifera

<400> SEQUENCE: 229
uugucuaucc cuccugagcu a                                              21

<210> SEQ ID NO 230
<211> LENGTH: 21
<212> TYPE: RNA
<213> ORGANISM: Euphorbia esula

<400> SEQUENCE: 230
uugucuaucc cuccugagcu u                                              21

<210> SEQ ID NO 231
<211> LENGTH: 21
<212> TYPE: RNA
<213> ORGANISM: Lycopersicon esculentum

<400> SEQUENCE: 231
uugucuaucc cuccugagcu g                                              21

<210> SEQ ID NO 232
<211> LENGTH: 21
<212> TYPE: RNA
<213> ORGANISM: Zea mays

<400> SEQUENCE: 232
ccuucuaucc cuccugagcu a                                              21

<210> SEQ ID NO 233
<211> LENGTH: 21
<212> TYPE: RNA
<213> ORGANISM: Vitis vinifera

<400> SEQUENCE: 233
uugucuaucc cuccugagcu a                                              21

<210> SEQ ID NO 234
<211> LENGTH: 21
<212> TYPE: RNA
<213> ORGANISM: Gossypium raimondii

<400> SEQUENCE: 234
cugucuaucc cuccugagcu a                                              21

<210> SEQ ID NO 235
<211> LENGTH: 21
<212> TYPE: RNA
<213> ORGANISM: Theobroma cacao

<400> SEQUENCE: 235
cuugcuaucc cuccugagcu g                                              21

```
<210> SEQ ID NO 236
<211> LENGTH: 21
<212> TYPE: RNA
<213> ORGANISM: Populus euphratica

<400> SEQUENCE: 236
uuggcuaucc cuccugagcu g                                              21

<210> SEQ ID NO 237
<211> LENGTH: 21
<212> TYPE: RNA
<213> ORGANISM: Hordeum vulgare

<400> SEQUENCE: 237
cuuucuaucc cuccugagcu a                                              21

<210> SEQ ID NO 238
<211> LENGTH: 21
<212> TYPE: RNA
<213> ORGANISM: Manihot esculenta

<400> SEQUENCE: 238
uugucuaucc cuccugagcu a                                              21

<210> SEQ ID NO 239
<211> LENGTH: 21
<212> TYPE: RNA
<213> ORGANISM: Malus x domestica

<400> SEQUENCE: 239
uugucuaucc cuccugagcu g                                              21

<210> SEQ ID NO 240
<211> LENGTH: 21
<212> TYPE: RNA
<213> ORGANISM: Glycine max

<400> SEQUENCE: 240
uugucuaucc cuccugagcu g                                              21

<210> SEQ ID NO 241
<211> LENGTH: 21
<212> TYPE: RNA
<213> ORGANISM: Sorghum bicolor

<400> SEQUENCE: 241
augucuaucc cuucugagcu g                                              21

<210> SEQ ID NO 242
<211> LENGTH: 21
<212> TYPE: RNA
<213> ORGANISM: Populus trichocarpa

<400> SEQUENCE: 242
uugucuaucc cuccugagcu a                                              21

<210> SEQ ID NO 243
<211> LENGTH: 21
<212> TYPE: RNA
<213> ORGANISM: Vitis vinifera

<400> SEQUENCE: 243
uugucuaucc cuccugagcu a                                              21
```

-continued

<210> SEQ ID NO 244
<211> LENGTH: 21
<212> TYPE: RNA
<213> ORGANISM: Citrus x paradise x Poncirus trifoliata

<400> SEQUENCE: 244
uugucuaucc cuccugagcu g                                              21

<210> SEQ ID NO 245
<211> LENGTH: 21
<212> TYPE: RNA
<213> ORGANISM: Bruguiera gymnorhiza

<400> SEQUENCE: 245
uugucuaucc cuccugagcu g                                              21

<210> SEQ ID NO 246
<211> LENGTH: 21
<212> TYPE: RNA
<213> ORGANISM: Sorghum bicolor

<400> SEQUENCE: 246
augucuaucc cuucugagcu g                                              21

<210> SEQ ID NO 247
<211> LENGTH: 21
<212> TYPE: RNA
<213> ORGANISM: Triticum aestivum

<400> SEQUENCE: 247
ccaucuaucc cuccugagcu a                                              21

<210> SEQ ID NO 248
<211> LENGTH: 21
<212> TYPE: RNA
<213> ORGANISM: Malus x domestica

<400> SEQUENCE: 248
uugucuaucc cuccugagcu g                                              21

<210> SEQ ID NO 249
<211> LENGTH: 21
<212> TYPE: RNA
<213> ORGANISM: Oryza sativa

<400> SEQUENCE: 249
cggucuaucc cuccugagcu g                                              21

<210> SEQ ID NO 250
<211> LENGTH: 21
<212> TYPE: RNA
<213> ORGANISM: Zea mays

<400> SEQUENCE: 250
agcucuaucc cuucugagcu u                                              21

<210> SEQ ID NO 251
<211> LENGTH: 21
<212> TYPE: RNA
<213> ORGANISM: Populus tremula

<400> SEQUENCE: 251
uugucuaucc cuccugagcu g                                              21

-continued

```
<210> SEQ ID NO 252
<211> LENGTH: 21
<212> TYPE: RNA
<213> ORGANISM: Antirrhinum majus

<400> SEQUENCE: 252
uugucuaucc cuccugagcu a                                              21

<210> SEQ ID NO 253
<211> LENGTH: 21
<212> TYPE: RNA
<213> ORGANISM: Sorghum bicolor

<400> SEQUENCE: 253
augucuaucc cuucugagcu g                                              21

<210> SEQ ID NO 254
<211> LENGTH: 21
<212> TYPE: RNA
<213> ORGANISM: Populus trichocarpa x Populus deltoides

<400> SEQUENCE: 254
uuaucuaucc cuccugagcu a                                              21

<210> SEQ ID NO 255
<211> LENGTH: 21
<212> TYPE: RNA
<213> ORGANISM: Mesembryanthemum crystallinum

<400> SEQUENCE: 255
gugucuaucc cuccugagcu a                                              21

<210> SEQ ID NO 256
<211> LENGTH: 21
<212> TYPE: RNA
<213> ORGANISM: Zea mays

<400> SEQUENCE: 256
augucuaucc cuucugagcu g                                              21

<210> SEQ ID NO 257
<211> LENGTH: 21
<212> TYPE: RNA
<213> ORGANISM: Populus trichocarpa

<400> SEQUENCE: 257
uuaucuaucc cuccugagcu a                                              21

<210> SEQ ID NO 258
<211> LENGTH: 21
<212> TYPE: RNA
<213> ORGANISM: Populus trichocarpa

<400> SEQUENCE: 258
uugucuaucc cuccugagcu a                                              21

<210> SEQ ID NO 259
<211> LENGTH: 21
<212> TYPE: RNA
<213> ORGANISM: Antirrhinum majus

<400> SEQUENCE: 259
uugucuaucc cuccugagcu a                                              21
```

```
<210> SEQ ID NO 260
<211> LENGTH: 21
<212> TYPE: RNA
<213> ORGANISM: Zea mays

<400> SEQUENCE: 260
augucuaucc cuucugagcu g                                              21

<210> SEQ ID NO 261
<211> LENGTH: 21
<212> TYPE: RNA
<213> ORGANISM: Populus deltoides

<400> SEQUENCE: 261
uugucuaucc cuccugagcu a                                              21

<210> SEQ ID NO 262
<211> LENGTH: 21
<212> TYPE: RNA
<213> ORGANISM: Triticum aestivum

<400> SEQUENCE: 262
ccaucuaucc cuccggagcu a                                              21

<210> SEQ ID NO 263
<211> LENGTH: 21
<212> TYPE: RNA
<213> ORGANISM: Citrus clementina

<400> SEQUENCE: 263
uugucuaucc cuccugagcu g                                              21

<210> SEQ ID NO 264
<211> LENGTH: 21
<212> TYPE: RNA
<213> ORGANISM: Glycine soja

<400> SEQUENCE: 264
uugucuaucc cuccugagcu g                                              21

<210> SEQ ID NO 265
<211> LENGTH: 21
<212> TYPE: RNA
<213> ORGANISM: Manihot esculenta

<400> SEQUENCE: 265
uugucuaucc cuccugagcu a                                              21

<210> SEQ ID NO 266
<211> LENGTH: 22
<212> TYPE: RNA
<213> ORGANISM: Populus trichocarpa x Populus deltoides
<220> FEATURE:
<221> NAME/KEY: modified_base
<222> LOCATION: (3)..(5)
<223> OTHER INFORMATION: a, c, u, g, unknown or other

<400> SEQUENCE: 266
uunnnuaucc cuccugagcu au                                             22

<210> SEQ ID NO 267
<211> LENGTH: 21
<212> TYPE: RNA
<213> ORGANISM: Populus deltoides
```

-continued

<400> SEQUENCE: 267
uuaucuaucc cuccugagcu g    21

<210> SEQ ID NO 268
<211> LENGTH: 21
<212> TYPE: RNA
<213> ORGANISM: Sorghum bicolor

<400> SEQUENCE: 268
augucuaucc cuucugagcu g    21

<210> SEQ ID NO 269
<211> LENGTH: 21
<212> TYPE: RNA
<213> ORGANISM: Saccharum officinarum

<400> SEQUENCE: 269
augucuaucc cuucugagcu g    21

<210> SEQ ID NO 270
<211> LENGTH: 21
<212> TYPE: RNA
<213> ORGANISM: Zea mays

<400> SEQUENCE: 270
agcucuaucc cuucugagcu g    21

<210> SEQ ID NO 271
<211> LENGTH: 21
<212> TYPE: RNA
<213> ORGANISM: Populus trichocarpa

<400> SEQUENCE: 271
uuaucuaucc cuccugagcu a    21

<210> SEQ ID NO 272
<211> LENGTH: 21
<212> TYPE: RNA
<213> ORGANISM: Zea mays

<400> SEQUENCE: 272
augucuaucc cuucugaacu g    21

<210> SEQ ID NO 273
<211> LENGTH: 21
<212> TYPE: RNA
<213> ORGANISM: Zea mays

<400> SEQUENCE: 273
ccuucuaucc cuccugagcu a    21

<210> SEQ ID NO 274
<211> LENGTH: 21
<212> TYPE: RNA
<213> ORGANISM: Triticum aestivum

<400> SEQUENCE: 274
ccaucuaucc cuccugagcu a    21

<210> SEQ ID NO 275
<211> LENGTH: 21
<212> TYPE: RNA
<213> ORGANISM: Populus trichocarpa

```
<400> SEQUENCE: 275
uuaucuaucc cuccgagcu a                                              21

<210> SEQ ID NO 276
<211> LENGTH: 21
<212> TYPE: RNA
<213> ORGANISM: Populus deltoides

<400> SEQUENCE: 276
uugucuaucc cuccgagcu a                                              21

<210> SEQ ID NO 277
<211> LENGTH: 21
<212> TYPE: RNA
<213> ORGANISM: Saccharum officinarum

<400> SEQUENCE: 277
augucuaucc cuucgagcu a                                              21

<210> SEQ ID NO 278
<211> LENGTH: 21
<212> TYPE: RNA
<213> ORGANISM: Arabidopsis thaliana

<400> SEQUENCE: 278
uugucuaucc cuccgagcu a                                              21

<210> SEQ ID NO 279
<211> LENGTH: 21
<212> TYPE: RNA
<213> ORGANISM: Arabidopsis thaliana

<400> SEQUENCE: 279
guuacuuaca acacucucau a                                             21

<210> SEQ ID NO 280
<211> LENGTH: 21
<212> TYPE: RNA
<213> ORGANISM: Arabidopsis thaliana

<400> SEQUENCE: 280
guuacuuaca acacucucau a                                             21

<210> SEQ ID NO 281
<211> LENGTH: 21
<212> TYPE: RNA
<213> ORGANISM: Arabidopsis thaliana

<400> SEQUENCE: 281
agggucuugc aaggucaaga a                                             21

<210> SEQ ID NO 282
<211> LENGTH: 21
<212> TYPE: RNA
<213> ORGANISM: Arabidopsis thaliana

<400> SEQUENCE: 282
aaggucuugc aaggucaaga a                                             21

<210> SEQ ID NO 283
<211> LENGTH: 21
<212> TYPE: RNA
<213> ORGANISM: Physcomitrella patens
```

```
<400> SEQUENCE: 283
ggcguuaucc cucuugagcu g                                        21

<210> SEQ ID NO 284
<211> LENGTH: 22
<212> TYPE: RNA
<213> ORGANISM: Physcomitrella patens

<400> SEQUENCE: 284
guuguauauc acuccugagc ua                                       22

<210> SEQ ID NO 285
<211> LENGTH: 21
<212> TYPE: RNA
<213> ORGANISM: Physcomitrella patens

<400> SEQUENCE: 285
ggcgguaacc cuucugagcu a                                        21

<210> SEQ ID NO 286
<211> LENGTH: 21
<212> TYPE: RNA
<213> ORGANISM: Physcomitrella patens

<400> SEQUENCE: 286
uugucuauca cucuugagcu a                                        21

<210> SEQ ID NO 287
<211> LENGTH: 21
<212> TYPE: RNA
<213> ORGANISM: Physcomitrella patens

<400> SEQUENCE: 287
gacgcuaccc uuccugagcu a                                        21

<210> SEQ ID NO 288
<211> LENGTH: 22
<212> TYPE: RNA
<213> ORGANISM: Physcomitrella patens

<400> SEQUENCE: 288 uuugcuauc acucuugagc ua                                        22

<210> SEQ ID NO 289
<211> LENGTH: 21
<212> TYPE: RNA
<213> ORGANISM: Physcomitrella patens

<400> SEQUENCE: 289
ggcgcuaucc cuccugagcu u                                        21

<210> SEQ ID NO 290
<211> LENGTH: 22
<212> TYPE: RNA
<213> ORGANISM: Physcomitrella patens

<400> SEQUENCE: 290
guuuuauauc acuccugagc ua                                       22

<210> SEQ ID NO 291
<211> LENGTH: 22
<212> TYPE: RNA
<213> ORGANISM: Arabidopsis thaliana
```

```
<400> SEQUENCE: 291
cuugucuauc ccuccugagc ua                                              22

<210> SEQ ID NO 292
<211> LENGTH: 85
<212> TYPE: DNA
<213> ORGANISM: Bruguiera sp.

<400> SEQUENCE: 292
ggtgctatcc tacctgagct tttcttgacc ttgtaagacc ttttcttgac cttgtaagac     60
cccccttgtc tatccctcct gagct                                           85

<210> SEQ ID NO 293
<211> LENGTH: 85
<212> TYPE: DNA
<213> ORGANISM: Manihot sp.

<400> SEQUENCE: 293
ggtgctatcc tacctgagct tttcttgacc ttgtaagacc ttttcttgac cttgtaagac     60
cccccttgtc tatccctcct gagct                                           85

<210> SEQ ID NO 294
<211> LENGTH: 86
<212> TYPE: DNA
<213> ORGANISM: Populus sp.

<400> SEQUENCE: 294
ggtgctatcc tacctgagct tttcttgacc ttgtaagacc ttttcttgac cttgtaagac     60
cccccttgtc tatccctcct gagcta                                          86

<210> SEQ ID NO 295
<211> LENGTH: 85
<212> TYPE: DNA
<213> ORGANISM: Malus sp.

<400> SEQUENCE: 295
ggtgctatcc tagctgagct tttcttgacc ttgtaagacc ttttcttgac cttgtaagat     60
gtcccttgtc tatccctcct gagct                                           85

<210> SEQ ID NO 296
<211> LENGTH: 85
<212> TYPE: DNA
<213> ORGANISM: Glycine sp.

<400> SEQUENCE: 296
ggtgctatcc tatctgagct tttcttgacc ttgtaagacc ttttcttgac cttgtaagac     60
ctcccttgtc tatccctcct gagct                                           85

<210> SEQ ID NO 297
<211> LENGTH: 86
<212> TYPE: DNA
<213> ORGANISM: Arabidopsis sp.

<400> SEQUENCE: 297
ggtgttatcc tatctgagct tttcttgacc ttgtaaggcc ttttcttgac cttgtaagac     60
cccccttgtc tatccctcct gagcta                                          86

<210> SEQ ID NO 298
<211> LENGTH: 85
```

```
<212> TYPE: DNA
<213> ORGANISM: Citrus sp.

<400> SEQUENCE: 298
ggtgctatcc tacctgagct tttcttgacc ttgtaagacc ttttcttgac cttgtaagac      60
cccccttgtc tatccctcct gagct                                            85

<210> SEQ ID NO 299
<211> LENGTH: 86
<212> TYPE: DNA
<213> ORGANISM: Gossypium sp.

<400> SEQUENCE: 299
ggtgctatcc cacctgagct tttcttgacc ttgtaaggcc ttttcttgac cttgtaagac      60 ccccctgtc tatccctcct gagcta                                            86

<210> SEQ ID NO 300
<211> LENGTH: 85
<212> TYPE: DNA
<213> ORGANISM: Theobroma sp.
<220> FEATURE:
<221> NAME/KEY: modified_base
<222> LOCATION: (55)..(55)
<223> OTHER INFORMATION: a, c, t, g, unknown or other

<400> SEQUENCE: 300
ggtgctatcc tacctgagct tttcttgacc ttgtaagacc ttttcttgac cttgnaagac      60
ccctccttgc tatccctcct gagct                                            85

<210> SEQ ID NO 301
<211> LENGTH: 85
<212> TYPE: DNA
<213> ORGANISM: Vitis sp.

<400> SEQUENCE: 301
ggtgctatcc tacctgagct tttcttgacc ttgtaagacc ttttcttgac cttgtaagac      60
cctccttgtc tatccctcct gagct                                            85

<210> SEQ ID NO 302
<211> LENGTH: 86
<212> TYPE: DNA
<213> ORGANISM: Mesembryanthemum sp.

<400> SEQUENCE: 302
ggtgctatcc tacctgagct tttcttgacc ttgtaagacc ttttcttgac cttgtaagac      60
ctattgtgtc tatccctcct gagcta                                           86

<210> SEQ ID NO 303
<211> LENGTH: 85
<212> TYPE: DNA
<213> ORGANISM: Antirrhinum sp.

<400> SEQUENCE: 303
ggtgctatcc tatctgagct tttcttgacc ttgtaagacc ttttcttgac cttgtaagac      60
cccccttgtc tatccctcct gagct                                            85

<210> SEQ ID NO 304
<211> LENGTH: 85
<212> TYPE: DNA
<213> ORGANISM: Lycopersicon sp.

<400> SEQUENCE: 304
```

```
ggtgctatcc tacctgagct tttcttgacc ttgtaagacc ttttcttgac cttgtaagac    60 ccccttgtc tatccctcct gagct                                          85
```

<210> SEQ ID NO 305
<211> LENGTH: 87
<212> TYPE: DNA
<213> ORGANISM: Hordeum sp.

<400> SEQUENCE: 305

```
ggtgttatcc cgaatgagct tttcttgacc ttgtaaggcc ttttcttgac cttgtaaggc    60 cctcccttt ctatccctcc tgagcta                                         87
```

<210> SEQ ID NO 306
<211> LENGTH: 86
<212> TYPE: DNA
<213> ORGANISM: Oryza sp.

<400> SEQUENCE: 306

```
ggtgttatcc taactgagct tttcttgacc ttgcaagacc ttttcttgac cttgtaagac    60
ccactcggtc tatccctcct gagctg                                        86
```

<210> SEQ ID NO 307
<211> LENGTH: 86
<212> TYPE: DNA
<213> ORGANISM: Triticum sp.

<400> SEQUENCE: 307

```
ggtgttatcc tgattgagct tttcttgacc ttgcaagacc ttttcttgac cttgtaagac    60
ccattccatc tatccctcct gagcta                                        86
```

<210> SEQ ID NO 308
<211> LENGTH: 86
<212> TYPE: DNA
<213> ORGANISM: Saccharum sp.

<400> SEQUENCE: 308

```
ggtgttatcc caattgagct tttcttgacc ttgcaagacc ttttcttgac cttgtaagac    60
ccactatgtc tatcccttct gagctg                                        86
```

<210> SEQ ID NO 309
<211> LENGTH: 86
<212> TYPE: DNA
<213> ORGANISM: Sorghum sp.

<400> SEQUENCE: 309

```
ggcgttatcc tgattgagct tttcttgacc ttgcaagacc ttttcttgac cttgtaagac    60
ccactatgtc tatcccttct gagctg                                        86
```

<210> SEQ ID NO 310
<211> LENGTH: 86
<212> TYPE: DNA
<213> ORGANISM: Zea sp.

<400> SEQUENCE: 310

```
ggtgttatcc cgactgaact tttcttgacc ttgtaaggcc tcttcttgac cttgtaaggc    60 tctcccttc tatccctcct gagcta                                         86
```

<210> SEQ ID NO 311
<211> LENGTH: 86

```
<212> TYPE: DNA
<213> ORGANISM: Pinus sp.

<400> SEQUENCE: 311
gacgctatcc cctctgagct tttcttgacc ttgtacgacc ttttcttgac cttgtaagac      60
ccacttactc tatctctcct gagcta                                          86

<210> SEQ ID NO 312
<211> LENGTH: 305
<212> TYPE: DNA
<213> ORGANISM: Bruguiera sp.

<400> SEQUENCE: 312
gtggcttgtt aatgtaaaat gggtgctatc ctacctgagc tttttatatt gctaccctct      60
tctctcaaca ttctttttt ctcttctgat tacattttca tgttttcctt gaccttgtaa     120
gaccttttct tgaccttgta agacccgtt ctgtcttctt acctttatt tcgtgtgctt     180 tcaggaactt tatatcagaa tcttgcgata taaagttcga gtacttcctt ttctgtttc     240 cgctgagccc atcttcttct tccttgtcta tccctcctga gctgtttaaa ttagactgtg     300
agaga                                                                305

<210> SEQ ID NO 313
<211> LENGTH: 290
<212> TYPE: DNA
<213> ORGANISM: Manihot sp.

<400> SEQUENCE: 313
gtggttggtt catgttgatg gggtgctatc ctacctgagc ttttctatt attttccttt      60 ttatttttt tcttactttt gttttaatc ttccttgacct tgtaagacct ttcttgacc     120 ttgtaagacc ccttttatg tttatttatc ttaattttg tattgtcata aattctatat     180
caaaattttt tgatatagaa tttcatgttt attttttct gttttgccc aactcatatt     240 ctccttcctt gtctatccct cctgagctat tgaataaaaa ttattatgct                290

<210> SEQ ID NO 314
<211> LENGTH: 278
<212> TYPE: DNA
<213> ORGANISM: Populus sp.

<400> SEQUENCE: 314
gtttcttcat gttaagtggc cggtgctatc ctacctgagc ttttctatt atctcttcgt      60 tttttttttt gttttttttt cttgaccttg taagaccttt tcttgacctt gtaagacccc     120 atttttgtt ctttgtttct attttttgta ttatcatcaa ctttacatca aaatgtcttg     180
atgtagagtt ttgactaatt ttttccccgt ttccgtccaa ctcatcttct ccttccttgt     240
ctatccctcc tgagctatga gctgtttgaa ttagacta                             278

<210> SEQ ID NO 315
<211> LENGTH: 315
<212> TYPE: DNA
<213> ORGANISM: Malus sp.

<400> SEQUENCE: 315
ggaggtgctt gatgtggatt tggtgctatc ctagctgagc ttttttttc cgtctacatc      60 cgtcacgacc atatcctttc atcttctact actttcgcat cgatcccttc ccttttcctt     120
gaccttgtaa gaccttttct tgaccttgta agatgtcatg ccaggtctgt tgtctttgtt     180
ttgcatttcg ccccaagttt tgcatcggaa ttaactgata tacagcttgg cctttgttcc     240
```

```
tcatcgttac cgcccaattc atcttctcct tccttgtcta tccctcctga gctgttccac    300
aattacctca aacta                                                     315

<210> SEQ ID NO 316
<211> LENGTH: 320
<212> TYPE: DNA
<213> ORGANISM: Glycine sp.

<400> SEQUENCE: 316
gcagcttctt cattctaatc tggtgctatc ctatctgagc ttttactac tactactacc     60 cttctttct tcatctaatt tctaccacac ttttctcttt gttttccct tggagtcttc     120 ttcttgacct tgtaagacct tttcttgacc ttgtaagacc tcacacccta tctcttctct    180 ttgttttttgc ttttgtggaa gaccctgtat cactatccac tgatatagag tttgatctcc   240 ttcttttcccc gttaccaccc aactcatact ttccttcctt gtctatccct cctgagctgt   300
tccaatttaa ttaatttggc                                                320

<210> SEQ ID NO 317
<211> LENGTH: 307
<212> TYPE: DNA
<213> ORGANISM: Arabidopsis sp.

<400> SEQUENCE: 317
ttccagtttc aatgataaag cggtgttatc ctatctgagc ttttagtcgg attttttctt    60
ttcaattatt gtgttttatc tagatgatgc atttcattat tctctttttc ttgaccttgt    120
aaggcctttt cttgaccttg taagacccca tctctttcta aacgttttat tattttctcg    180
ttttacagat tctattctat ctcttctcaa tatagaatag atatctatct ctacctctaa    240
ttcgttcgag tcattttctc ctaccttgtc tatcccttcct gagctaatct ccacatatat    300
cttttgt                                                              307

<210> SEQ ID NO 318
<211> LENGTH: 294
<212> TYPE: DNA
<213> ORGANISM: Citrus sp.

<400> SEQUENCE: 318
gcctcccgtt catcctaatt tggtgctatc ctacctgagc ttttcaata attttttcttg    60 atttttttc aagtttttt ttttcttttg tgtcttcttg accttgtaag accttttcttt    120 gaccttgtaa gaccccgtgt tgtgttcttt ccgtttattt ttcgttccgt tataaattct    180
gtatctcaac tttctgatat aggatttaat ctccgttctt ccccgtttcc gcccaactca    240
tcttctcctt ccttgtctat ccctcctgag ctgtttgaat catagtaaaa ataa         294

<210> SEQ ID NO 319
<211> LENGTH: 320
<212> TYPE: DNA
<213> ORGANISM: Gossypium sp.

<400> SEQUENCE: 319
tggcttgttg acctctctct tggtgctatc ccacctgagc ttattttta caatcccccc     60 ctcccccccc cccaaaaaaa aaaaaacta cccttttttt tatttcacca tggtttcctc    120
ttcttgacct tgtaaggcct tttcttgacc ttgtaagacc cctaccatca cctactacac    180
taatcaccaa tatcttaaac catttcttat cagaatttc cttgaaagaa ctaaacaatt    240
agtacccact gttcccacct aactcatcat ctccttcccct gtctatccct cctgagctac   300
```

```
catgtcacaa taaaaaaact                                              320

<210> SEQ ID NO 320
<211> LENGTH: 316
<212> TYPE: DNA
<213> ORGANISM: Theobroma sp.
<220> FEATURE:
<221> NAME/KEY: modified_base
<222> LOCATION: (152)..(152)
<223> OTHER INFORMATION: a, c, t, g, unknown or other
<220> FEATURE:
<221> NAME/KEY: modified_base
<222> LOCATION: (167)..(167)
<223> OTHER INFORMATION: a, c, t, g, unknown or other
<220> FEATURE:
<221> NAME/KEY: modified_base
<222> LOCATION: (169)..(169)
<223> OTHER INFORMATION: a, c, t, g, unknown or other
<220> FEATURE:
<221> NAME/KEY: modified_base
<222> LOCATION: (194)..(194)
<223> OTHER INFORMATION: a, c, t, g, unknown or other
<220> FEATURE:
<221> NAME/KEY: modified_base
<222> LOCATION: (197)..(197)
<223> OTHER INFORMATION: a, c, t, g, unknown or other
<220> FEATURE:
<221> NAME/KEY: modified_base
<222> LOCATION: (226)..(226)
<223> OTHER INFORMATION: a, c, t, g, unknown or other

<400> SEQUENCE: 320
gtggcttgtt catcttaatt gggtgctatc ctacctgagc ttttttttca ctcttttttt    60
tttttaatgc ccttcattct tacttctttc gatttctttt tcttcttctt ttcttatctt   120
cttgaccttg taagaccttt tcttgacctt gnaagacccc gttcggngnt ccttggtttt   180
gtttttctct ccgntgnaga ctctatatca gaactttctg atgtanagtt tgcgtattct   240
tctaccccat tcccgccaac ttttcttctc ccttccttgc tatccctcct gagctggtga   300
attagcctag cctagc                                                  316

<210> SEQ ID NO 321
<211> LENGTH: 301
<212> TYPE: DNA
<213> ORGANISM: Vitis sp.

<400> SEQUENCE: 321
gaggctggtt ggtgttaatt gggttgctat cctacctgag ctttttcttc gttttttttt    60
ttatattttt catcgttttt tttttattct cttttctcg tcttcttgac cttgtaagac   120
cttttcttga ccttgtaaga ccctgttgtg cgcatttctt cttcgttttc catcttgtca   180
tgaactctat accagcaccg actgacatag agctcggcca tcgtgttccc cgtttccgcc   240
caactcatgt tctccttcct tgtctatccc tcctgagcta ttggaattga accaacaccc   300
t                                                                  301

<210> SEQ ID NO 322
<211> LENGTH: 298
<212> TYPE: DNA
<213> ORGANISM: Mesembryanthemum sp.

<400> SEQUENCE: 322
ttccagtttt gaccattctt tggtgctatc ctacctgagc tttattattt aatttctagc    60
tactctcatt cttattatta atcttcaccc ttattagctt cttgaccttg taagaccttt   120
tcttgacctt gtaagaccta gtccctaccc atgacccatt gccaccgcg gaaccaaggt   180
```

```
gttcatgttc ggaactagcc atggacaagt gggcgattag cactcagaat cccettccaa    240 ctcatcatcc tcccttgtgt ctatccctcc tgagctacgt acactctact tctttatt     298

<210> SEQ ID NO 323
<211> LENGTH: 323
<212> TYPE: DNA
<213> ORGANISM: Antirrhinum sp.

<400> SEQUENCE: 323
gctcctttat cgtgttaagc tggtgctatc ctatctgagc ttttttcgtta ttttttatatt   60 ttatttcatt tttcaagtct cactctttga cttgttgcct ttaattttct ccattttcgt   120
ctcttcttga ccttgtaaga ccttttcttg accttgtaag accccgtgtc ttacggtctg   180
tttctctttt cctatttggt acggacacca catcagaatt atctgatgtc gcatgtaccc   240
gttttctctc ttcgttcccg tccaactcac gttctccttc cttgtctatc cctcctgagc   300
tattcgaatt acagagttaa gaa                                            323

<210> SEQ ID NO 324
<211> LENGTH: 316
<212> TYPE: DNA
<213> ORGANISM: Lycopersicon sp.

<400> SEQUENCE: 324
tcgcatcctc atcttaatct cggtgctatc ctacctgagc ttttttctcac cgcttttttt    60 tttctgttgt gtattctctt ttttgacttg ttgccttcg ttcctctacc taccccattc   120
ttcttgacct tgtaagacct tttcttgacc ttgtaagacc ccgtgttatc tcttacgtct   180
ttatgtttcg ttttttgca aatcttacgt catgacttct tcatgtaagc tttgtttggt    240
ctccttcttc tttcctactc aactctcgtc ctccttcctt gtctatccct cctgagctgt   300
tgattttatt ccatgt                                                   316

<210> SEQ ID NO 325
<211> LENGTH: 250
<212> TYPE: DNA
<213> ORGANISM: Hordeum sp.

<400> SEQUENCE: 325
ttgtctcgta gcctataagc cggtgttatc ccgaatgagc tttcttatcc caaaccctcc     60
catatgtctc ttgttaaatc attttctggc tactcctcgt gtcagaatta acgttcttga   120
ccttgtaagg cctttttcttg accttgtaag gccctcccct aacgtttctc gtgcatcctg   180
gtgtctccaa cctcacactt tctttcccct ttctatccct cctgagctat tccctatttt   240
gtacgtctac                                                           250

<210> SEQ ID NO 326
<211> LENGTH: 295
<212> TYPE: DNA
<213> ORGANISM: Oryza sp.

<400> SEQUENCE: 326
gttcatgttt agcaatagca cggtgttatc ctaactgagc ttttcttcta gccaccgtcc     60
acatccttct tcaaaacctc aacatcactt tgtgtgggaa ttaaaaggaa ttggtcttct   120
tgaccttgca agaccttttc ttgaccttgt aagacccaac atcgttgtgt tgttttcctt   180
gtttcttatt tttcaattc atccacctct tctttctacc tcccatcttt ctcctagttc   240
ttgccttctc tctcggtcta tccctcctga gctgtattga tcactttcta tgtta        295
```

<210> SEQ ID NO 327
<211> LENGTH: 281
<212> TYPE: DNA
<213> ORGANISM: Triticum sp.

<400> SEQUENCE: 327

| attcgcccat agcaaaaata tggtgttatc ctgattgagc ttttcttcta cccaccatcc | 60 |
| tcccccttcg tttcctcctc ttcttgctgc gttgtttggg tcttcttgac cttgcaagac | 120 |
| cttttcttga ccttgtaaga cccaacaatg ccacatttcc cctcacgttc ttcatcttct | 180 |
| tattccacct cctttccctg ccatgttcc ttttcacccc tctctcttcc atctttcttc | 240 |
| catctatccc tcctgagcta cattttctta tagttggatt t | 281 |

<210> SEQ ID NO 328
<211> LENGTH: 275
<212> TYPE: DNA
<213> ORGANISM: Saccharum sp.

<400> SEQUENCE: 328

| gttcatgcat agcattatca gggtgttatc ccaattgagc tttttattcg agccatcatc | 60 |
| ctcattcttc ttcatattct ttgcatcgca acgtttgtgg ttttgtaagg tgcggtcttc | 120 |
| ttgaccttgc aagaccttt cttgaccttg taagacccaa ctttgcgatg tttctttcct | 180 |
| ttgactcgat cttctctacc tcacatcttc ttcttcgttc ttatttcttt tctatgtcta | 240 |
| tcccttctga gctgcgttaa gctatgttag gtact | 275 |

<210> SEQ ID NO 329
<211> LENGTH: 275
<212> TYPE: DNA
<213> ORGANISM: Sorghum sp.

<400> SEQUENCE: 329

| gttcatgcgt agtattatca tggcgttatc ctgattgagc ttttcattca agccaccgtt | 60 |
| ctcatccttc ttcgtattct ttgtatccca atgtttgtgg tttcgcaagg tgaggtcttc | 120 |
| ttgaccttgc aagaccttt cttgaccttg taagacccaa ctctgcgaca tctctttcct | 180 |
| tcgactcaat cttctctgtc ttacaccttc ctcttcattc ttacttcttt tctatgtcta | 240 |
| tcccttctga gctgtgttga gctatgttag gtcct | 275 |

<210> SEQ ID NO 330
<211> LENGTH: 328
<212> TYPE: DNA
<213> ORGANISM: Zea sp.

<400> SEQUENCE: 330

| ctcctagcct atatatgaac tggtgttatc ccgactgaac ttttcttttt gttgacacct | 60 |
| ttcgtcaggc ctctccacca gaggttgact cgtatgtctg ttttctggtt tctcatacca | 120 |
| gaattaacgt tcttgacctt gtaaggcctc ttcttgacct tgtaaggctc tcactctgtg | 180 |
| tctgcatcct tctcgcatcc cttgtttcct tctttcccac tacatgcagg atcagtcccg | 240 |
| atattgccgt gtttgccagc cttctgcatc cacctacttt ctgttcccctt ctatccctcc | 300 |
| tgagctaatt gttgctccta tgtaatcc | 328 |

<210> SEQ ID NO 331
<211> LENGTH: 320
<212> TYPE: DNA
<213> ORGANISM: Pinus sp.

```
<400> SEQUENCE: 331
ggcaataata atatgatgtt cgacgctatc ccctctgagc ttttataacc taaaacttgt    60
ctatcctcta cgaaacccat gtcattaact catgccaact ttgtatgtag tgtaacatga   120
aagtgtggcc ttcttgacct tgtacgacct tttcttgacc ttgtaagacc caacatcaaa   180
gcgcgagagc agcagcatat ttctactact cactgttttc tattctagca tgccagcact   240
aggagtgggg gtgaggccgt ttagctatca atctaactta ctctatctct cctgagctat   300
gtatacatct gattttgaag                                               320

<210> SEQ ID NO 332
<211> LENGTH: 21
<212> TYPE: RNA
<213> ORGANISM: Arabidopsis thaliana

<400> SEQUENCE: 332
gguguuauca uacuagugau u                                              21

<210> SEQ ID NO 333
<211> LENGTH: 21
<212> TYPE: RNA
<213> ORGANISM: Arabidopsis thaliana

<400> SEQUENCE: 333
gguguuaucc cuccugagcu u                                              21

<210> SEQ ID NO 334
<211> LENGTH: 22
<212> TYPE: RNA
<213> ORGANISM: Arabidopsis thaliana

<400> SEQUENCE: 334
cuugucuauc ccacuagugc ua                                             22

<210> SEQ ID NO 335
<211> LENGTH: 21
<212> TYPE: RNA
<213> ORGANISM: Arabidopsis thaliana

<400> SEQUENCE: 335
guugaucgga ugguagaaga a                                              21

<210> SEQ ID NO 336
<211> LENGTH: 21
<212> TYPE: RNA
<213> ORGANISM: Arabidopsis thaliana

<400> SEQUENCE: 336
gugaccuaua acacucucau a                                              21
```